(12) United States Patent
Musicki et al.

(10) Patent No.: US 9,090,596 B2
(45) Date of Patent: Jul. 28, 2015

(54) DISUBSTITUTED 3,4-DIAMINO-3-CYCLOBUTENE-1,2-DIONE COMPOUNDS FOR USE IN THE TREATMENT OF CHEMOKINE-MEDIATED PATHOLOGIES

(71) Applicant: GALDERMA RESEARCH & DEVELOPMENT, Biot (FR)

(72) Inventors: Branislav Musicki, Nice (FR); Jerôme Aubert, Grasse (FR); Jean-Guy Boiteaux, Valbonne (FR); Laurence Clary, La Colle-sur-Loup (FR); Patricia Rossio, Grasse (FR); Marlène Schuppli-Nollet, Le Bar sur Loup (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/354,500

(22) PCT Filed: Oct. 26, 2012

(86) PCT No.: PCT/FR2012/052479
§ 371 (c)(1),
(2) Date: Apr. 25, 2014

(87) PCT Pub. No.: WO2013/061005
PCT Pub. Date: May 2, 2013

(65) Prior Publication Data
US 2014/0309208 A1    Oct. 16, 2014

Related U.S. Application Data

(60) Provisional application No. 61/552,829, filed on Oct. 28, 2011.

(30) Foreign Application Priority Data

Oct. 28, 2011 (FR) ...................... 11 59829

(51) Int. Cl.
| | | |
|---|---|---|
| C07D 407/14 | (2006.01) |
| C07D 409/14 | (2006.01) |
| C07D 413/14 | (2006.01) |
| C07D 405/14 | (2006.01) |
| A61K 31/506 | (2006.01) |
| A61K 31/4709 | (2006.01) |
| A61K 31/4427 | (2006.01) |
| A61K 31/4192 | (2006.01) |
| A61K 31/4184 | (2006.01) |
| A61K 31/381 | (2006.01) |
| A61K 31/422 | (2006.01) |
| A61K 31/351 | (2006.01) |
| A61K 31/4015 | (2006.01) |
| C07D 405/06 | (2006.01) |
| C07D 407/06 | (2006.01) |

(52) U.S. Cl.
CPC ............ *C07D 407/14* (2013.01); *A61K 31/351* (2013.01); *A61K 31/381* (2013.01); *A61K 31/4015* (2013.01); *A61K 31/4184* (2013.01); *A61K 31/4192* (2013.01); *A61K 31/422* (2013.01); *A61K 31/4427* (2013.01); *A61K 31/4709* (2013.01); *A61K 31/506* (2013.01); *C07D 405/06* (2013.01); *C07D 405/14* (2013.01); *C07D 407/06* (2013.01); *C07D 409/14* (2013.01); *C07D 413/14* (2013.01)

(58) Field of Classification Search
CPC .. C07D 407/14; C07D 409/14; C07D 413/14; C07D 405/14; A61K 31/506; A61K 31/4709; A61K 31/4427; A61K 31/4192; A61K 31/4184; A61K 31/381; A61K 31/422; A61K 31/351; A61K 31/4015
See application file for complete search history.

(56) References Cited

U.S. PATENT DOCUMENTS 7,960,433 B2 *  6/2011  Taveras et al. ................ 514/468

FOREIGN PATENT DOCUMENTS

| WO | 02/083624 A1 | 10/2002 |
| WO | 2008/005570 A1 | 1/2008 |
| WO | 2010/063802 A1 | 6/2010 |

OTHER PUBLICATIONS

International Search Report dated Jan. 2, 2013 corresponding to International Patent Application No. PCT/FR2012/052479, 10 pages (with English translation).

\* cited by examiner

*Primary Examiner* — Joseph Kosack
*Assistant Examiner* — Matthew Coughlin
(74) *Attorney, Agent, or Firm* — Dentons US LLP

(57) ABSTRACT

Disubstituted 3,4-diamino-3-cyclobutene-1,2-dione compounds are disclosed that are represented by general formula (I). Also disclosed, are pharmaceutical compositions including these compounds and methods of using these compounds and compositions for the treatment of chemokine-mediated pathologies.

9 Claims, 2 Drawing Sheets

Figure 1:
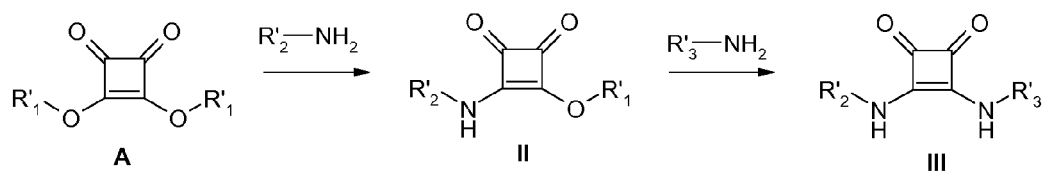

DISUBSTITUTED 3,4-DIAMINO-3-CYCLOBUTENE-1,2-DIONE COMPOUNDS FOR USE IN THE TREATMENT OF CHEMOKINE-MEDIATED PATHOLOGIES

CROSS-REFERENCE TO PRIOR APPLICATIONS

This application is a National Stage of PCT/FR2012/052479, filed Oct. 26, 2012, and designating the United States (published in English on May 2, 2013, as WO 2013/061005 A1), which claims priority under 35 U.S.C. §119 to U.S. Provisional Patent Application No. 61/552,829, filed Oct. 28, 2011, and French Patent Application No. 1159829, filed Oct. 28, 2011 each hereby expressly incorporated by reference in its entirety and each assigned to the assignee hereof.

FIELD OF THE INVENTION

The present invention relates to novel disubstituted 3,4-diamino-3-cyclobutene-1,2-dione compounds, to the pharmaceutical compositions containing these compounds and also to the use of these compounds and of these compositions for the treatment of chemokine-mediated pathologies.

STATE OF THE ART PRIOR TO THE INVENTION

Chemokines or cytokines are small soluble proteins. Their most well-known role is the attraction of immune system cells and the control of the activation state of said cells. All chemokines perform their functions by binding to G protein-coupled receptors. Some chemokines are considered to be pro-inflammatory. The secretion of these chemokines can be induced during the immune response in order to promote the arrival of immune system cells at an infectious site.

There are two types of chemokines pro-inflammatory chemokines and constitutive chemokines.

The pro-inflammatory (or "inducible") chemokines are produced at sites of inflammation by tissue cells or leukocytes that have infiltrated, after contact with a pathogenic agent.

The constitutive (or "homeostatic") chemokines are produced in the lymphoid organs and in certain non-lymphoid organs such as the skin and mucous membranes. They regulate lymphocyte trafficking and the localization of lymphocytes within these organs during lymphopoiesis, but also for maintaining immunosurveillance.

The nomenclature of these chemokine receptors is based on the group of chemokines to which its ligand belongs. Thus, the receptors corresponding to the chemokines of the CXC group are, for example, called CXCR1, CXCR2, CXCR3, CXCR4, etc., and the receptors corresponding to the chemokines of the CC group are, for example, called CCR1, CCR2, CCR3, etc. These receptors all have a similar tertiary structure, and they are coupled to a G protein: they are therefore part of the GPCR (G Protein-Coupled Receptor) superfamily. Interleukin-8 or IL-8 (also known as CXCL-8) is a member of the CXC chemokine family, which plays an essential role in the recruitment of neutrophils to the inflammation site. Two receptors, CXCR1 & CXCR2, are known to be specifically activated by IL-8. While CXCR2 binds with strong affinity to IL-8 and to the related chemokines, such as CXCL6, CXCL5, CXCL3, CXCL2 and CXCL1, CXCR1 binds only to IL-8. High levels of IL-8 and of related chemokines (CXCL5, CXCL2 & CXCL1) have been described in the lesions of inflammatory acne (J Invest Dermatol. 2006; 126:1071-9; Am J Pathol. 2005; 166(6):1691-9; Diagn Pathol. 2007 Jan. 30; 2:4).

First indications demonstrate the expression of CXCR2 in inflammatory acne (Trivedi et al. J Invest Dermatol. 2006 126(5):1071-9). Thus, double antagonists of CXCR1 and CXCR2 might make it possible to rapidly reduce the harmful effects of the IL-8-mediated inflammatory response.

Patent application WO 02/083624 (Schering/Pharmacopeia) discloses more particularly substituted 1,2-cyclobutenedione compounds capable of modulating the activity of CXC-type chemokine receptors, and more particularly the activity of the CXCR1 and CXCR2 receptors. Among these compounds, the compound SCH-527123 (corresponding to example 360.71 on page 281), also called Navarixin, is in the process of being developed (Phase II) for the treatment of chronic obstructive pulmonary disease (or COPD). This compound has also been the subject of phase II studies in asthma and in psoriasis, but these developments have been stopped.

It is currently known that many pathologies of inflammatory type are mediated by chemokines. However, there is a need, which has not been met to date, to treat the inflammatory component of the pathologies of interest in the dermatology field, for instance acne, rosacea or alternatively neutrophilic dermatosis, in particular psoriasis.

Likewise, the promise of obtaining effective new therapies for treating chemokine-mediated diseases using chemokine receptor antagonists has not been fulfilled. Indeed, several clinical studies have failed in phase II. One of the reasons which may explain these failures is the overlap of the biological effects of the various chemokines induced in a pathological situation. To date, the objective of the standard drug discovery process is to identify molecules which target a specific receptor without an off target effect. This approach is without doubt not the most suitable for treating complex inflammatory diseases. An increasing number of approaches appear to favor the search for antagonist molecules with a broad spectrum of action (promiscuous compounds), said approaches possibly thus proving to be more effective in treating complex and multifactorial diseases. (Frantz S. Drug discovery: playing dirty. Nature. 2005 Oct. 13; 437(7061):942-3; Roth B L, Sheffler D J, Kroeze W K. Magic shotguns versus magic bullets: selectively non-selective drugs for mood disorders and schizophrenia. Nat Rev Drug Discov. 2004 April; 3(4): 353-9.)

As it happens, the applicant has discovered novel compounds which not only have an antagonist activity with respect to receptors of CXCR1 and CXCR2 type, but also a strong antagonist activity with respect to chemokine receptors, in particular CCR6 and CXCR3 receptors. These novel compounds surprisingly exhibit a polypharmacology, which makes them of additional interest compared with the already known compounds in the treatment of chemokine-mediated pathologies, and more particularly pathologies of dermatological type. Furthermore, these novel compounds exhibit a hepatic stability which is much lower than that of the already described compounds capable of blocking the activation of CXCR1 and CXCR2 receptors, for instance the SCH-527123 compound. This particular property provides the advantage of having novel compounds which, surprisingly, have a profile that is more suitable for the topical treatment of pathologies of dermatological type. Indeed, their hepatic instability leads to low, or even zero, systemic exposure, and therefore limited side effects. Another particularity of the compounds described in the present invention is their dissociation constant with respect to receptors of CXCR1 and CXCR2 type, said constant being much lower than that of the compounds described in the patent application WO 02/083624, for instance SCH-527123. Indeed, the SCH-527123 molecule has been described as having a dissociation time of about 22 h (pseudo-irreversible dissociation) (Pharmacological Characterization of SCH-527123, a Potent Allosteric CXCR1/CXCR2 Antagonist. JPET 322:477-485, 2007), whereas the dissociation times of the compounds of the present invention are much shorter.

Examples in the literature show that rapid dissociation of antagonists promotes a decrease in their toxicity. This has been described for the antagonists of dopamine D2 receptors (*Am J Psychiatry* (2001) 158(3):360-369), and of N-methyl-D-aspartate (NMDA) receptors (Nat Rev Drug Disc (2006) 5(2):160-170.) and also for nonsteroidal anti-inflammatory drugs (*Lett Drug Des Discov* (2006) 3(8):569-574. and *Pharm Med* (2008) 22(1):23-34). Indeed, a long dissociation time would have the tendency to induce adverse effects. With rapid dissociation times, the compounds according to the invention consequently exhibit reduced side effects.

SUMMARY OF THE INVENTION

Thus, a first subject according to the invention relates to novel disubstituted 3,4-diamino-3-cyclobutene-1,2-dione compounds corresponding to general formula (I) below:

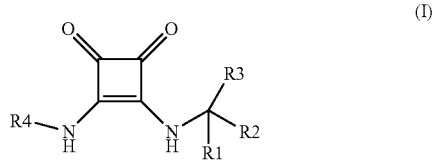

and also the pharmaceutically acceptable salts, solvates or hydrates thereof, for which the substituents R1, R2, R3 and R4 are as defined hereinafter in the detailed description of the invention.

A second subject according to the invention relates to a pharmaceutical composition comprising an effective amount of a compound corresponding to general formula (I), or of one of the pharmaceutically acceptable salts thereof or one of the pharmaceutically acceptable solvates or hydrates thereof, in combination with a pharmaceutically acceptable solvent or support.

A third subject according to the invention relates to a compound or a pharmaceutical composition as described above, for use as a medicament.

A fourth subject according to the invention relates to a compound or a pharmaceutical composition as described above, for use in the treatment of chemokine-mediated diseases.

A fifth subject according to the invention relates to a compound or a pharmaceutical composition as described above, for use in the treatment of diseases of the group comprising neutrophilic dermatosis, and in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

DETAILED DESCRIPTION OF THE INVENTION

Unless otherwise indicated, the following definitions apply to the entire description and claims.

These definitions apply independently of whether a term is used alone or in combination with other terms. Thus, for example, the definition of the term "aryl" applies both to "aryl" as such and to the "aryl" part of the term "aryloxy".

"Alkyl" denotes a linear or branched, saturated hydrocarbon-based chain of which the number of carbon atoms is specified.

When the number of carbon atoms is not specified, this means that the alkyl chain contains from 1 to 20 carbon atoms.

The preferred alkyl radicals contain from 1 to 12 carbon atoms, and those which are even more preferred contain from 1 to 6 carbon atoms in the chain.

"Alkoxy" denotes an oxygen substituted with an alkyl radical as previously defined. Examples of alkoxy radicals include methoxy, ethoxy, n-propoxy, isopropoxy and n-butoxy radicals.

"Aryl" denotes a monocyclic or polycyclic (2 to 3 cycles) aromatic cyclic system comprising from 6 to 14 carbon atoms, and preferably from 6 to 10 carbon atoms.

By way of examples of an aryl radical, mention may be made of phenyl, naphthyl, indenyl, tetrahydronaphthyl, indanyl, anthracenyl and fluorenyl radicals.

"Heteroaryl" denotes a monocyclic or polycyclic (2 to 3 cycles) aromatic system comprising from 5 to 14 cyclic atoms, preferably from 5 to 10 cyclic atoms, in which one or more of the cyclic atoms represent(s) one or more (1 to 5) heteroatom(s) chosen from the group comprising nitrogen, oxygen and sulfur.

The preferred heteroaryls contain 5 or 6 cyclic atoms and 1 to 3 heteroatoms.

The prefix aza, oxa or thia before the name of the root heteroaryl signifies that at least one nitrogen, one oxygen or one sulfur is respectively present in the ring.

A nitrogen atom of a heteroaryl can be optionally oxidized to N-oxide.

By way of examples of appropriate heteroaryls, mention may be made of the following heteroaryls:

pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4 triazinyl and benzothiazolyl.

"Arylalkyl" denotes a radical of which the aryl and alkyl parts are as defined above.

By way of examples of arylalkyl, mention may be made of benzyl, phenethyl and naphthalenylmethyl radicals.

The linkage to the structure to which it is attached is via the alkyl radical.

"Heteroarylalkyl" denotes a radical of which the heteroaryl and alkyl parts are as defined above.

By way of examples of heteroarylalkyl, mention may be made of pyridylmethyl, pyridylethyl, imidazolylmethyl, imidazolylethyl, pyrazolylmethyl and pyrazolylethyl radicals.

The linkage to the structure to which it is attached is via the alkyl radical.

"Cycloalkyl" denotes a nonaromatic hydrocarbon-based cyclic system, having from 3 to 10 carbon atoms, preferably from 5 to 10 carbon atoms, and from one to three rings.

The preferred cycloalkyl radicals contain from 5 to 7 cyclic atoms.

By way of examples of cycloalkyl radicals, mention may be made of cyclopropyl, cyclopentyl, cyclohexyl, cycloheptyl, norbornyl and adamantyl radicals.

"Cycloalkylalkyl" denotes a radical of which the cycloalkyl and alkyl parts are as defined above.

By way of examples of cycloalkylalkyl, mention may be made of cyclopropylmethyl, cyclopropylethyl, cyclobutylmethyl, cyclobutylethyl, cyclopentylmethyl, cyclopentylethyl, cyclohexylmethyl, cyclohexylethyl, norbornylmethyl and adamantylmethyl radicals.

The linkage to the structure to which it is attached is via the alkyl radical.

"Heterocycloalkyl" denotes a nonaromatic hydrocarbon-based cyclic system, having from 4 to 10 carbon atoms, preferably from 5 to 10 carbon atoms, and from one to three rings, and comprising from one to three heteroatoms chosen from the group consisting of nitrogen, oxygen and sulfur.

The preferred heterocycloalkyl radicals contain from 5 to 7 cyclic atoms.

By way of examples of heterocycloalkyl radicals, mention may be made of tetrahydrofuranyl, tetrahydrothiophenyl, tetrahydropyranyl and 7-oxabicyclo[2.2.1]heptanyl groups.

"Fluoroalkyl" denotes an alkyl radical as previously defined, substituted with one or more fluorine atoms.

By way of examples of fluoroalkyl radicals, mention may be made of fluoromethyl, difluoromethyl, 2-fluoroethyl, 2,2-difluoroethyl and 2,2,2-trifluoroethyl radicals.

"Perfluoroalkyl" denotes an alkyl radical as previously defined, in which each hydrogen atom has been substituted with a fluorine atom.

By way of examples of perfluoro radicals, mention may be made of trifluoromethyl and pentafluoroethyl radicals.

Thus, a first subject according to the invention relates to novel disubstituted 3,4-diamino-3-cyclobutene-1,2-dione compounds corresponding to general formula (I) below, or one of the pharmaceutically acceptable salts or solvates thereof:

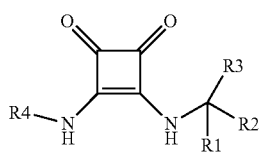

(I)

in which,
R1 represents a hydrogen atom or a methyl,
R2 represents a ring comprising four atoms, chosen from the structures (1) and (2) below:

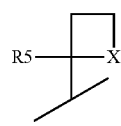

(1)

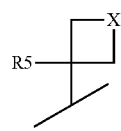

(2)

in which R5 and X have the meaning given hereinafter,

R3 represents an aromatic or heteroaromatic ring selected from the group consisting of the rings corresponding to formulae (a) to (o) below:

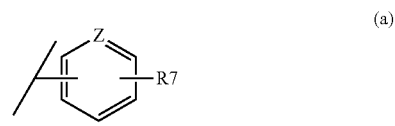

(a)

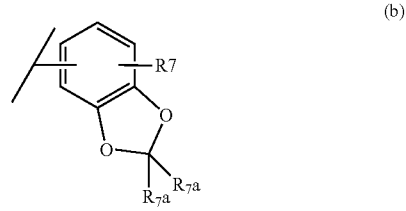

(b)

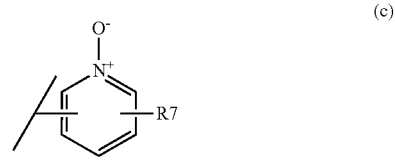

(c)

(d)

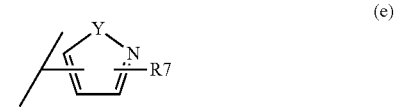

(e)

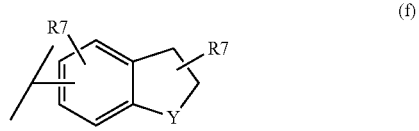

(f)

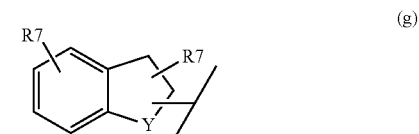

(g)

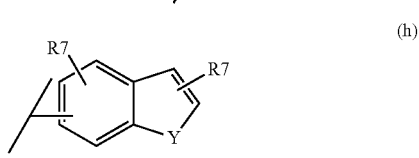

(h)

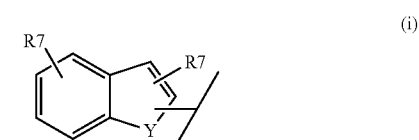

(i)

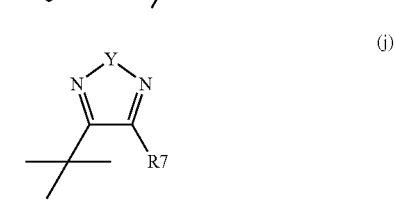

(j)

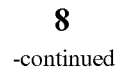
(k)

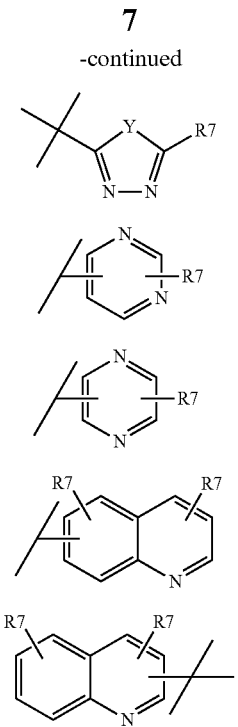

(l)

(m)

(n)

(o)

in which R7, R7a, Y and Z have the meaning given hereinafter, it being specified that the rings (a) to (o) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p) to (z) and (aa) to (ak) below:

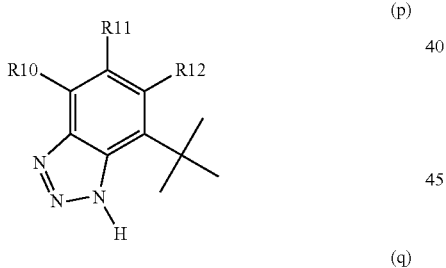
(p)

(q)

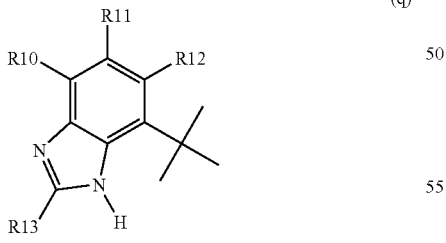
(r)

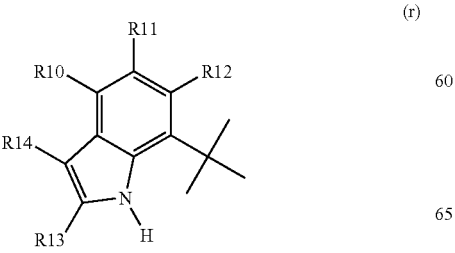

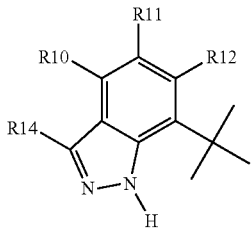
(s)

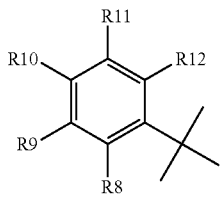
(t)

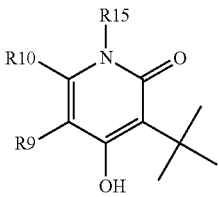
(u)

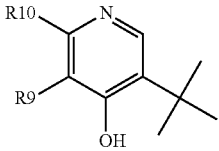
(v)

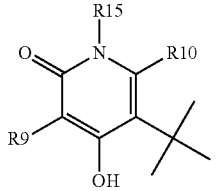
(w)

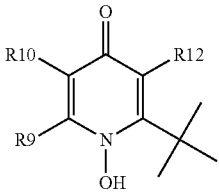
(x)

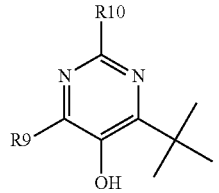
(y)

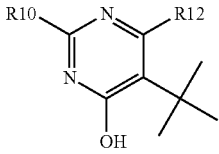
(z)

(aa) 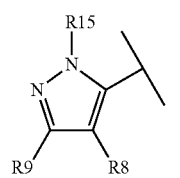

(ab) 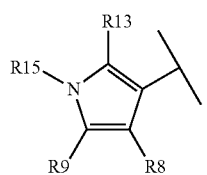

(ac) 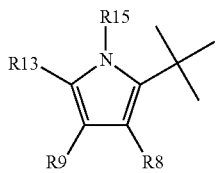

(ad) 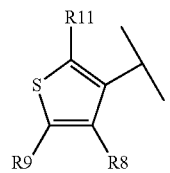

(ae) 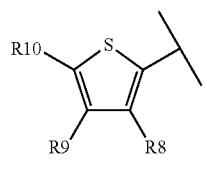

(af) 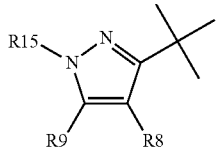

(ag) 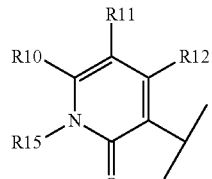

(ah) 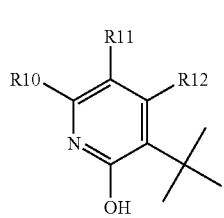

(ai) 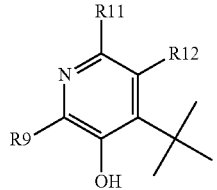

(aj) 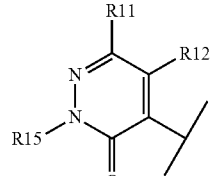

(ak) 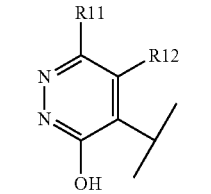

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a radical R16, a halogen, —CF₃, —COR16, —OR16, —NR16R17, —NO₂, —CN, —SO₂R16, —SO₂NR16R17, —NR16COR17, —CONR16R17, —NR16CO₂R17 or —CO₂R16, R7a represents a hydrogen atom or else an alkyl radical having from 1 to 5 carbon atoms, R8 represents a hydrogen atom, a halogen atom, or an —OH, —SH, —CONHOR16, —CONR16OH, —NR16R17, —SO₃H, —OCOR16, —NHSO₂R16, —SO₂NR16R17, —NHCOR16, —CONR16R17, —NR16CO₂R17, —NHSO₂NR16R17, —CO₂R16, pyrrolyl, imidazolyl, triazolyl or tetrazolyl radical, R9, R10, R11 and R12 are identical or different and are independently chosen from the group consisting of a hydrogen, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 or —CO₂R16 radical, or alternatively, when two of the R9, R10, R11 and R12 radicals are in the ortho position on an aromatic or heteroaromatic ring selected from the group consisting of the rings corresponding to formulae (p) to (z) and (aa) to (ak) above, then they can together form, with the bond which links them together, an aryl, heteroaryl, cycloalkyl or heterocycloalkyl ring, R13 and R14 are identical or different and are independently chosen from the group consisting of a hydrogen atom, a halogen atom, an alkyl, —CF₃, —OCF₃, —OH, —SH, —CN, —SO₂R16, —SO₂NR16R17, —NHSO₂NR16R17, —NR16R17, —NR16CONR16R17, —NR16COR17, —NR16CO₂R17, —CONR16R17, —COR16 and —CO₂R16, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one preferred embodiment according to the invention, the compounds, and also the pharmaceutically acceptable salts, solvates or hydrates thereof, correspond to the above-mentioned formula (I) in which:

R1 represents a hydrogen atom,

R2 represents a four-membered ring corresponding to structure (2) below:

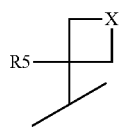
(2)

in which R5 and X have the meaning given hereinafter,

R3 represents an aromatic or heteroaromatic ring selected from the group consisting of the rings corresponding to formulae (a), (b) and (d) below:

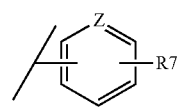
(a)

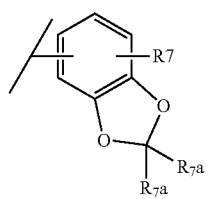
(b)

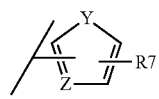
(d)

in which R7, R7a, Y and Z have the meaning given hereinafter, it being specified that the rings (a), (b) and (d) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

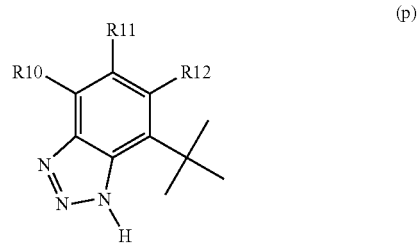
(p)

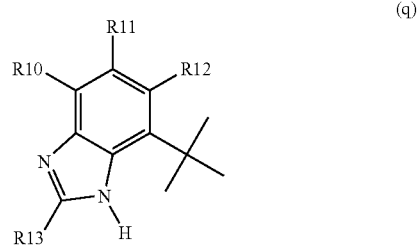
(q)

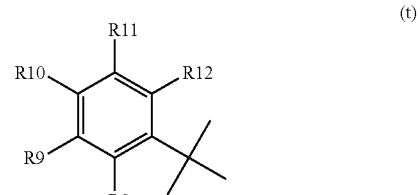
(t)

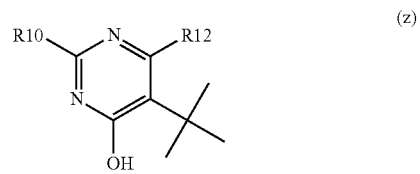
(z)

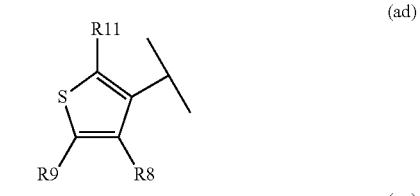
(ad)

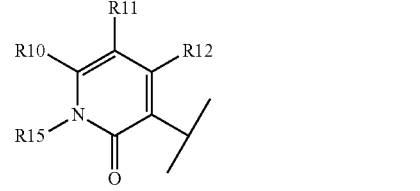
(ag)

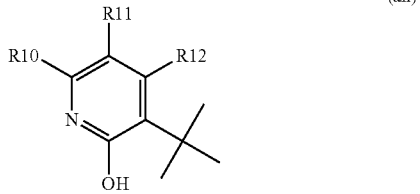
(ah)

in which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R7a represents a hydrogen atom or else an alkyl radical having from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, then they can together form, with the bond which links them together, an aryl, heteroaryl, cycloalkyl or heterocycloalkyl ring, R13 is chosen from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 or —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one more particularly preferred embodiment of the invention, the compounds, and also the pharmaceutically acceptable salts, solvates or hydrates thereof, correspond to the abovementioned formula (I) in which:

R1 represents a hydrogen atom,

R2 represents a ring comprising four atoms, corresponding to structure (2) below:

(2)

in which R5 and X have the meaning given hereinafter,

R3 represents a heteroaromatic ring corresponding to formula (d) below:

(d)

in which R7, Y and Z have the meaning given hereinafter, it being specified that the ring (d) can optionally bear several R7 groups, which may be identical or different, the total number of such R7 groups being at most equal to the number of substitutable atoms of the ring; R4 represents an aromatic or heteroaromatic ring selected from the group consisting of the rings corresponding to formulae (p), (q), (t), (z), (ad), (ag) and (ah) below:

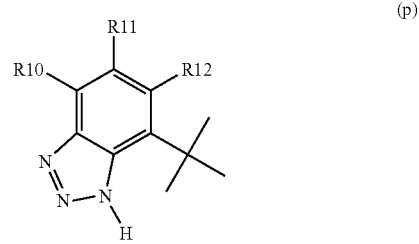

(p)

(q)

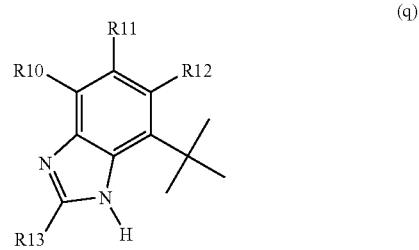

(t)

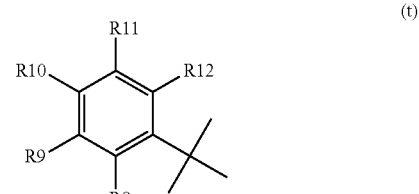

(z)

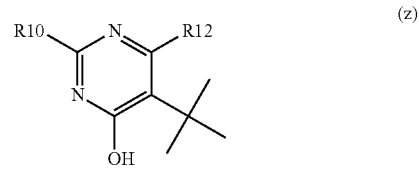

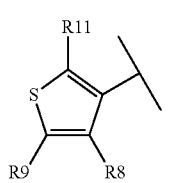

(ad)

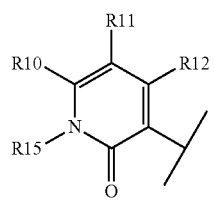

(ag)

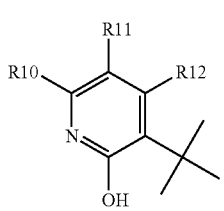

(ah)

in which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen atom, or an R16, —CF₃, —COR16, —OR16, —NR16R17, —NO₂, —CN, —SO₂R16, —SO₂NR16R17, —NR16COR17, —CONR16R17, —NR16CO₂R17 or —CO₂R16 radical, R8 represents a hydrogen atom, or an —OH, —SH, —CONHOR16, —CONR16OH, —NR16R17, —SO₃H, —OCOR16, —NHSO₂R16, —SO₂NR16R17, —NHCOR16, —CONR16R17, —NR16CO₂R17, —NHSO₂NR16R17, —CO₂R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 or —CO₂R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, they can together form, with the bond which links them together, an aryl, heteroaryl, cycloalkyl or heterocycloalkyl ring, R13 is chosen from the group consisting of a hydrogen atom, a halogen atom, and an alkyl, —CF₃, —OCF₃, —OH, —SH, —CN, —SO₂R16, —SO₂NR16R17, —NHSO₂NR16R17, —NR16R17, —NR16CONR16R17, —NR16COR17, —NR16CO₂R17, —CONR16R17, —COR16 or —CO₂R16 radical, R15 represents a hydrogen atom, or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH₂COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one even more particularly preferred embodiment according to the invention, the compounds, and also the pharmaceutically acceptable salts, solvates or hydrates thereof, correspond to the abovementioned formula (I) in which:

R1 represents a hydrogen atom,

R2 represents a ring comprising four atoms, corresponding to structure (2) below:

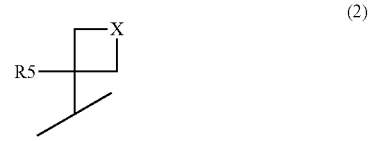

(2)

in which R5 and X have the meaning given hereinafter,

R3 represents a heteroaromatic ring corresponding to formula (d) below:

(d)

in which R7, Y and Z have the meaning given hereinafter, it being specified that the ring (d) can optionally bear several R7 groups, which may be identical or different, the total number of such R7 groups being at most equal to the number of substitutable atoms of the ring; R4 represents an aromatic ring corresponding to formula (t) below:

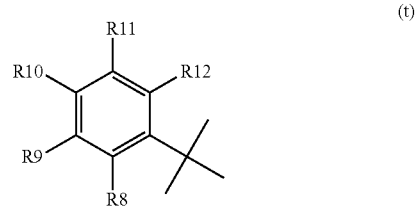

(t)

in which R8, R9, R10, R11 and R12 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a radical R16, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on the aromatic ring (t), they can together form, with the bond which links them together, an aryl, heteroaryl, cycloalkyl or heterocycloalkyl ring, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

Among the compounds which are more particularly preferred, mention may be made, for example, of those chosen from the list comprising:

1/ 2-hydroxy-N,N-dimethyl-3-(2-{[((R)-5-methylfuran-2-yl)-(3-methyloxetan-3-yl)methyl]amino}-3,4-dioxocyclobut-1-enylamino)benzamide 2/ 3-(2-{[(3-fluoromethyloxetan-3-yl)-(5-methyl-furan-2-yl)methyl]amino}-3,4-dioxocyclobut-1-enylamino)-2-hydroxy-N,N-dimethylbenzamide 3/ 3-(2-{[(3-ethyloxetan-3-yl)-(5-methylfuran-2-yl)methyl]amino}-3,4-dioxocyclobut-1-enylamino)-2-hydroxy-N,N-dimethylbenzamide 4/ 2-hydroxy-3-(2-{[(5-methylfuran-2-yl)-(3-methyloxetan-3-yl)methyl]amino}-3,4-dioxocyclobut-1-enylamino)benzoic acid 5/ 3-[2-hydroxy-3-((R)-3-hydroxypyrrolidine-1-carbonyl)phenylamino]-4-{[(5-methylfuran-2-yl)-(3-methyloxetan-3-yl)methyl]amino}cyclobut-3-ene-1,2-dione 6/ 3-[2-hydroxy-3-((S)-3-hydroxypyrrolidine-1-carbonyl)phenylamino]-4-{[(5-methylfuran-2-yl)-(3-methyloxetan-3-yl)methyl]amino}cyclobut-3-ene-1,2-dione 7/ (R)-1-[2-hydroxy-3-(2-{[(5-methylfuran-2-yl)-(3-methyloxetan-3-yl)methyl]amino}-3,4-dioxocyclobut-1-enylamino)benzoyl]pyrrolidine-2-carboxylic acid tert-butyl ester 8/ methyl (R)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate 9/ methyl (S)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate 10/ (R)-1-[2-hydroxy-3-(2-{[(5-methylfuran-2-yl)-(3-methyloxetan-3-yl)methyl]amino}-3,4-dioxocyclobut1-enylamino)benzoyl]pyrrolidine-2-carboxylic acid 11/ 3-[2-hydroxy-3-(1-hydroxyethyl)phenylamino]-4-{[(5-methylfuran-2-yl)-(3-methyloxetan-3-yl)methyl]amino}cyclobut-3-ene-1,2-dione 12/ 3-(2-hydroxy-3-isobutyrylphenylamino)-4-{[(5-methylfuran-2-yl)-(3-methyloxetan-3-yl)methyl]amino}cyclobut-3-ene-1,2-dione 13/ 3-(4-hydroxy-2-methyl-3-oxo-2,3-dihydro-1H-isoindol-5-ylamino)-4-{[(5-methylfuran-2-yl)-(3-methyloxetan-3-yl)methyl]amino}cyclobut-3-ene-1,2-dione 14/ 3-[2-hydroxy-3-(pyrrolidine-1-carbonyl)phenylamino]-4-{[(5-methylfuran-2-yl)-(3-methyloxetan-3-yl)methyl]amino}cyclobut-3-ene-1,2-dione 15/ 3-[2-hydroxy-3-(morpholine-4-carbonyl)phenylamino]-4-{[(5-methylfuran-2-yl)-(3-methyloxetan-3-yl)methyl]amino}cyclobut-3-ene-1,2-dione 21/ 2-hydroxy-N,N-dimethyl-3-(2-{[(5-methylfuran-2-yl)-(3-methyloxetan-3-yl)methyl]amino}-3,4-dioxocyclobut-1-enylamino)benzenesulfonamide 22/ 2-hydroxy-N,N-dimethyl-3-(2-{[(R)-(5-methylfuran-2-yl)-(3-methyloxetan-3-yl)methyl]amino}-3,4-dioxocyclobut-1-enylamino)benzenesulfonamide 24/ 3-{[(5-methyl-furan-2-yl)-(3-methyloxetan-3-yl)methyl]amino}-4-(2-oxo-2,3-dihydrobenzooxazol-7-ylamino)cyclobut-3-ene-1,2-dione 26/ tert-butyl 3-[[2-(3-dimethylcarbamoyl-2-hydroxyphenylamino)-3,4-dioxo-cyclobut-1-enylamino]-(5-methylfuran-2-yl)methyl]-3-methylazetidine-1-carboxylate 27/ 3-(2-{[(4,5-dimethylfuran-2-yl)-(3-methyloxetan-3-yl)methyl]amino}-3,4-dioxocyclobut-1-enylamino)-2-hydroxy-N,N-dimethylbenzamide 31/ 3-[3-(3-hydroxypyrrolidine-1-carbonyl)phenylamino]-4-{[(5-methylfuran-2-yl)-(3-methyloxetan-3-yl)methyl]amino}cyclobut-3-ene-1,2-dione 32/ methyl 1-[3-(2-{[(5-methylfuran-2-yl)-(3-methyloxetan-3-yl)methyl]amino}-3,4-dioxocyclobut-1-enylamino)benzoyl]piperidine-2-carboxylate 33/ methyl 1-[3-(2-{[(5-methylfuran-2-yl)-(3-methyloxetan-3-yl)methyl]amino}-3,4-dioxocyclobut-1-enylamino)benzoyl]pyrrolidine-2-carboxylate 34/ 2-hydroxy-N,N-dimethyl-3-(2-{[(3-methyloxetan-3-yl)thiophen-2-ylmethyl]amino}-3,4-dioxocyclobut-1-enylamino)benzamide 35/ 2-hydroxy-N,N-dimethyl-3-(2-{[(3-methyloxetan-3-yl)-(5-methylthiophen-2-yl)methyl]amino}-3,4-dioxocyclobut-1-enylamino)benzamide 36/ 3-(2-{[furan-2-yl-(3-methyloxetan-3-yl)methyl]amino}-3,4-dioxocyclobut-1-enylamino)-2-hydroxy-N,N-dimethylbenzamide 37a/ 2-hydroxy-N,N-dimethyl-3-(2-{[(4-methylfuran-2-yl)-(3-methyloxetan-3-yl)methyl]amino}-3,4-dioxocyclobut-1-enylamino)benzamide 37b/ 2-hydroxy-N,N-dimethyl-3-(2-{[(3-methylfuran-2-yl)-(3-methyloxetan-3-yl)methyl]amino}-3,4-dioxocyclobut-1-enylamino)benzamide 38/ 2-hydroxy-N,N-dimethyl-3-(2-{[(4-isopropylfuran-2-yl)-(3-methyloxetan-3-yl)methyl]amino}-3,4-dioxocyclobut-1-enylamino)benzamide 42/ 2-hydroxy-3-(2-{[(5-methylfuran-2-yl)-(3-methyloxetan-3-yl)methyl]amino}-3,4-dioxocyclobut-1-enylamino)benzonitrile 43/ methyl (R)-1-[3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate 44/ methyl (S)-1-[4-chloro-3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate 49/ 2-hydroxy-N,N-dimethyl-3-(2-{[((R)-5-methylfuran-2-yl)-(3-methyloxetan-3-yl)methyl]amino}-3,4-dioxocyclobut-1-enylamino)benzamide 51/ methyl {[2-hydroxy-3-(2-{[(R)-(5-methylfuran-2-yl)-(3-methyloxetan-3-yl)methyl]amino}-3,4-dioxocyclobut-1-enylamino)benzoyl]methylamino}acetate 52/ 6-chloro-2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide 53/ 3-[4-chloro-2-hydroxy-3-(4-methylpiperazine-1-sulfonyl)phenylamino]-4-{[(R)-(5-methylfuran-2-yl)-(3-methyloxetan-3-yl)methyl]amino}cyclobut-3-ene-1,2-dione A second subject according to the invention relates to a pharmaceutical composition comprising an effective amount of a compound corresponding to general formula (I), or of a pharmaceutically acceptable salt of said compound as described above, in combination with a pharmaceutically acceptable solvent or support.

A third subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use as a medicament.

A fourth subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use in the treatment of α-chemokine-mediated diseases.

A fifth subject according to the invention relates to a method for treating α-chemokine-mediated diseases using a compound corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof.

By way of examples of α-chemokine-mediated diseases, mention may be made of neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

The term "neutrophilic dermatosis" is intended to mean, in its broadest sense, Sweet's syndrome, "eccrine hydradenitis", SAPHO syndrome, Sneddon Wilkinson syndrome, pyoderma gangrenosum, erythema elevatum duitinum, psoriasis, common psoriasis, pustular psoriasis, palmoplantar pustulosis, exanthematous pustulosis (AGEP), pustulosis with vasculitis, acropustulosis of infancy, Behcet's disease, and also certain bullous diseases such as herpes derived in the form of dermatitis, neutrophilic IgA dermatosis, intraepidermal IgA pustulosis, bullous pemphigoid, IgA pemphigus, vasculitis, Leroy Reiter Fiellinger syndrome, pustulosis of the scalp, acrodermatitis continua of Hallopeau and dermatosis related to angioimmunoblastic lymphadenopathy, with cyclophosphamide-induced dysmyelopoiesis, with p-ANCA antibodies.

In one preferred embodiment according to the invention, the compound or the pharmaceutical composition mentioned above is used in the treatment of skin diseases such as neutrophilic dermatosis, in particular psoriasis, atopic dermatitis, acne and rosacea.

Another aspect of the invention relates to the use of a compound corresponding to general formula (I), and also the pharmaceutically acceptable salts, solvates or hydrates thereof, or else the use of a pharmaceutical composition comprising an effective amount of a compound corresponding to general formula (I), or of one of the pharmaceutically acceptable salts thereof or one of the pharmaceutically acceptable solvates or hydrates thereof, for preparing a medicament for the treatment of diseases of the group comprising neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease and skin cancers.

The compounds of general formula (I) of the present invention are prepared according to one or more of the synthesis routes as described below or as they emerge from the various preparation examples given hereinafter in a nonlimiting manner.

The general synthesis route for preparing the compounds of formula (III) is illustrated in FIG. 1. Sequential treatment of the alkyl squarate intermediates (A) with the amines R'2-NH2 and R'3-NH2 gives the compounds of formula (III). In formula (A), R'1 is a C1-C6 alkyl, preferably methyl or ethyl. The reaction is carried out in an inert and polar solvent (or in a mixture of solvents), such as ethanol, methanol, dimethyl sulfoxide, dimethylformamide or acetonitrile. The amines R'2-NH2 and R'3-NH2 can be used as free bases or in salt form. The reactions can be carried out in the presence of a suitable base, such as triethylamine, diisopropylethylamine, sodium carbonate or potassium carbonate and at 25° C. or preferably at high temperatures of 50-80° C. The reaction time is generally between 1 hour and 72 hours so as to have complete conversion.

Figure 2:
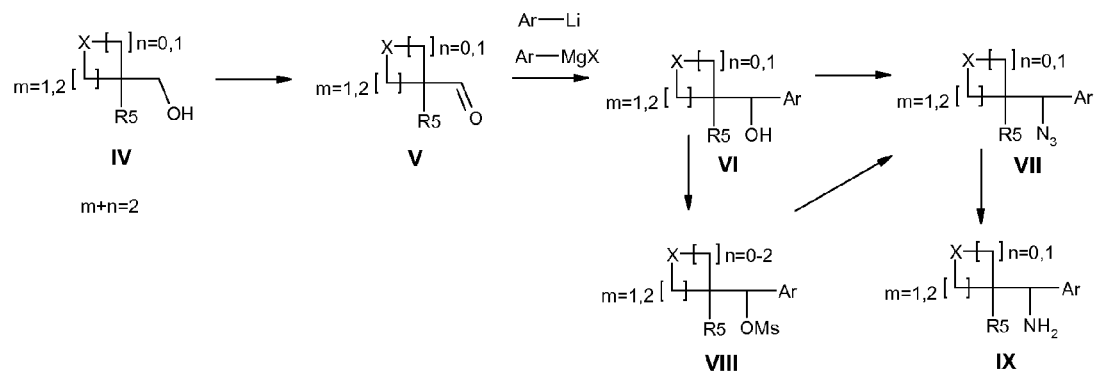

The amines R'3-NH2 of formula (IX) are prepared according to FIG. 2 from commercial reagents using methods well known to those skilled in the art, described in the organic synthesis manuals, for instance "Comprehensive Organic Functional Group Transformation" Vol. 1-7 A. R. Katritzky, O. Meth-Cohn, C. W. Rees, Pergamon Press, 1998.

The primary alcohols (IV) [in which X and R have the same meaning as X and R5 respectively defined above for the compounds of general formula (I)] are oxidized to aldehydes of formula (V) under the conditions of Swern (Mancuso, A. J.; Huang, S.-L.; Swern, D. (1978). "Oxidation of long-chain and related alcohols to carbonyls by dimethyl sulfoxide "activated" by oxalyl chloride" *J. Org. Chem.* 43 (12), 2480-2482) or with pyridinium chlorochromate.

The aldehyde of formula (V) is successively treated with an aryl or heteroaryl Grignard reagent or with a lithiated derivative to give a secondary alcohol of formula (VI). The corresponding azides (VII) are prepared from the alcohols (VI) either by converting them into mesylates (VIII) which are subsequently treated with metal azides (for example sodium azide), or by converting them directly into azide after treatment with diphenylphosphoryl azide (DPPA). The azide (VII) is finally reduced to the corresponding amine (IX) with hydrogen in the presence of various catalysts (for example, palladium on activated carbon) or by treatment with triphenylphosphine followed by hydrolysis of the imidophosphorane intermediates (Gololobov, Y. G. (1981), "Sixty years of staudinger reaction", *Tetrahedron* 37 (3), 437).

Figure 3:
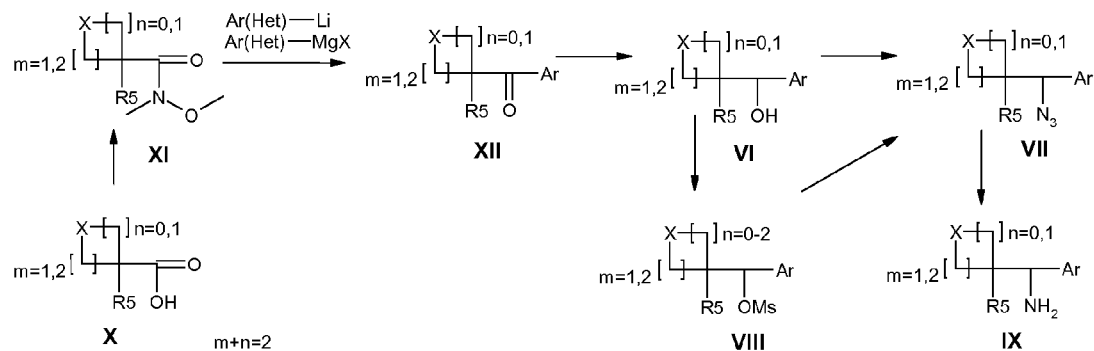

Alternatively, the primary amines R'3-NH2 of formula (IX) can be prepared according to FIG. 3 from commercial acids (X) [in which X and R have the same meaning as X and R5 respectively defined above for the compounds of general formula (I)], by converting them to Weinreb amides (XI) (Nahm, S.; Weinreb, S. M. (1981), "N-methoxy-n-methylamides as effective acylating agents", Tetrahedron Letters 22, 3815), which, after reaction with aryl or heteroaryl Grignard reagents or with lithiated aryl or heteroaryl derivatives give the ketones (XII) which can be reduced to secondary alcohols (VI).

By following the steps described in FIG. 2, the alcohol (VI) is optionally converted to the amine R'3-NH2 of formula (IX).

Figure 4:
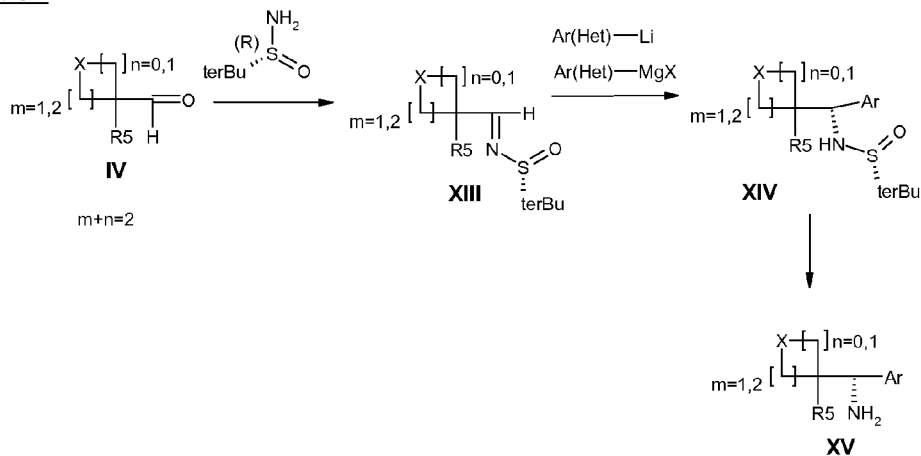

The chiral primary amine R'3-NH2 having the structure (XV) can also be prepared according to FIG. 4 by condensation of enantiomerically pure 2-methyl-2-propanesulfinamide (tert-butanesulfinamide, Elman's sulfinamide: Liu, G. et al. J. Am. Soc. Chem. 1997, 119, 9913) with the aldehyde (IV) under mild conditions. This reaction gives the tert-butanesulfinylimines (XIII). The tert-butanesulfinyl group activates the imines for the addition of the Grignard reagents and serves as an important chiral directing group for giving the products (XIV) with high diastereoselectivity. Deprotection of the tert-butanesulfinyl group under mild acidic conditions gives the chiral amine (XV).

Figure 5:
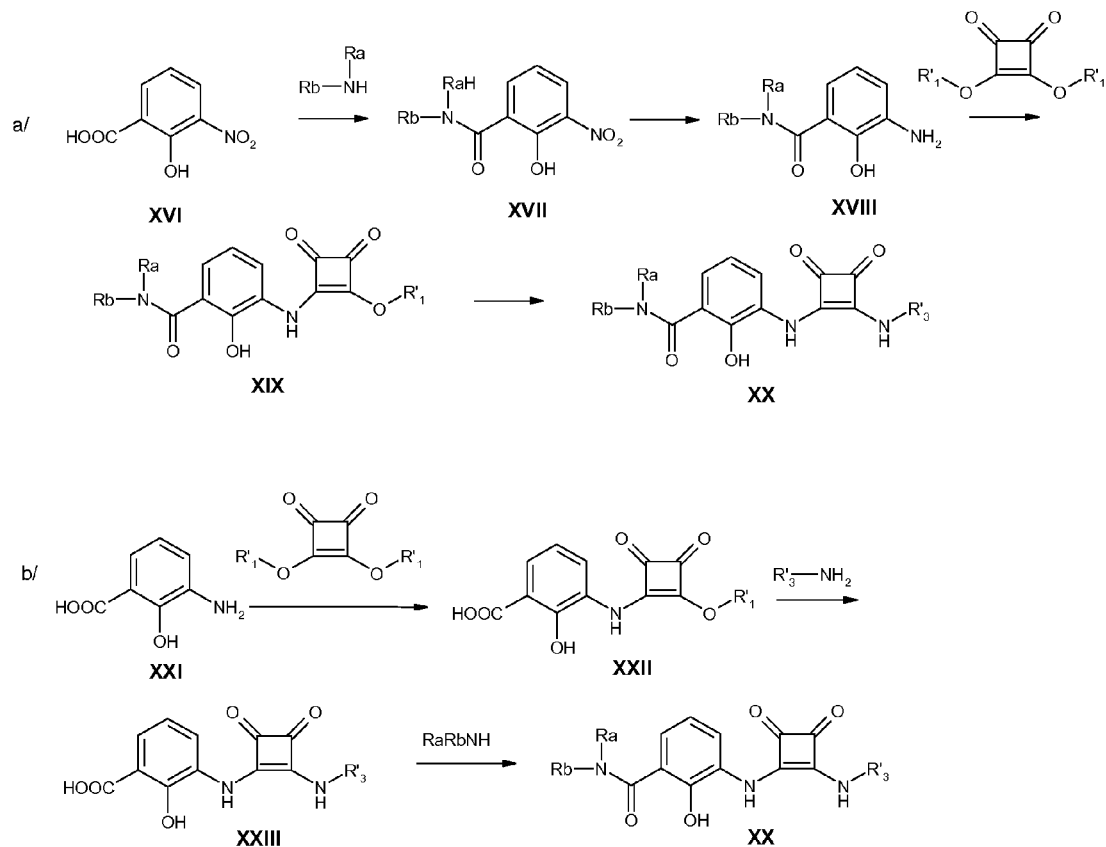

The amide derivatives of 3-aminosalicylic acid of formula (XVIII) are prepared according to FIG. 5a/ from 3-nitrosalicylic acid (XVI) using standard peptide coupling conditions (Recent development of peptide coupling reagents in organic synthesis Tetrahedron, Volume 60(11), 2447-2467, Han, S.-Y.; Kim, Y.-A.), followed by a reduction of the nitro group to an amino group with hydrogen in the presence of an appropriate catalyst (for example, palladium on activated carbon).

The derivative (XVIII) then reacts with the commercial dimethoxysquarate or diethoxysquarate to give the intermediate (XIX), which is converted to compound (XX) after reaction with the primary amine R'3-NH2.

Alternatively, the coupling of the 3-aminosalicylic acid (XXI) with the commercial dimethoxysquarate or diethoxysquarate gives, according to FIG. 5b/, the intermediate acid derivative (XXII) which, after reaction with the primary amine R'3-NH2, can give the compound (XXIII). The latter can, finally, be used in a peptide coupling reaction with an amine of formula RaRbNH to give the compound of formula (XX).

By way of illustration, the following compounds corresponding to general formula (I) of the present invention were prepared according to one of the figures presented above.

EXAMPLE 1

Preparation of 2-hydroxy-N,N-dimethyl-3-(2-{[(5-methylfuran-2-yl)-(3-methyloxetan-3-yl)methyl]amino}-3,4-dioxocyclobut-1-enylamino)benzamide

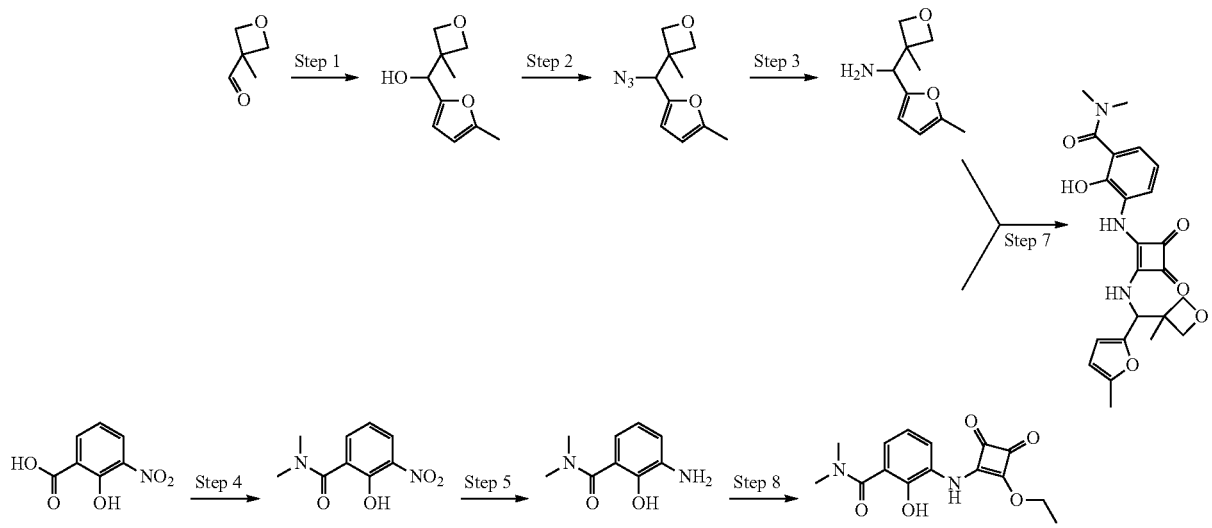

Step 1

(5-Methylfuran-2-yl)(3-methyloxetan-3-yl)methanol 12.0 ml (30 mmol, 1.7 eq) of a 2.5 M solution of n-butyllithium in hexane were added dropwise to a solution of 2.46 g (30 mmol, 1.7 eq) of 2-methylfuran in 50 ml of tetrahydrofuran cooled to −70° C. The reaction medium was stirred and allowed to return to ambient temperature for 3 hours. The reaction medium was cooled to −70° C. and then 2.17 g (18 mmol, 1 eq) of 3-methyloxetane-3-carbaldehyde at 83% were added. The reaction medium was stirred at ambient temperature for 3 hours. The reaction medium was treated with a saturated ammonium chloride solution and extracted with ethyl acetate. The organic phases were combined, washed with a saturated sodium chloride solution and evaporated. 3.02 g of (5-methylfuran-2-yl)-(3-methyloxetan-3-yl)methanol were obtained in the form of an orange oil. Yield=92%.

Step 2

2-[Azido-(3-methyloxetan-3-yl)methyl]-5-methylfuran 5.30 g (19 mmol, 1.1 eq) of diphenylphosphoryl azide were added dropwise to a solution of 3.02 g (17 mmol, 1 eq) of (5-methylfuran-2-yl)-(3-methyloxetan-3-yl)methanol in 50 ml of toluene. The reaction medium was cooled to 0° C. and then 2.9 ml (19 mmol, 1.1 eq) of 1,8-diazabicyclo[5.4.0]undec-7-ene were added dropwise. The reaction medium was stirred at ambient temperature for 23 hours. The reaction medium was separated by settling out and the organic phase was washed with water and then with 1 N hydrochloric acid, dried over magnesium sulfate, filtered and evaporated. The residue was chromatographed on silica gel (column Analogix SF40-150 g, Spot II) eluted with heptane/ethyl acetate (95/5). 1.68 g of 2-[azido-(3-methyloxetan-3-yl)methyl]-5-methylfuran were obtained in the form of an orange oil. Yield=48%.

Step 3

C-(5-Methylfuran-2-yl)-C-(3-methyloxetan-3-yl)methylamine

A solution of 1.68 g (8 mmol, 1 eq) of 2-[azido-(3-methyloxetan-3-yl)methyl]-5-methylfuran in 30 ml of ethanol in the presence of 252 mg (15% by weight) of palladium on carbon at 10% was stirred at hydrogen atmospheric pressure for 3 hours. The reaction medium was filtered and the filtrate was evaporated. 1.42 g of C-(5-methylfuran-2-yl)-C-(3-methyloxetan-3-yl)methylamine were obtained in the form of a greenish oil. Yield=98%.

Step 4

2-Hydroxy-N,N-dimethyl-3-nitrobenzamide 42.9 ml (0.50 mol, 3 eq) of oxalyl chloride were added dropwise to a suspension of 30 g (0.16 mol, 1 eq) of 3-nitrosalicylic acid in 1200 ml of dichloromethane. 30 drops of N,N-dimethylformamide were added (large amount of gas given off, adaptation of a system for trapping toxic carbon monoxide vapors). The reaction medium was stirred at ambient temperature for 24 hours. The reaction medium was cooled to 0-5° C. and then 246 ml (0.49 mol, 3 eq) of a 2 N solution of dimethylamine in tetrahydrofuran were added The reaction medium was stirred at ambient temperature for 2 days. The reaction medium was concentrated to dryness and the residue was dissolved in 300 ml 1 N sodium hydroxide. The aqueous solution (red) was extracted 3 times with 300 ml of dichloromethane. The aqueous phase was cooled in a water-ice bath, and the pH was adjusted to 2 with approximately 50 ml of 6 N hydrochloric acid. The mixture (which had become yellow) was extracted 3 times with 300 ml of dichloromethane. The organic phases were combined, washed twice with 250 ml of water and then once with 250 ml of a saturated sodium chloride solution, dried over anhydrous magnesium sulfate and evaporated. 33.5 g of 2-hydroxy-N,N-dimethyl-3-nitrobenzamide were obtained in the form of a cottony yellow solid. Yield=97%.

Step 5

3-Amino-2-hydroxy-N,N-dimethylbenzamide

A solution of 33.5 g of 2-hydroxy-N,N-dimethyl-3-nitrobenzamide in 600 ml of ethanol were added to a suspension of 3.35 g of Pd/C 10% in 70 ml of ethanol. The reaction medium was stirred under 2 bar of hydrogen overnight. TLC and HPLC control (t=0.66 M+181). The reaction medium was filtered through celite and the filtrate was evaporated. 29 g of 3-amino-2-hydroxy-N,N-dimethylbenzamide were obtained in the form of an oily brown solid. Yield=100%.

Step 6

3-(2-Ethoxy-3,4-dioxocyclobut-1-enylamino)-2-hydroxy-N,N-dimethylbenzamide

Under nitrogen and at ambient temperature, 39.7 g of diethoxysquarate were added (over the course of 15 minutes) to a solution of 28 g of 3-amino-2-hydroxy-N,N-dimethylbenzamide in 840 ml of ethanol cooled to 0° C. The reaction medium was stirred for 2 hours at 0° C. and 48 hours at ambient temperature. 700 ml of ethanol were added (which increases the precipitation of the expected product). The solid was filtered off, washed with ambient ethanol and dried. 36.9 g of (2-ethoxy-3,4-dioxocyclobut-1-enylamino)-2-hydroxy-N,N-dimethylbenzamide were obtained in the form of a light khaki green solid. Yield=78%.

Step 7

2-Hydroxy-N,N-dimethyl-3-(2{[(5-methylfuran-2-yl)-(3-methyloxetan-3-yl)methyl]amino}-3,4-dioxocyclobut-1-enylamino)benzamide 1.42 g (7.8 mmol, 2 eq) of C-(5-methylfuran-2-yl)-C-(3-methyloxetan-3-yl)methylamine were added to 1.19 g (3.9 mmol, 1 eq) of 3-(2-ethoxy-3,4-dioxocyclobut-1-enylamino)-2-hydroxy-N,N-dimethylbenzamide dissolved under hot conditions in 100 ml of methanol. The reaction medium was stirred at ambient temperature for 22 hours (75% of product formed after 6 hours). The methanol was evaporated off and the residue (green oil) was chromatographed on silica gel (column Analogix SF40-150 g, Spot II) eluted with 98/2 dichloromethane/methanol. The amorphous solid was taken up with diethyl ether, filtered and dried under vacuum at 45° C.

1.51 g of 2-hydroxy-N,N-dimethyl-3-(2-{[(5-methylfuran-2-yl)-(3-methyloxetan-3-yl)methyl]amino}-3,4-dioxocyclobut-1-enylamino)benzamide were obtained in the form of a yellow solid. Yield=88%. (Mp=196-198° C.); LC/MS: 98.69% [439].

$^1$H NMR (DMSO-d6, 400 MHz): 1.32 (s, 3H); 2.26 (s, 3H); 2.94 (s, 6H); 4.29 (dd, J=6.2 Hz, 2H); 4.6 (dd, J=28.8 Hz, 2H); 5.6 (d, J=9.7 Hz, 1H); 6.06 (d, J=2.1 Hz, 1H); 6.25 (d, J=3.1

Hz, 1H); 6.88 (dd, J=11.2 Hz, 2H); 7.76 (q, J=9.3 Hz, 1H); 8.83 (d, J=9.7 Hz, 1H); 9.45 (s, 1H).

EXAMPLE 2

3-(2-{[(3-fluoromethyloxetan-3-yl)-(5-methyl-furan-2-yl)methyl}amino]-3,4-dioxocyclobut-1-eny-lamino)-2-hydroxy-N,N-dimethylbenzamide

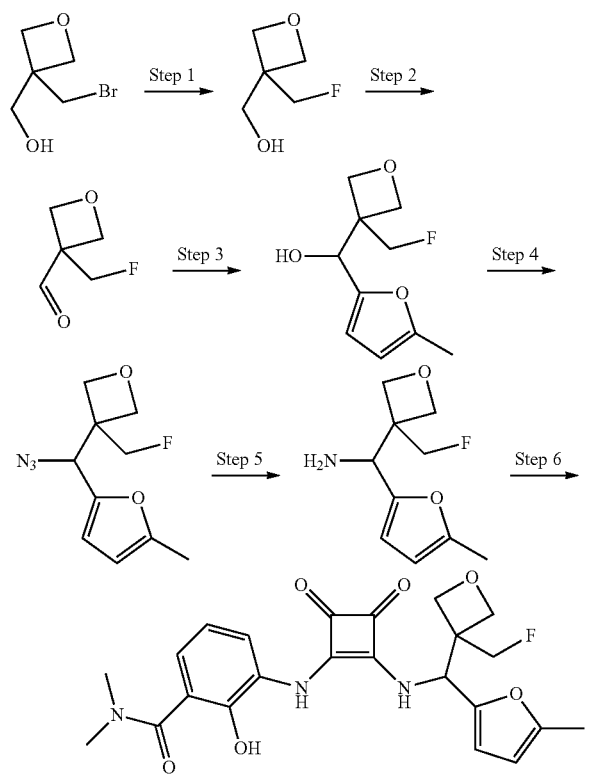

Step 1

(3-Fluoromethyloxetan-3-yl)methanol

A mixture of 21.5 g (0.119 mol, 1 eq) of 3-bromomethyl-3-hydroxymethyloxetane and 27.7 g (0.476 mol, 4 eq) of potassium fluoride in 60 ml of diethylene glycol was heated at 150° C. for 3 hours. The reaction medium was diluted with 120 ml of water and extracted with diethyl ether (18×30 ml) and then with ethyl acetate (8×50 ml). The organic phases were combined, dried over magnesium sulfate and evaporated. The residue was chromatographed on silica gel (column SuperFlash SF40-240 g) eluted with 30/70 heptane/ethyl acetate (elimination of the diethylene glycol). 10.55 g of (3-fluoromethyloxetan-3-yl)methanol were recovered in the form of a colorless oil. Yield=74%. TLC $SiO_2$/Heptane: EtOAc (20/80), developing with $KMnO_4$.

Step 2

3-Fluoromethyloxetane-3-carbaldehyde

A solution of 5.3 g (44 mmol, 1 eq) of (3-fluoromethyloxetan-3-yl)methanol in 50 ml of dichloromethane was added dropwise to a mixture of 15.2 g (70 mmol, 1.6 eq) of pyridinium chlorochromate in 220 ml of dichloromethane. 5.3 g of celite were added and the reaction medium was stirred at ambient temperature for 7 hours. The reaction medium was filtered on 75 g of silica and eluted with dichloromethane. 2.16 g of 3-fluoromethyloxetane-3-carbaldehyde were obtained in the form of a yellowish liquid. Yield=42% (presence of ~9% dichloromethane). TLC $SiO_2$/$CH_2Cl_2$:MeOH (96/4), developing with $KMnO_4$.

Step 3

(3-Fluoromethyloxetan-3-yl)-(5-methylfuran-2-yl)methanol 11.0 ml (27 mmol, 1.5 eq) of a 2.5 M solution of n-butyl-lithium in hexane were added dropwise to a solution of 2.25 g (27 mmol, 1.5 eq) of 2-methylfuran in 40 ml of tetrahydrofuran cooled to −70° C. The reaction medium was stirred and allowed to return to ambient temperature for 3 hours. The reaction medium was cooled to −70° C. and then 2.16 g (18 mmol, 1 eq) of 3-fluoromethyloxetane-3-carbaldehyde were added. The reaction medium was stirred at ambient temperature for two and a half hours. The reaction medium was treated with a saturated ammonium chloride solution and extracted with ethyl acetate. The organic phases were combined, washed with a saturated sodium chloride solution and evaporated. 3.83 g of (3-fluoromethyloxetan-3-yl)-(5-methylfuran-2-yl)methanol were obtained in the form of a dark orange oil. Yield=71%. TLC $SiO_2$/$CH_2Cl_2$:MeOH (96/4), developing with $KMnO_4$.

Step 4

2-[Azido-(3-fluoromethyloxetan-3-yl)methyl]-5-methylfuran 5.80 g (21 mmol, 1.1 eq) of diphenylphosphoryl azide were added dropwise to a solution of 3.83 g (19 mmol, 1 eq) of (3-fluoromethyloxetan-3-yl)-(5-methylfuran-2-yl)methanol in 50 ml of toluene. The reaction medium was cooled to 0° C. and then 3.15 ml (21 mmol, 1.1 eq) of 1,8-diazabicyclo[5.4.0]undec-7-ene were added dropwise. The reaction medium was stirred at ambient temperature for 15 hours. The (heterogeneous) reaction medium was treated with water and with ethyl acetate and then separated by settling out. The organic phase was washed with 1 N hydrochloric acid, dried over magnesium sulfate, filtered and evaporated. The residue was chromatographed on silica gel (column puriFlash IR-50SI/200G, Spot II) eluted with heptane/ethyl acetate (91/9). 2.25 g of 2-[azido-(3-fluoromethyloxetan-3-yl)methyl]-5-methylfuran were obtained in the form of a yellow oil. Yield=53%. TLC $SiO_2$/Heptane:EtOAc (80/20), developing with $KMnO_4$.

Step 5

C-(5-Methylfuran-2-yl)-C-(3-fluoromethyloxetan-3-yl)methylamine

A solution of 2.25 g (10 mmol, 1 eq) of 2-[azido-(3-fluoromethyloxetan-3-yl)methyl]-5-methylfuran in 40 ml of ethanol in the presence of 378 mg (17% by weight) of palladium on carbon at 10% was stirred at hydrogen atmospheric pressure for two and a half hours. The reaction medium was filtered and the filtrate was evaporated. 2.0 g of C-(5-methyl-furan-2-yl)-C-(3-fluoromethyloxetan-3-yl)methylamine were obtained in the form of a grayish oil. Yield=100%. TLC SiO$_2$/Heptane:EtOAc (70/30), developing with KMnO$_4$.

Step 6

3-(2-{[(3-Fluoromethyloxetan-3-yl)-(5-methyl-furan-2-yl)methyl]amino}-3,4-dioxocyclobut-1-enylamino)-2-hydroxy-N,N-dimethylbenzamide 1.50 g (7.5 mmol, 1.5 eq) of C-(5-methylfuran-2-yl)-C-(3-fluoromethyloxetan-3-yl)methylamine were added to 1.52 g (5.0 mmol, 1 eq) of 3-(2-ethoxy-3,4-dioxocyclobut-1-enylamino)-2-hydroxy-N,N-dimethylbenzamide dissolved under hot conditions in 100 ml of methanol. The reaction medium was heated at 50° C. for 16 hours and then at 60° C. for 6 hours. The methanol was evaporated off and the residue (green oil) was chromatographed on silica gel (column puri-Flash IR50SI-120G, Spot II) eluted with 98/2 dichloromethane/methanol. The amorphous solid was taken up with diethyl ether, filtered and dried under vacuum at 45° C.

1.85 g of 3-(2-{[(3-fluoromethyloxetan-3-yl)-(5-methylfuran-2-yl)methyl]amino}-3,4-dioxocyclobut-1-enylamino)-2-hydroxy-N,N-dimethylbenzamide were obtained in the form of a beige solid. (Mp=186-188° C.). Yield=81%. LC/MS: 100% [457].

$^1$H NMR (DMSO-d6, 400 MHz): 2.26 (s, 3H); 2.94 (s, 6H); 4.47 (t, 2H); 4.59-4.81 (m, 4H); 5.7 (d, J=9.7 Hz, 1H); 6.08 (d, J=2.1 Hz, 1H), 6.3 (d, J=3.0 Hz, 1H); 6.88 (m, 2H); 7.75 (q, J=9.5 Hz, 1H); 8.95 (d, J=12.6 Hz, 1H); 9.48 (s, 1H).

EXAMPLE 3

Preparation of 3-(2-{[(3-ethyloxetan-3-yl)-(5-methylfuran-2-yl)methyl]amino}-3,4-dioxocyclobut-1-enylamino)-2-hydroxy-N,N-dimethylbenzamide

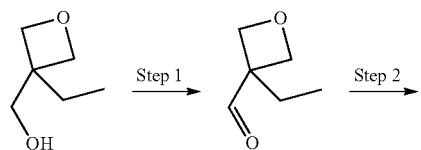

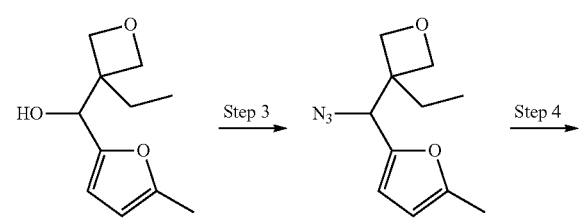

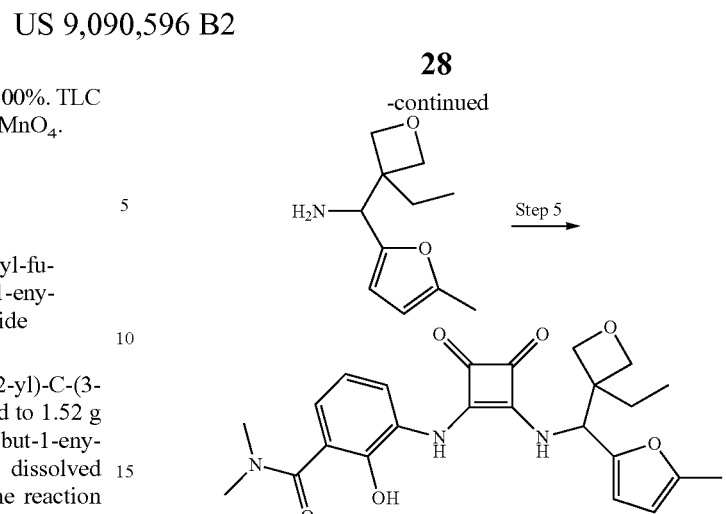

Step 1

3-Ethyloxetane-3-carbaldehyde

A solution of (3-ethyloxetan-3-yl)methanol (5.0 g, 43.0 mmol) in 60 ml of dichloromethane was added dropwise to a mixture of pyridinium chlorochromate (14.85 g, 68.9 mmol) and celite (4.30 g) in 200 ml of dichloromethane. The reaction medium was stirred at ambient temperature for 5 hours. The reaction medium was filtered on 70 g of silica and eluted with dichloromethane. The organic phases were combined and concentrated. 4.0 g of the expected product were obtained in the form of a pale green oil. Yield=82.3%.

Step 2

In a manner analogous to EXAMPLE 1 (step 1), (3-ethyloxetan-3-yl)-(5-methylfuran-2-yl)methanol was prepared. Yield=82%.

Step 3

In a manner analogous to EXAMPLE 1 (step 2), 2-[azido (3-ethyloxetan-3-yl)methyl]-5-methylfuran was prepared. Yield=53%.

Step 4

In a manner analogous to EXAMPLE 1 (step 3), C-(3-ethyloxetan-3-yl)-C-(5-methylfuran-2-yl)methylamine was prepared. Yield=94%.

Step 5

In a manner analogous to EXAMPLE 1 (step 7), 3-(2-{[(3-ethyloxetan-3-yl)-(5-methylfuran-2-yl)methyl]amino}-3,4-dioxocyclobut-1-enylamino)-2-hydroxy-N,N-dimethylbenzamide was prepared. Yield=66%, LC/MS: 97.0%, ES+ [454].

$^1$H NMR (DMSO-d6, 400 MHz): 0.95 (t, J=7.4 Hz, 3H); 1.43 (m, 1H); 1.79 (m, 1H); 2.26 (s, 3H); 2.94 (s, 6H); 4.34-4.40 (m, 2H); 4.55 (d, 1H); 4.74 (d, 1H); 5.55 (d, 1H); 6.06 (m,

1H); 6.27 (d, 1H); 6.87-6.92 (m, 2H); 7.75-7.78 (dm, 1H); 8.95 (d, 1H); 9.46 (s, 1H); 10.00 (s, 1H).

EXAMPLE 4

Preparation of 2-hydroxy-3-(2-{[(5-methylfuran-2-yl)-(3-methyloxetan-3-yl)methyl]amino}-3,4-dioxocyclobut-1-enylamino)benzoic acid

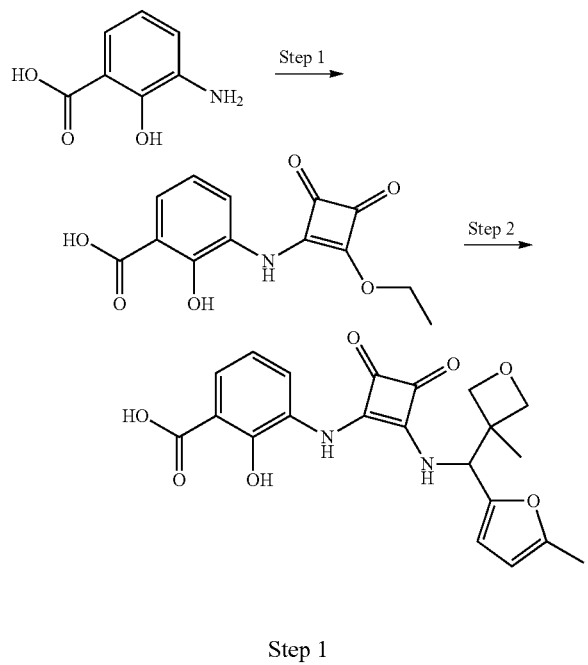

Step 1

3-(2-Ethoxy-3,4-dioxocyclobut-1-enylamino)-2-hydroxybenzoic acid

A mixture of 1.68 g (11 mmol, 1.1 eq) of 3-aminosalicylic acid and 1.70 g (10 mmol, 1 eq) of 3,4-diethoxy-3-cyclobutene-1,2-dione in 15 ml of ethanol was heated at 50° C. for three and a half hours, then at 60° C. for 20 hours (66% product formed) and at 70° C. for 4 hours (55% product formed). The reaction medium was filtered and the filtrate was chromatographed on silica gel (column puriFlash IR50SI-120G, Spot II) eluted with dichloromethane/methanol (gradient). The solid was taken up with a little ethyl acetate, filtered and dried under vacuum at 55° C. 1.04 g of 3-(2-ethoxy-3,4-dioxocyclobut-1-enylamino)-2-hydroxybenzoic acid were obtained in the form of a yellow-beige solid. Yield=38%.

Step 2

2-Hydroxy-3-(2{[(5-methylfuran-2-yl)-(3-methyloxetan-3-yl)methyl]amino}-3,4-dioxocyclobut-1-enylamino)benzoic acid 453 mg (2.5 mmol, 1.5 eq) of C-(5-methylfuran-2-yl)-C-(3-methyloxetan-3-yl)methylamine were added to 471 mg (1.7 mmol, 1 eq) of 3-(2-ethoxy-3,4-dioxocyclobut-1-enylamino)-2-hydroxybenzoic acid dissolved under hot conditions in 50 ml of methanol. The reaction medium was heated at 50° C. for 18 hours and then at 60° C. for 7 days. The methanol was evaporated off and the residue was chromatographed on silica gel (column puriFlash IR50SI-120G, Spot II) eluted with dichloromethane/methanol (gradient). The solid was taken up with a little ethyl acetate, filtered and dried under vacuum at 55° C. 310 mg of 2-hydroxy-3-(2-{[(5-methylfuran-2-yl)-(3-methyloxetan-3-yl)methyl]amino}-3,4-dioxocyclobut-1-enylamino)benzoic acid were obtained in the form of a brown solid. (Mp=180-185° C.). Yield=44%. LC/MS: 97.08% [412].

$^1$H NMR (DMSO-d6, 400 MHz): 1.32 (s, 3H); 2.26 (s, 3H); 4.29 (dd, J=6.2 Hz, 2H); 4.6 (dd, J=28.8 Hz, 2H); 5.66 (d, J=9.8 Hz, 1H); 6.06 (d, J=3.1 Hz, 1H), 6.24 (d, J=3.1 Hz, 1H); 6.46 (t, J=7.8 Hz, 1H); 7.33 (d, J=7.7 Hz, 1H); 7.79 (d, J=7.8 Hz, 1H); 8.90 (d, J=9.8 Hz, 1H); 9.46 (s, 1H).

EXAMPLE 5

Preparation of 3-[2-hydroxy-3-((R)-3-hydroxypyrrolidine-1-carbonyl)phenylamino]-4-{[(5-methylfuran-2-yl)-(3-methyloxetan-3-yl)methyl]amino}cyclobut-3-ene-1,2-dione

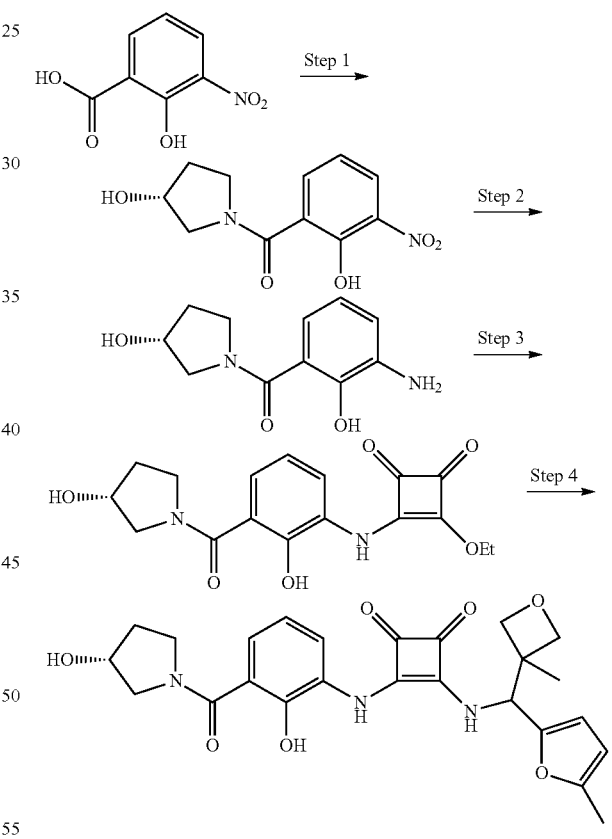

Step 1

(2-Hydroxy-3-nitrophenyl)-((R)-3-hydroxypyrrolidin-1-yl)methanone

A mixture of 4.86 g (26 mmol, 1 eq) of 3-nitrosalicylic acid and 12.16 g (26 mmol, 1 eq) of bromotripyrrolidinophosphonium hexafluorophosphate in 65 ml of dichloromethane and in the presence of 13.7 ml (78 mmol, 3 eq) of N,N-diisopropylethylamine was stirred at ambient temperature for 30 minutes. 4.52 g (4.10 mmol, 2 eq) of (R)-(+)-3-pyrrolidinol in solution in 10 ml of dichloromethane were added dropwise and the reaction medium was stirred at ambient temperature overnight. The reaction medium was extracted with a 1 N sodium hydroxide solution and separated by settling out. The aqueous phase was acidified with a 1N hydrochloric acid solution and extracted with ethyl acetate (5×150 ml). The organic phases were combined, dried over magnesium sulfate, filtered and evaporated. 7.83 g of (2-hydroxy-3-nitrophenyl)-((R)-3-hydroxypyrrolidin-1-yl)methanone were obtained in the form of a golden yellow amorphous solid. Crude yield>100%. HPLC: 93% [252].

Step 2

(3-Amino-2-hydroxyphenyl)-((R)-3-hydroxypyrrolidin-1-yl)methanone

A solution of 7.83 g (26 mmol, 1 eq) of (2-hydroxy-3-nitrophenyl)-((R)-3-hydroxypyrrolidin-1-yl)methanone at 84% in 100 ml of methanol was stirred at hydrogen atmospheric pressure in the presence of 728 mg (10% by weight) of palladium on carbon at 10% for 16 hours. The reaction medium was filtered and the filtrate was evaporated. The residue was chromatographed on silica gel (column puriFlash IR-50SI/300G, Spot II) eluted with dichloromethane/methanol (96/4). 3.63 g of (3-amino-2-hydroxyphenyl)-((R)-3-hydroxypyrrolidin-1-yl)methanone were obtained in the form of a yellow amorphous solid. Yield=63%. SiO$_2$/CH$_2$Cl$_2$ 90: MeOH 10, developing with KMnO$_4$.

Step 3

3-Ethoxy-4-[2-hydroxy-3-((R)-3-hydroxypyrrolidine-1-carbonyl)phenylamino]-cyclobut-3-ene-1,2-dione A mixture of 3.63 g (16 mmol, 1 eq) of (3-amino-2-hydroxyphenyl)-((R)-3-hydroxypyrrolidin-1-yl)methanone and 3.40 g (20 mmol, 1.2 eq) of 3,4-diethoxy-3-cyclobutene-1,2-dione in 70 ml of ethanol was heated at 60° C. for 16 hours. The reaction medium was filtered and the filtrate was chromatographed on silica gel (column puriFlash IR-50SI-300G, Spot II with solid deposition) eluted with dichloromethane/methanol (gradient). 3.67 g of 3-ethoxy-4-[2-hydroxy-3-((R)-3-hydroxypyrrolidine-1-carbonyl) phenylamino]cyclobut-3-ene-1,2-dione were obtained in the form of a beige solid. Yield=66%.

Step 4

3-[2-Hydroxy-3-((R)-3-hydroxypyrrolidine-1-carbonyl)phenylamino]-4-{[(5-methylfuran-2-yl)-(3-methyloxetan-3-yl)methyl]amino}cyclobut-3-ene-1,2-dione 544 mg (3 mmol, 1.5 eq) of C-(5-methylfuran-2-yl)-C-(3-methyloxetan-3-yl)methylamine were added to 693 mg (2 mmol, 1 eq) of 3-ethoxy-4-[2-hydroxy-3-((R)-3-hydroxypyrrolidine-1-carbonyl)phenylamino]cyclobut-3-ene-1,2-dione dissolved under hot conditions in 30 ml of methanol. The reaction medium was heated at 50° C. for 3 days and then at 60° C. for 5 hours. The methanol was evaporated off and the residue was chromatographed on silica gel (column puriFlash IR-50SI/80G, Spot II) then subsequently on silica gel (column puriFlash PF-15SIHP/25G×2, Spot II) eluted with dichloromethane/methanol (gradient). 694 mg of 3-[2-hydroxy-3-((R)-3-hydroxypyrrolidine-1-carbonyl)phenylamino]-4-{[(5-methylfuran-2-yl)-(3-methyloxetan-3-yl)methyl]amino}cyclobut-3-ene-1,2-dione were obtained in the form of an orange amorphous solid. Yield=72%. LC/MS: 99.6% [481].

$^1$H NMR (DMSO-d6, 400 MHz): 1.32 (s, 3H); 1.83-1.94 (m, 2H); 2.26 (s, 3H); 3.38 (m, 2H); 3.57 (m, 1H); 3.68 (m, 2H); 4.29 (dd, J=6.2 Hz, 2H); 4.6 (dd, J=29.2 Hz, 2H); 5.02 (s, 1H); 5.64 (d, J=9.7 Hz, 1H); 6.06 (dd, J=3.0 Hz, 1H); 6.26 (d, J=3.1 Hz, 1H); 6.90 (t, J=8.0 Hz, 1H); 7.16 (d, J=6.9 Hz, 1H); 7.85 (d, J=7.8 Hz, 1H); 8.85 (dd, J=9.7 Hz, 1H); 9.50 (s, 1H).

EXAMPLE 6

Preparation of 3-[2-hydroxy-3-((S)-3-hydroxypyrrolidine-1-carbonyl)phenylamino]-4-{[(5-methylfuran-2-yl)-(3-methyloxetan-3-yl)methyl]amino}cyclobut-3-ene-1,2-dione

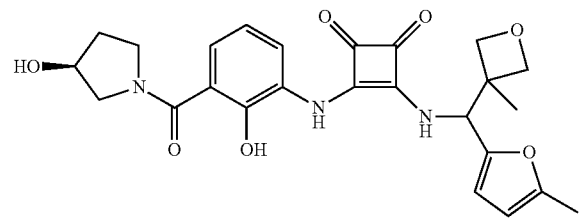 [SMILES: Cc1ccc(C(Nc2c(Nc3cccc(C(=O)N4CC[C@H](O)C4)c3O)c(=O)c2=O)C2(C)COC2)o1]

In a manner analogous to EXAMPLE 5 (steps 1 to 4), 3-[2-hydroxy-3-((S)-3-hydroxypyrrolidine-1-carbonyl)phenylamino]-4-{[(5-methylfuran-2-yl)-(3-methyloxetan-3-yl)methyl]amino}cyclobut-3-ene-1,2-dione was prepared. HPLC=98.87% (mixture of two diastereoisomers 53.84%+ 45.03%).

$^1$H NMR (methanol-d4, 400 MHz): 1.40 (s, 3H); 1.90-2.15 (m, 2H); 2.28 (s, 3H); 3.47-3.65 (m, 1H); 3.66-3.90 (m, 3H); 4.35-4.55 (m, 3H); 4.79 (d, J=6.3 Hz, 1H); 4.82-5.00 (m, 1H); 5.67 (s, 1H); 6.00 (dd, J=2.8 Hz, J=0.7 Hz, 1H); 6.23 (d, J=3.0 Hz, 1H); 6.92 (t, J=8.0 Hz, 1H); 7.15-7.25 (m, 1H); 8.05 (bd, J=7.9 Hz, 1H).

EXAMPLE 7

Preparation of (R)-1-[2-hydroxy-3-(2-{[(5-methylfuran-2-yl)-(3-methyloxetan-3-yl)methyl]amino}-3,4-dioxocyclobut-1-enylamino)benzoyl]pyrrolidine-2-carboxylic acid tert-butyl ester

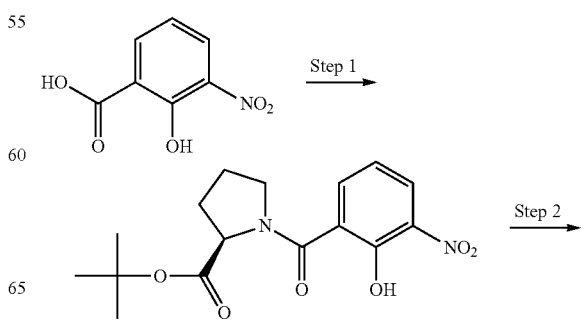

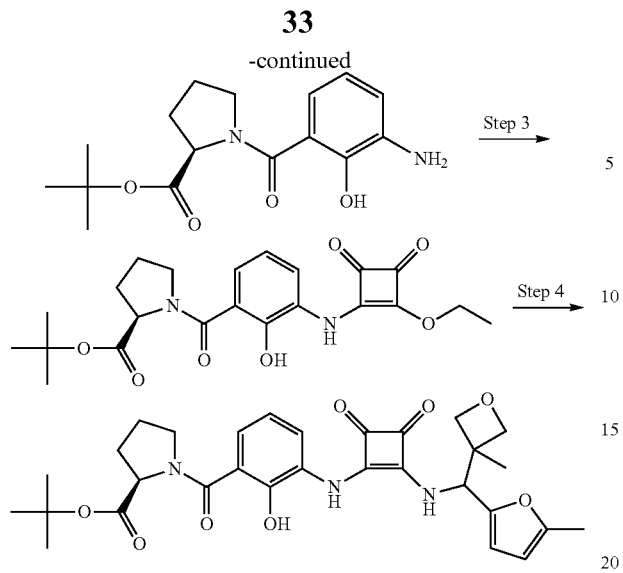

Step 1

In a manner analogous to EXAMPLE 5 (step 1), tert-butyl (R)-1-(2-hydroxy-3-nitrobenzoyl)pyrrolidine-2-carboxylate was prepared. Yield=68%.

Step 2

In a manner analogous to EXAMPLE 5 (step 2), tert-butyl (R)-1-(3-amino-2-hydroxybenzoyl)pyrrolidine-2-carboxylate was prepared. Yield=87%.

Step 3

In a manner analogous to EXAMPLE 5 (step 3), tert-butyl (R)-1-[3-(2-ethoxy-3,4-dioxocyclobut-1-enylamino)-2-hydroxy-benzoyl]pyrrolidine-2-carboxylate was prepared. Yield=66%.

Step 4 tert-Butyl (R)-1-[2-hydroxy-3-(2-{[(5-methylfuran-2-yl)-(3-methyloxetan-3-yl)methyl]amino}-3,4-dioxocyclobut-1-enylamino)benzoyl]pyrrolidine-2-carboxylate A mixture of 253 mg (1.44 mmol, 1.2 eq) of C-(5-methylfuran-2-yl)-C-(3-methyloxetan-3-yl)methylamine and 516 g (1.2 mmol, 1 eq) of (R)-1-[3-(2-ethoxy-3,4-dioxo-cyclobut-1-enylamino)-2-hydroxy-benzoyl]pyrrolidine-2-carboxylic acid tert-butyl ester in 10 ml of methanol was heated at 50° C. for 4 days. The reaction medium was evaporated and the residue was chromatographed on silica gel HP (column RediSep Rf Gold 40 g, Spot II) eluted with dichloromethane/methanol (gradient). The amorphous solid was taken up with a little diethyl ether, filtered and dried under vacuum at 50° C.

476 mg of tert-butyl (R)-1-[2-hydroxy-3-(2-{[(5-methylfuran-2-yl)-(3-methyloxetan-3-yl)methyl]amino}-3,4-dioxocyclobut-1-enylamino)benzoyl]pyrrolidine-2-carboxylate were obtained. (Mp=162-164° C.). Yield=70%. LC/MS: 98.7% [565]: presence of 2 diastereoisomers.

$^1$H NMR (DMSO-d6, 400 MHz): 1.20 (s, 3H); 1.32 (s, 3H); 1.42 (s, 6H); 1.89 (m, 3H); 2.24 (m, 1H); 2.26 (s, 3H); 3.61 (m, 2H); 4.29 (dd, J=6.0 Hz, 2H); 4.40 (s, 1H); 4.6 (dd, J=28.9 Hz, 2H); 5.64 (d, J=9.8 Hz, 1H); 6.06 (dd, J=3.0 Hz, 1H); 6.26 (d, J=3.0 Hz, 1H); 6.91-7.15 (m, 2H); 7.75-7.87 (m, 1H); 8.83 (d, J=9.8 Hz, 1H); 9.48 (s, 1H).

EXAMPLE 8

Preparation of methyl (R)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate

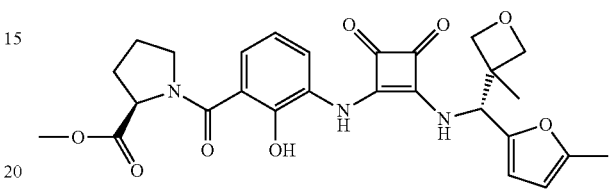

In a manner analogous to EXAMPLE 7 (steps 1 to 4), methyl (R)-1-[2-hydroxy-3-(2-{[(R)-(5-methylfuran-2-yl)-(3-methyloxetan-3-yl)-methyl]amino}-3,4-dioxocyclobut-1-enylamino)benzoyl]pyrrolidine-2-carboxylate was prepared.

Presence of two conformers, description of the major conformer at approximately 80%:

$^1$H NMR (DMSO-d6, 400 MHz) 1.32 (s, 3H), 1.80-2.00 (m, 3H), 2.15-2.35 (m, 4H), 3.55-3.75 (m, 5H), 4.27-4.30 (m, 2H), 4.50-4.60 (m, 2H), 4.65 (d, J=6.2 Hz, 1H), 5.64 (d, J=9.8 Hz, 1H), 6.06 (dd, J=3.1 Hz, J=1.0 Hz, 1H), 6.26 (d, J=3.1 Hz, 1H), 6.93 (t, J=7.9 Hz, 1H), 7.14 (bd, J=7.52 Hz, 1H), 7.86 (bd, J=7.8 Hz, 1H), 8.84 (bd, J=9.72 Hz, 1H), 9.49 (bs, 1H).

EXAMPLE 9

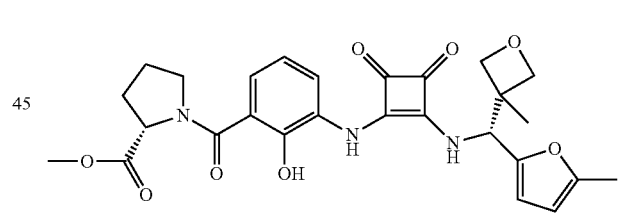

Preparation of methyl (S)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate In a manner analogous to EXAMPLE 7 (steps 1 to 4), methyl (S)-1-[2-hydroxy-3-(2-{[(R)-(5-methylfuran-2-yl)-(3-methyloxetan-3-yl)-methyl]amino}-3,4-dioxocyclobut-1-enylamino)benzoyl]pyrrolidine-2-carboxylate was prepared.

$^1$H NMR/DMSO-d6, 400 MHz 1.33 (s, 3H); 1.88-1.92 (m, 3H); 2.26-2.33 (m, 4H); 3.36-3.41 (m, 1H); 3.62-3.68 (m, 4H); 4.28-4.36 (m, 2H); 4.55-4.60 (m, 2H); 4.65 (d, j=6.2 Hz, 1H); 5.65 (d, j=9.7 Hz, 1H); 6.06 (m, 1H); 6.25 (d, j=3.0 Hz,

1H); 6.94 (d, j=6.7 Hz, 1H); 7.15 (d, j=7.5 Hz, 1H); 7.86 (d, j=7.4 Hz, 1H); 8.83 (d, j=9.7 Hz, 1H); 9.49 (s, 1H); 10.00-11.20 (m, 1H)

EXAMPLE 10

Preparation of (R)-1-[2-hydroxy-3-(2-{[(5-methylfuran-2-yl)-(3-methyloxetan-3-yl)methyl]amino}-3,4-dioxocyclobut1-enylamino)benzoyl]pyrrolidine-2-carboxylic acid

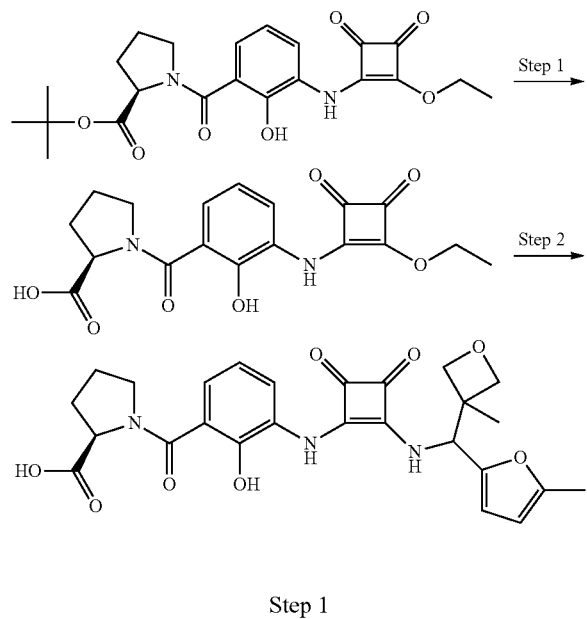

Step 1

(R)-1-[3-(2-Ethoxy-3,4-dioxocyclobut-1-enylamino)-2-hydroxybenzoyl]pyrrolidine-2-carboxylic acid 1.00 g (2.32 mmol) of tert-butyl (R)-1-[3-(2-ethoxy-3,4-dioxocyclobut-1-enylamino)-2-hydroxy-benzoyl]pyrrolidine-2-carboxylate were dissolved in 5 ml of trifluoroacetic acid. 25 min later, the reaction medium was concentrated to dryness and was taken up in toluene before being again concentrated. A pink foam was obtained. This foam was taken up with diethyl ether, with stirring, and then filtered. 0.75 g was obtained in the form of a beige solid. Yield=86%.

Step 2

(R)-1-[2-Hydroxy-3-(2-{[(5-methylfuran-2-yl)-(3-methyloxetan-3-yl)methyl]amino}-3,4-dioxocyclobut1-enylamino)benzoyl]pyrrolidine-2-carboxylic acid 494 mg (2.73 mmol) of C-(5-methylfuran-2-yl)-C-(3-methyloxetan-3-yl)methylamine in 3 ml of methanol were added to a solution of 500 mg (1.34 mmol) of (R)-1-[3-(2-ethoxy-3,4-dioxocyclobut-1-enylamino)-2-hydroxy-benzoyl]pyrrolidine-2-carboxylic acid in 47 ml of methanol at 50° C. After 3 days, 248 mg (1.37 mmol) of C-(5-methylfuran-2-yl)-C-(3-methyloxetan-3-yl)methylamine were added. After 4 days, the reaction medium was concentrated to dryness. The reaction medium was taken up in ethyl acetate and was washed with a saturated aqueous ammonium chloride solution and then with a 1 M aqueous solution of sodium dihydrogen phosphate. The organic phase was dried over magnesium sulfate, filtered and concentrated. The solid obtained was taken up, with stirring, in diethyl ether and a little ethyl acetate and was filtered. 400 mg of a beige solid were obtained. This solid was chromatographed on silica gel (ethyl acetate/acetone/water: 50/50/2 then 50/50/5). 240 mg were obtained in the form of a beige solid. Yield=35%, HPLC=52.43%+45.15% (mixture of the two diastereoisomers), Mp=198-205° C.

$^1$H NMR (DMSO-d6, 400 MHz): =1.32 (s, 3H); 1.75-1.95 (m, 3H); 2.18-2.26 (m, 4H); 3.40-3.51 (m, 2H); 4.27-4.44 (m, 1H); 4.58 (d, J=6.2 Hz, 1H); 4.65 (d, J=6.1 Hz, 1H); 5.66 (d, J=9.7 Hz, 1H); 6.05-6.06 (m, 1H); 6.25 (d, J=3.1 Hz, 1H); 6.80-6.88 (m, 1H); 7.01 (d, J=7.4 Hz, 1H); 7.80-7.85 (m, 1H); 8.92 (bd, J=9.4 Hz, 1H); 9.57 (s, 1H).

EXAMPLE 11

Preparation of 3-[2-hydroxy-3-(1-hydroxyethyl)phenylamino]-4-{[(5-methylfuran-2-yl)-(3-methyloxetan-3-yl)methyl]amino}cyclobut-3-ene-1,2-dione

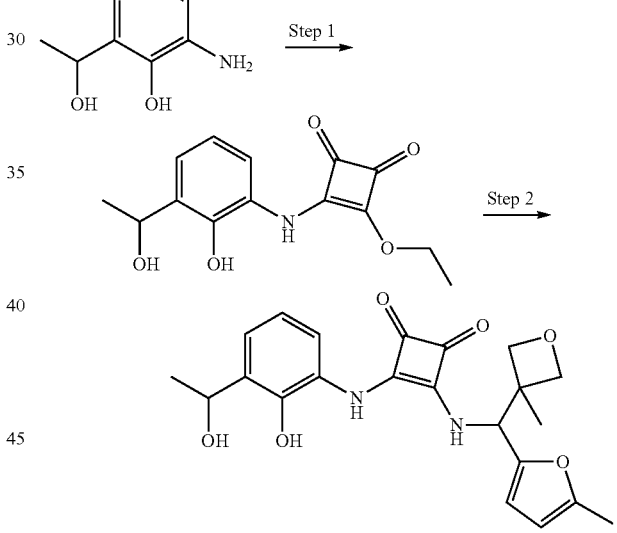

Step 1

3-Ethoxy-4-[2-hydroxy-3-(1-hydroxyethyl)phenylamino]cyclobut-3-ene-1,2-dione

A mixture of 1.16 g (7.6 mmol, 1 eq) of 2-amino-6-(1-hydroxyethyl)phenol and 5.15 g (30.3 mmol, 4 eq) of 3,4-diethoxy-3-cyclobutene-1,2-dione in 50 ml of ethanol was heated at 60° C. for 18 hours. The reaction medium was evaporated and the residue was chromatographed on silica gel (column puriFlash IR-50SI/300G, Spot II) eluted with heptane/ethyl acetate (gradient). 800 mg of 3-ethoxy-4-[2-hydroxy-3-(1-hydroxyethyl)phenylamino]cyclobut-3-ene-1,2-dione were obtained in the form of an orange solid. Yield=38%.

Step 2

3-[2-Hydroxy-3-(1-hydroxyethyl)phenylamino]-4-{[(5-methylfuran-2-yl)-(3-methyloxetan-3-yl)methyl]amino}cyclobut-3-ene-1,2-dione A mixture of 314 mg (1.73 mmol, 1.2 eq) of C-(5-methylfuran-2-yl)-C-(3-methyloxetan-3-yl)methylamine and 400 g (1.44 mmol, 1 eq) of 3-ethoxy-4-[2-hydroxy-3-(1-hydroxyethyl)phenylamino]cyclobut-3-ene-1,2-dione in 15 ml of methanol was heated at 50° C. for 2 days. The reaction medium was evaporated and the residue was chromatographed on silica gel HP (column RediSep Rf Gold 40 g, Spot II) eluted with dichloromethane/methanol (gradient). The amorphous solid was taken up with a little diethyl ether, filtered and dried under vacuum at 50° C. 151 mg of 3-[2-hydroxy-3-(1-hydroxyethyl)phenylamino]-4-{[(5-methylfuran-2-yl)-(3-methyloxetan-3-yl)methyl]amino}cyclobut-3-ene-1,2-dione were obtained in the form of an orange solid. (Mp=129-131° C.). Yield=25%. LC/MS: 96.1% [412]: 2 diastereoisomers.

$^1$H NMR (DMSO-d6, 400 MHz): 1.32 (s, 3H); 1.35 (d, J=6.4 Hz, 3H); 2.26 (s, 3H); 4.29 (dd, J=6.1 Hz, 2H); 4.6 (dd, J=29.9 Hz, 2H); 5.06 (q, J=6.3 Hz, 1H); 5.64 (d, J=9.7 Hz, 1H); 6.06 (d, J=2.0 Hz, 1H); 6.25 (d, J=3.0 Hz, 1H); 6.82 (t, J=7.9 Hz, 1H); 6.95 (d, J=7.6 Hz, 1H); 7.58 (d, J=7.8 Hz, 1H); 8.76 (d, J=9.8 Hz, 1H); 9.39 (s, 2H).

EXAMPLE 12

Preparation of 3-(2-hydroxy-3-isobutyrylphenylamino)-4-{[(5-methylfuran-2-yl)-(3-methyloxetan-3-yl)methyl]amino}cyclobut-3-ene-1,2-dione

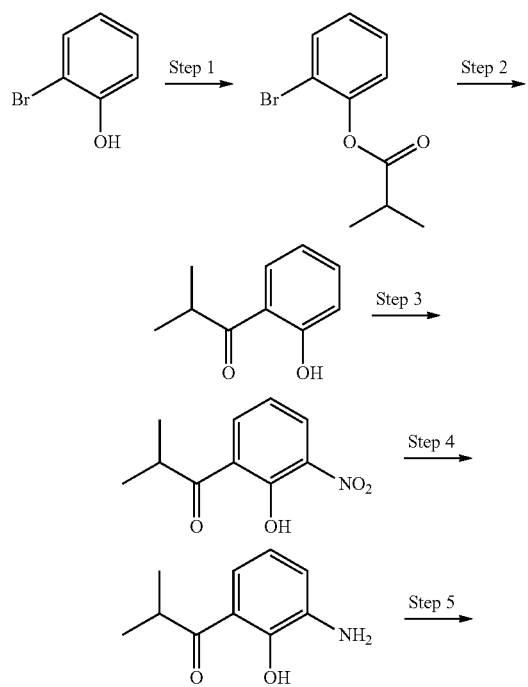

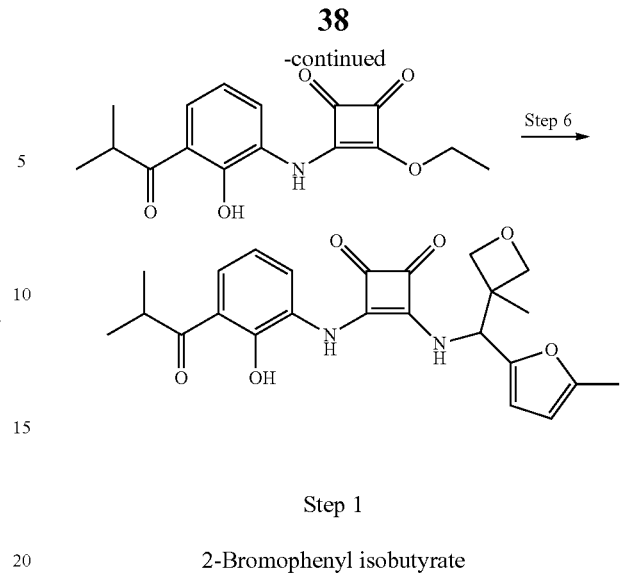

Step 1

2-Bromophenyl isobutyrate 25 g (145 mmol) of 2-bromophenol in 100 ml of tetrahydrofuran were added dropwise to a suspension of 6.40 g (160 mmol) of sodium hydride (60% in oil) in 150 ml of tetrahydrofuran at 0° C. under nitrogen. 15 minutes later, 26.5 ml (160 mmol) were added dropwise; the reaction medium sets solid, 100 ml of tetrahydrofuran were then added. One hour later, the reaction medium was hydrolyzed with water and a saturated aqueous sodium hydrogen carbonate solution was added, as was ethyl acetate (presence of a precipitate in the aqueous phase, definitely salts). The organic phase was then washed with water, dried over anhydrous magnesium sulfate, filtered and concentrated. 34.75 g of a colorless oil were obtained and filtered on silica (100% heptane then approximately 90/10 heptane/ethyl acetate). 31.59 g were obtained in the form of a colorless oil. Yield=90% (presence of isobutyric anhydride in $^1$H NMR).

Step 2

1-(2-Hydroxyphenyl)-2-methylpropan-1-one 100 ml of sec-butyllithium at 1.4 M in cyclohexane were added dropwise to a solution of 31.59 g (130 mmol) of 2-bromophenyl isobutyrate in 300 ml of tetrahydrofuran at −85° C. under nitrogen. The reaction medium was maintained for 30 minutes at approximately −75° C. and was then left to gently return to ambient temperature. After 2 hours, a little ethyl acetate was added, followed by approximately 400 ml of a 1 M aqueous sodium dihydrogen carbonate solution. The organic phase was recovered, washed with water, dried over anhydrous magnesium sulfate, filtered and concentrated. 23.97 g of an orange oil were obtained and purified on silica cake. The residue obtained was chromatographed on a prepacked silica column (eluent heptane/ethyl acetate). 4.3 g of product were obtained in the form of a yellow oil. Yield=20%.

Step 3

1-(2-Hydroxy-3-nitrophenyl)-2-methylpropan-1-one 1.6 ml of fuming nitric acid were added, over the course of 20 minutes, to a solution of 4.1 g of 1-(2-hydroxyphenyl)-2-methylpropan-1-one in 25 ml of acetic acid cooled to 5° C. The reaction medium was stirred at ambient temperature for 5 hours (followed by TLC, 10/1 heptane/ethyl acetate). The reaction was stopped before all the 1-(2-hydroxyphenyl)-2- methylpropan-1-one was consumed. The reaction medium was diluted with 70 ml of water and then extracted with ethyl acetate (4:1, 3×50 ml). The organic phases were combined, washed with water (20 ml) and then with a saturated sodium chloride solution (25 ml), and dried over magnesium sulfate. The solvent was evaporated off and the residue was chromatographed on silica. 1.40 g of 1-(2-hydroxy-5-nitrophenyl)-2-methylpropan-1-one and 1.2 g of 1-(2-hydroxy-3-nitrophenyl)-2-methylpropan-1-one were obtained.

Step 4

1-(3-Amino-2-hydroxyphenyl)-2-methylpropan-1-one

A solution of 1.04 g of (2-hydroxy-5-nitrophenyl)-2-methylpropan-1-one in 20 ml of ethanol and in the presence of 200 mg (20% by weight) of palladium on activated carbon at 10% was stirred at hydrogen atmospheric pressure overnight. At the end of the reaction, the alcohol derivative IV was also formed. The solvent was evaporated off and the residue was purified by chromatography on silica gel eluted with heptane/ethyl acetate (10/1). 390 mg of 1-(3-amino-2-hydroxyphenyl)-2-methylpropan-1-one were obtained in the form of a yellow oil (Yield=44%). 220 mg of 2-amino-6-(1-hydroxy-2-methylpropyl)phenol were obtained in the form of a beige solid (Yield=25%).

Step 5

3-Ethoxy-4-(2-hydroxy-3-isobutyrylphenylamino) cyclobut-3-ene-1,2-dione

A solution of 0.39 g (2.18 mmol, 1 eq) of 1-(3-amino-2-hydroxyphenyl)-2-methylpropan-1-one and 1.51 g (8.87 mmol, 4 eq) of 3,4-diethoxy-3-cyclobut-3-ene-1,2-dione in 4 ml of ethanol was heated at 60° C. for 24 hours. The reaction medium was concentrated. The residue (1.80 g) was chromatographed on silica gel (120 g prepacked column, eluent heptane/ethyl acetate from 10% to 50% of ethyl acetate). 0.46 g of product were obtained in the form of a yellow oil. Yield=70%.

Step 6

3-Ethoxy-4-(2-hydroxy-3-isobutyrylphenylamino) cyclobut-3-ene-1,2-dione 551 mg (3.04 mmol, 2 eq) of C-(5-methylfuran-2-yl)-C-(3-methyloxetan-3-yl)methylamine in solution in 3 ml of methanol were added to a solution of 0.46 g (1.52 mmol, 1 eq) of 3-ethoxy-4-(2-hydroxy-3-isobutyrylphenylamino)cyclobut-3-ene-1,2-dione in 10 ml of methanol at 50° C. After 15 hours, a precipitate was formed and was filtered off. 0.49 g of product were obtained in the form of a yellow solid. Yield=73%, HPLC purity=96.75%, Mp=216-217° C.

$^1$H NMR (DMSO-d6, 400 MHz): =1.17 (d, J=6.8 Hz, 6H); 2.26 (s, 3H); 3.77 (sext, J=6.8 Hz, 1H); 4.28-4.31 (m, 2H); 4.57 (d, J=6.2 Hz, 1H); 4.65 (d, J=6.2 Hz, 1H); 5.64 (d, J=9.8 Hz, 1H); 6.06-6.07 (m, 1H); 6.26 (d, J=3.1 Hz, 1H); 7.00 (t, J=8.0 Hz, 1H); 7.72 (dd, J=8.3 Hz, J=1.0 Hz, 1H); 8.06 (dd, J=7.9 Hz, J=0.9 Hz, 1H); 8.86 (d, J=9.8 Hz, 1H); 9.57 (s, 1H); 13.00-13.20 (m, 1H).

EXAMPLE 13

Preparation of 3-(4-hydroxy-2-methyl-3-oxo-2,3-dihydro-1H-isoindol-5-ylamino)-4-{[(5-methylfuran-2-yl)-(3-methyloxetan-3-yl)methyl]amino}cyclobut-3-ene-1,2-dione

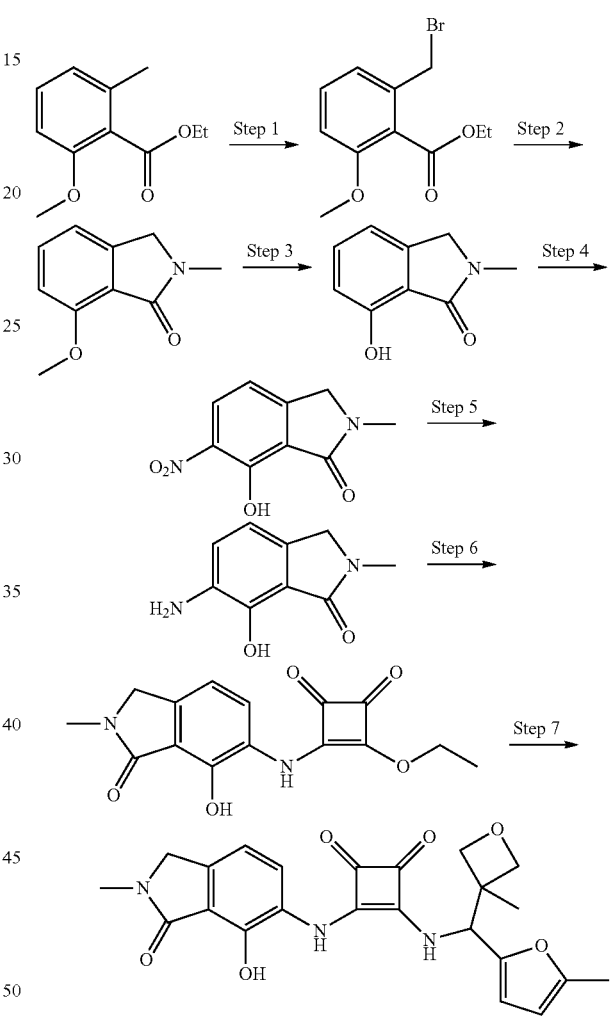

Step 1

Ethyl 2-bromomethyl-6-methoxybenzoate 19.56 g of N-bromosuccinimide and 4.84 g of benzoyl peroxide were added to a solution of 19.40 g of ethyl 2-methoxy-6-methylbenzoate in 150 ml of carbon tetrachloride. The reaction medium was refluxed for 6 hours (no further change). The reaction medium was cooled to 5° C. and the succinimide was filtered. The organic phase was washed with a saturated sodium hydrogen carbonate solution (2×150 ml), dried over magnesium sulfate and evaporated. The residue was purified by chromatography on silica gel (column puri-Flash, IR-50SI/800G, Spot II) eluted with heptane/ethyl acetate (gradient). 15.5 g of ethyl 2-bromomethyl-6-methoxybenzoate were obtained in the form of a yellow oil which later crystallizes. Yield=56%.

Step 2

7-Methoxy-2-methyl-2,3-dihydroisoindol-1-one

A solution of methylamine (2 M in methanol) at 0° C. was added dropwise to a solution of 14.82 g of ethyl 2-bromomethyl-6-methoxybenzoate in methanol and the reaction medium was stirred for 5 hours at 0° C. and left to stir at ambient temperature for 2 days. The solvent was evaporated off and 30 ml of a saturated sodium hydrogen carbonate solution were added to the residue. The product was extracted with ethyl acetate (3×50 ml). The organic phases were combined, dried over magnesium sulfate and evaporated. The residue was purified by chromatography on silica gel. 4.52 g of 7-methoxy-2-methyl-2,3-dihydroisoindol-1-one were obtained. Yield=47%.

Step 3

7-Hydroxy-2-methyl-2,3-dihydroisoindol-1-one 100 ml of a 1 M solution of boron tribromide in dichloromethane at −78° C. were added dropwise to a solution of 3.7 g of 7-methoxy-2-methyl-2,3-dihydroisoindol-1-one in 50 ml of dichloromethane. The reaction medium was stirred at −78° C. for 1 hour and then left to return to 0° C. for 1 hour. The reaction medium was cooled to −78° C. and then slowly hydrolyzed by adding, dropwise, 20 ml of methanol (temperature below −60° C.). The reaction medium was washed with 30 ml of a 1 M sodium dihydrogen phosphate solution and the aqueous phase was extracted with ethyl acetate (2×50 ml). The organic phases were combined, dried over magnesium sulfate and evaporated. The residue was triturated with diethyl ether. 2.6 g of 7-hydroxy-2-methyl-2,3-dihydroisoindol-1-one were obtained.

Step 4

7-Hydroxy-2-methyl-6-nitro-2,3-dihydroisoindol-1-one 2.49 g (91.5 mmol) of 7-hydroxy-2-methyl-2,3-dihydroisoindol-1-one were dissolved at 0° C. in 6 ml of concentrated sulfuric acid. The reaction medium was cooled to −20° C. and 1.8 ml of a 4/5 mixture of concentrated sulfuric acid/nitric acid at 70% were added. After 10 minutes, the reaction medium was hydrolyzed with water. Sodium chloride was added and the medium was extracted twice with ethyl acetate. The organic phases were combined, dried over anhydrous sodium sulfate and concentrated. The residue was chromatographed on a C18 column twice (40 g prepacked column, water/acetonitrile gradient). 350 mg of product were obtained in the form of a yellow solid. Yield=11%.

Step 5

6-Amino-7-hydroxy-2-methyl-2,3-dihydroisoindol-1-one 38 mg of palladium on carbon at 10% were added to a solution of 0.35 g (1.68 mmol) of 7-hydroxy-2-methyl-6-nitro-2,3-dihydroisoindol-1-one in 20 ml of methanol under nitrogen. The reaction medium was stirred under a hydrogen atmosphere for 18 hours. The reaction medium was filtered and concentrated. The residue was chromatographed on a prepacked C18 column (12 g column, 30 ml/min, 95/5 water/acetonitrile). 0.19 g of product was obtained in the form of a brown oil. Yield=64%.

Step 6

3-Ethoxy-4-(4-hydroxy-2-methyl-3-oxo-2,3-dihydro-1H-isoindol-5-ylamino)cyclobut-3-ene-1,2-dione A mixture of 0.19 g (1.07 mmol) of 6-amino-7-hydroxy-2-methyl-2,3-dihydroisoindol-1-one and 0.80 g (4.70 mmol) of 3,4-diethoxycyclobut-3-ene-1,2-dione in 10 ml of ethanol was heated at 60° C. for 24 hours. The reaction medium was concentrated and was taken up with diethyl ether with stirring (formation of a precipitate). The solid obtained was filtered off, washed twice with diethyl ether and dried. 235 mg of product were obtained. Yield=73%.

Step 7

3-(4-Hydroxy-2-methyl-3-oxo-2,3-dihydro-1H-isoindol-5-ylamino)-4-{[(5-methylfuran-2-yl)-(3-methyloxetan-3-yl)methyl]amino}cyclobut-3-ene-1,2-dione 287 mg (1.58 mmol) of C-(5-methylfuran-2-yl)-C-(3-methyloxetan-3-yl)methylamine in 3 ml of methanol were added to a suspension of 235 mg (0.78 mmol) of 3-(2-ethoxy-3,4-dioxocyclobut-1-enylamino)-2-hydroxy-N,N-dimethylbenzamide in 20 ml of methanol at 55° C. The reaction medium was heated at 55° C. for 24 hours and then concentrated to dryness. The residue was chromatographed on silica gel (40 g prepacked column, 30 ml/min, 100% dichloromethane then 4% of methanol). A residue of 130 mg was obtained and was purified by preparative TLC (eluent: 50/50/1 ethyl acetate/acetone/water). 52 mg were obtained and then precipitated from dimethyl sulfoxide and filtered off 15 mg of product were obtained in the form of a white solid. Yield=4%, HPLC=98.56%

$^1$H NMR (DMSO-d6, 400 MHz): 1.32 (s, 3H); 2.26 (s, 3H); 3.04 (s, 3H); 4.28-4.31 (m, 2H); 4.40 (s, 2H); 4.58 (d, J=6.2 Hz, 1H); 4.64 (d, J=6.2 Hz, 1H); 5.64 (d, J=9.8 Hz, 1H); 6.06-6.07 (m, 1H); 6.26 (d, J=3.0 Hz, 1H); 7.01 (d, J=8.1 Hz, 1H); 7.88 (d, J=8.1 Hz, 1H); 8.84 (d, J=9.8 Hz, 1H); 9.50 (s, 1H); 9.76 (s, 1H).

EXAMPLE 14

Preparation of 3-[2-hydroxy-3-(pyrrolidine-1-carbonyl)phenylamino]-4-{[(5-methylfuran-2-yl)-(3-methyloxetan-3-yl)methyl]amino}cyclobut-3-ene-1,2-dione

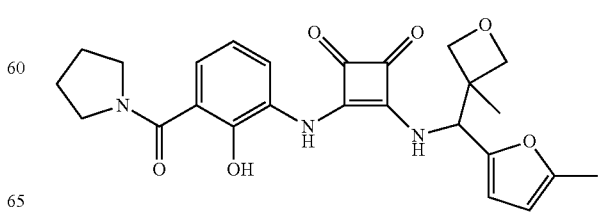

Step 1

In a manner analogous to EXAMPLE 1 (step 4), (2-hydroxy-3-nitrophenyl)pyrrolidin-1-ylmethanone was prepared.

Step 2

In a manner analogous to EXAMPLE 1 (step 5), (3-amino-2-hydroxyphenyl)pyrrolidin-1-ylmethanone was prepared.

Step 3

A solution of 0.99 g (4.8 mmol) of (3-amino-2-hydroxyphenyl)pyrrolidin-1-ylmethanone and 2.73 g (19.2 mmol) of 3,4-dimethoxycyclobut-3-ene-1,2-dione in 100 ml of methanol was heated at 50° C. for five and a half hours. The reaction medium was concentrated. The residue was taken up with ethyl acetate and was washed twice with a 1 M aqueous sodium dihydrogen phosphate solution. The organic phase was dried over anhydrous sodium sulfate, filtered and concentrated. The residue was chromatographed on silica gel (300 g prepacked column: eluent heptane/ethyl acetate from 60% to 100% of ethyl acetate). 0.85 g of product was obtained in the form of a pale yellow solid. Yield=56%.

Step 4

3-[2-Hydroxy-3-(pyrrolidine-1-carbonyl)phenylamino]-4-{[(5-methylfuran-2-yl)-(3-methyloxetan-3-yl)methyl]amino}cyclobut-3-ene-1,2-dione 385 mg (2.12 mmol) of C-(5-methylfuran-2-yl)-C-(3-methyloxetan-3-yl)methylamine in solution in 3 ml of methanol were added to a solution of 443 mg (1.40 mmol) of 3-ethoxy-4-[2-hydroxy-3-(pyrrolidine-1-carbonyl)phenylamino]cyclobut-3-ene-1,2-dione in 42 ml of methanol. The reaction medium was heated at 50° C. for 13 hours. The reaction medium was concentrated. The residue was taken up with ethyl acetate and was washed twice with a 1 M aqueous sodium dihydrogen phosphate solution. The organic phase was dried over anhydrous sodium sulfate, filtered and concentrated. 0.62 g of product were obtained in the form of a beige solid. Yield=95%, HPLC=94.06%, Mp=210° C.

$^1$H NMR (DMSO-d6, 400 MHz): 1.33 (s, 3H); 1.86 (m, 4H); 2.26 (s, 3H); 3.53 (m, 4H); 4.28-4.31 (m, 2H); 4.58 (d, J=6.2 Hz, 1H); 4.66 (d, J=6.2 Hz, 1H); 5.66 (d, J=9.8 Hz, 1H); 6.06-6.07 (m, 1H); 6.26 (d, J=3.1 Hz, 1H); 6.89 (t, J=8.0 Hz, 1H); 7.16 (dd, J=7.9 Hz, J=1.4 Hz, 1H); 7.86 (dd, J=8.0 Hz, J=1.2 Hz, 1H); 8.86 (d, J=9.8 Hz, 1H); 9.50 (s, 1H); 11.56 (s, 1H).

EXAMPLE 15

Preparation of 3-[2-hydroxy-3-(morpholine-4-carbonyl)phenylamino]-4-{[(5-methylfuran-2-yl)-(3-methyloxetan-3-yl)methyl]amino}cyclobut-3-ene-1,2-dione

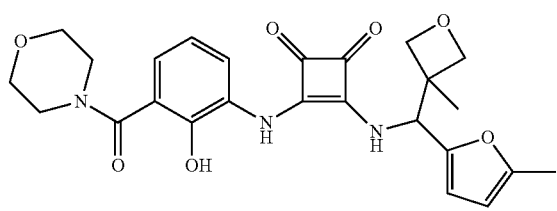 [SMILES: Cc1ccc(C(Nc2c(Nc3cccc(C(=O)N4CCOCC4)c3O)c(=O)c2=O)C2(C)COC2)o1]

Step 1

In a manner analogous to EXAMPLE 5 (step 1), (2-hydroxy-3-nitrophenyl)morpholin-4-ylmethanone was prepared.

Step 2

In a manner analogous to EXAMPLE 5 (step 2), (3-amino-3-hydroxyphenyl)morpholin-4-ylmethanone was prepared.

Step 3

3-[2-Hydroxy-3-(morpholine-4-carbonyl)phenylamino]-4-methoxycyclobut-3-ene-1,2-dione A solution of 1.00 g (4.5 mmol) of (3-amino-2-hydroxyphenyl)morpholin-4-ylmethanone and 2.56 g (18.0 mmol) of 3,4-dimethoxycyclobut-3-ene-1,2-dione in 100 ml of methanol was heated at 50° C. for five and a half hours. The reaction medium was concentrated. The residue was taken up in ethyl acetate and was washed twice with a 1 M aqueous sodium dihydrogen phosphate solution. The organic phase was dried over anhydrous sodium sulfate, filtered and concentrated. The solvent was evaporated off and the residue was chromatographed on silica gel (200 g prepacked column, eluent dichloromethane/methanol from 0 to 5% of methanol). 0.81 g of a yellow solid was obtained (dirty fraction). This solid was taken up in methanol with stirring, filtered and rinsed with methanol. 0.50 g of product was obtained in the form of a pale yellow solid. Yield=33%.

Step 4

3-[2-Hydroxy-3-(morpholine-4-carbonyl)phenylamino]-4-{[(5-methylfuran-2-yl)-(3-methyloxetan-3-yl)methyl]amino}cyclobut-3-ene-1,2-dione 205 mg (1.13 mmol) of C-(5-methylfuran-2-yl)-C-(3-methyloxetan-3-yl)methylamine in solution in 3 ml of methanol were added to a suspension of 249 mg (0.75 mmol) of 3-[2-hydroxy-3-(morpholine-4-carbonyl)phenylamino]-4-methoxycyclobut-3-ene-1,2-dione in 22 ml of methanol. The reaction medium was then heated at 50° C. for two hours and stirred at ambient temperature for 3 days. The reaction medium was concentrated. The residue was taken up with ethyl acetate and was washed twice with a 1 M aqueous sodium dihydrogen phosphate solution. The organic phase was dried over anhydrous sodium sulfate, filtered and concentrated. The residue was chromatographed on silica gel (25 g prepacked column: eluent heptane/ethyl acetate from 80% to 100% of ethyl acetate). 0.23 g of product were obtained in the form of a yellow solid. Yield=64%, HPLC purity=98.01%

$^1$H NMR (DMSO-d6, 400 MHz): 1.32 (s, 3H); 2.26 (s, 3H); 3.20-3.70 (m, 8H); 4.29 (dd, J=6.2 Hz, J=2.4 Hz, 2H); 4.58 (d, J=6.2 Hz, 1H); 4.65 (d, J=6.2 Hz, 1H); 5.65 (d, J=9.7 Hz, 1H); 6.06-6.07 (m, 1H); 6.26 (d, J=3.1 Hz, 1H); 6.82-6.93 (m, 2H); 7.79 (dd, J=7.7 Hz, J=1.7 Hz, 1H); 8.86 (d, J=9.8 Hz, 1H); 9.40-9.55 (m, 1H); 9.85-10.20 (m, 1H).

EXAMPLE 16

Preparation of 3-(4-hydroxypyrimidin-5-ylamino)-4-{[(5-methylfuran-2-yl)-(3-methyloxetan-3-yl)methyl]amino}cyclobut-3-ene-1,2-dione

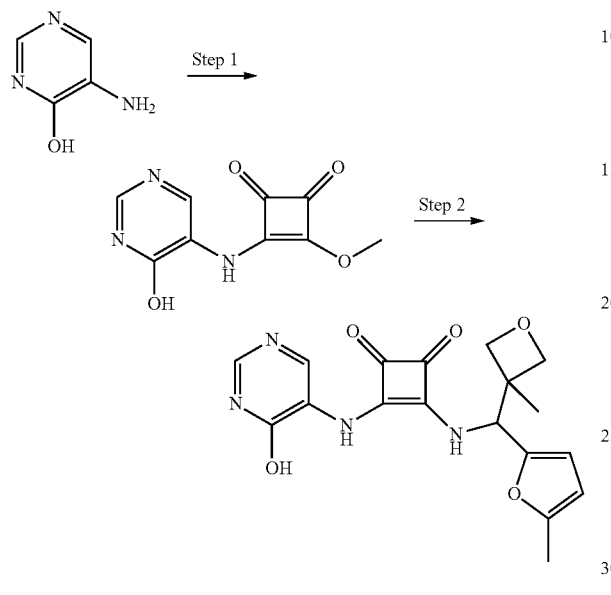

Step 1

3-(4-Hydroxypyrimidin-5-ylamino)-4-methoxycyclobut-3-ene-1,2-dione 1.00 g (6.78 mmol, 1 eq) of 5-aminopyrimidin 4-ol hydrochloride and 0.95 ml (6.78 mmol, 1 eq) of triethylamine were added to a suspension of 3.86 g (27.16 mmol, 4 eq) of 3,4-dimethoxycyclobut-3-ene-1,2-dione in 20 ml of methanol. The reaction medium was heated at 50° C. for 18 hours. The reaction medium was left at ambient temperature. The precipitate was filtered off and washed with methanol. 1.19 g of product were obtained in the form of a yellow solid. Yield=79%.

Step 2

3-(4-Hydroxypyrimidin-5-ylamino)-4-{[(5-methylfuran-2-yl)-(3-methyloxetan-3-yl)methyl]amino}cyclobut-3-ene-1,2-dione A mixture of 300 mg (1.36 mmol, 1 eq) of 3-(4-hydroxypyrimidin-5-ylamino)-4-methoxycyclobut-3-ene-1,2-dione and 504 mg (2.78 mmol, 2 eq) of C-(5-methylfuran-2-yl)-C-(3-methyloxetan-3-yl)methylamine in 25 ml of methanol was heated at 50° C. for 22 hours. The reaction medium was filtered and the insoluble material was washed with methanol and with diethyl ether. 0.36 g of product was obtained in the form of a white solid. Yield=72%, HPLC purity=97.81%, Mp=281° C. (degradation).

$^1$H NMR (DMSO-d6, 400 MHz): 1.30 (s, 3H); 2.25 (s, 3H); 4.27-4.29 (m, 2H); 4.57 (d, J=6.2 Hz, 1H); 4.62 (d, J=6.2 Hz, 1H); 5.60 (d, J=9.7 Hz, 1H); 6.05-6.06 (m, 1H); 6.25 (d, J=3.1 Hz, 1H); 7.99 (s, 1H); 8.52 (s, 1H); 8.98 (d, J=9.8 Hz, 1H); 9.58 (s, 1H); 12.88 (s, 1H).

EXAMPLE 17

Preparation of 3-{[(5-methylfuran-2-yl)-(3-methyloxetan-3-yl)methyl]amino}-4-(1-methyl-2-oxo-1,2-dihydroquinolin-3-ylamino)cyclobut-3-ene-1,2-dione

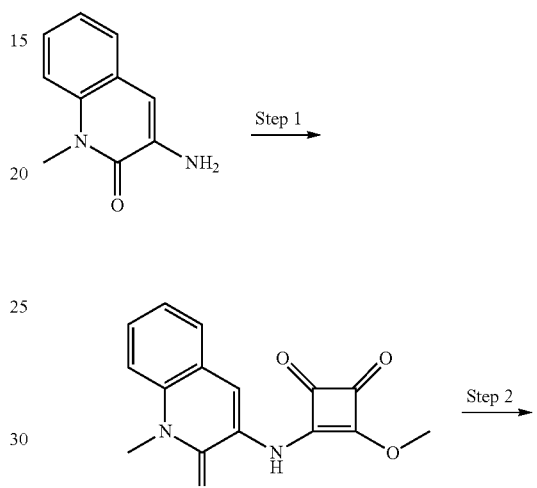

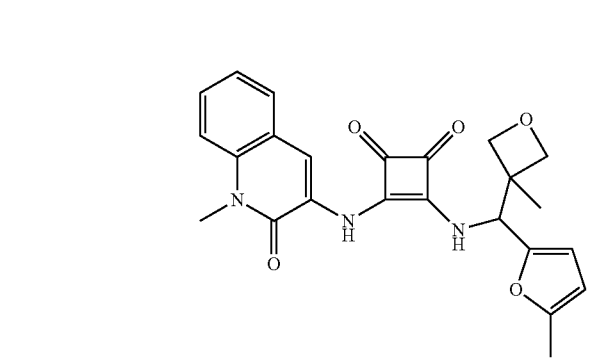

Step 1

In a manner analogous to EXAMPLE 1 (step 6), 3-methoxy-4-(1-methyl-2-oxo-1,2-dihydroquinolin-3-ylamino)cyclobut-3-ene-1,2-dione was prepared. Yield=67%.

Step 2

In a manner analogous to EXAMPLE 1 (step 7), 3-{[(5-methylfuran-2-yl)-(3-methyloxetan-3-yl)methyl]amino}-4-(1-methyl-2-oxo-1,2-dihydroquinolin-3-ylamino)cyclobut-3-ene-1,2-dione was prepared. Yield=31%, Mp=155-161° C.

$^1$H NMR (DMSO-d6, 400 MHz): 1.33 (s, 3H); 2.27 (s, 3H); 3.76 (s, 3H); 4.30 (t, J=4.2-5.6 Hz, 2H); 4.58 (d, J=6.1 Hz, 1H); 4.65 (d, J=9.3 Hz, 1H); 5.65 (d, J=9.3 Hz, 1H); 6.07 (s,

1H); 7.27 (d, J=2.7 Hz, 1H); 7.30 (t, J=6.1-6.4 Hz, 1H); 7.45-7.65 (m, 3H); 8.38 (s, 1H); 9.16 (d, J=9.4 Hz, 1H); 9.88 (s, 1H).

EXAMPLE 18

Preparation of 3-{[(5-methylfuran-2-yl)-(3-methyloxetan-3-yl)methyl]amino}-4-(6-methyl-2-oxo-2H-pyran-3-ylamino)cyclobut-3-ene-1,2-dione

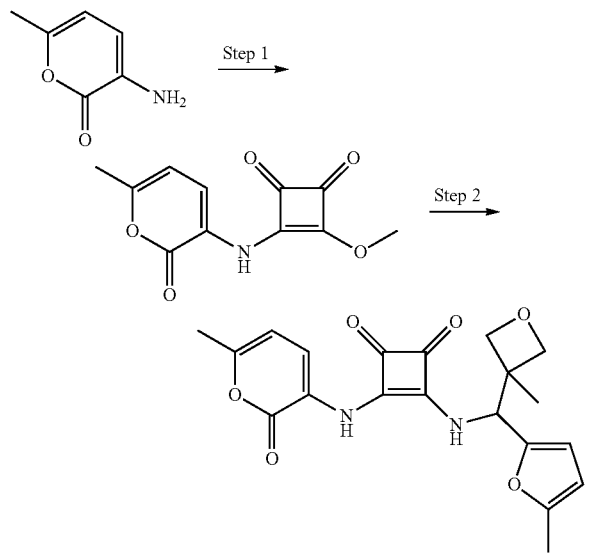

Step 1

In a manner analogous to EXAMPLE 1 (step 6), 3-methoxy-4-(6-methyl-2-oxo-2H-pyran-3-ylamino)cyclobut-3-ene-1,2-dione was prepared.

Step 2

In a manner analogous to EXAMPLE 1 (step 7), 3-{[(5-methylfuran-2-yl)-(3-methyloxetan-3-yl)methyl]amino}-4-(6-methyl-2-oxo-2H-pyran-3-ylamino)cyclobut-3-ene-1,2-dione was prepared.

EXAMPLE 19

Preparation of 3-{[(5-methylfuran-2-yl)-(3-methyloxetan-3-yl)methyl]amino}-4-(1-methyl-2-oxo-1,2-dihydropyridin-3-ylamino)cyclobut-3-ene-1,2-dione

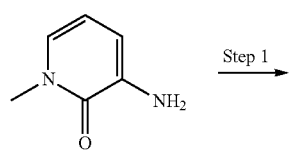

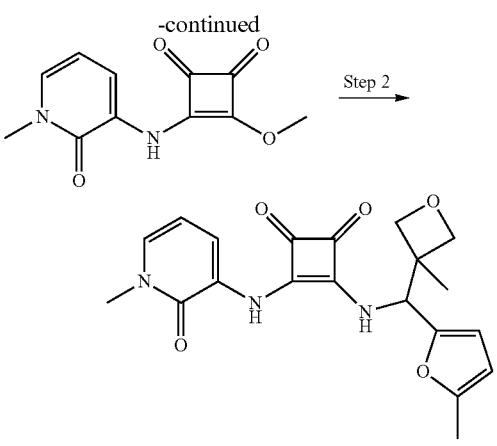

Step 1

In a manner analogous to EXAMPLE 1 (step 6), 3-methoxy-4-(1-methyl-2-oxo-1,2-dihydropyridin-3-ylamino)cyclobut-3-ene-1,2-dione was prepared. Yield=50%.

Step 2

In a manner analogous to EXAMPLE 1 (step 7), 3-{[(5-methylfuran-2-yl)-(3-methyloxetan-3-yl)methyl]amino}-4-(1-methyl-2-oxo-1,2-dihydroquinolin-3-ylamino)cyclobut-3-ene-1,2-dione was prepared. Yield=86%.

$^1$H NMR (DMSO-d6, 400 MHz): 1.31 (s, 3H); 2.26 (s, 3H); 3.53 (s, 3H); 4.27-4.29 (m, 2H); 4.57 (d, J=6.2 Hz, 1H); 4.63 (d, J=6.2 Hz, 1H); 5.62 (d, J=9.7 Hz, 1H); 6.05-6.06 (m, 1H); 6.24 (d, J=3.1 Hz, 1H); 6.29 (t, J=7.1 Hz, 1H); 7.41 (dd, J=6.7 Hz, J=1.6 Hz, 1H); 8.00 (dd, J=7.4 Hz, J=1.5 Hz, 1H); 9.08 (bd, J=9.8 Hz, 1H); 9.70 (s, 1H).

EXAMPLE 20

Preparation of 3-(2-hydroxypyridin-3-ylamino)-4-{[(5-methylfuran-2-yl)-(3-methyloxetan-3-yl)methyl]amino}-cyclobut-3-ene-1,2-dione

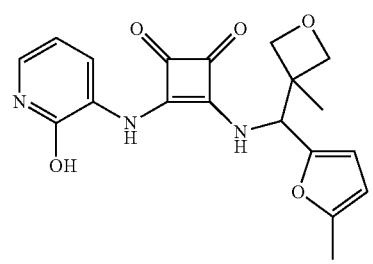 [SMILES: Cc1ccc(C(Nc2c(Nc3cccnc3O)c(=O)c2=O)C2(C)COC2)o1]

In a manner analogous to EXAMPLE 1 (steps 6 and 7), 3-(2-hydroxypyridin-3-ylamino)-4-{[(5-methylfuran-2-yl)-(3-methyloxetan-3-yl)methyl]amino}cyclobut-3-ene-1,2-dione was prepared from 3-aminopyridin-2-ol. HPLC 94.84%, ES− [369].

$^1$H NMR (DMSO-d6, 400 MHz): 1.31 (s, 3H); 2.25 (s, 3H); 4.27 (d, J=6.2 Hz, 2H); 4.57-4.65 (m, 2H); 5.63 (d, J=9.8 Hz,

1H); 6.02 (s, 1H); 6.20-6.25 (m, 2H); 7.05-7.06 (m, 2H); 8.03-8.05 (m, 1H); 9.05 (d, J=9.8 Hz, 1H); 9.64 (s, 1H)

EXAMPLE 21

Preparation of 2-hydroxy-N,N-dimethyl-3-(2-{[(5-methylfuran-2-yl)-(3-methyloxetan-3-yl)methyl]amino}-3,4-dioxocyclobut-1-enylamino)benzenesulfonamide

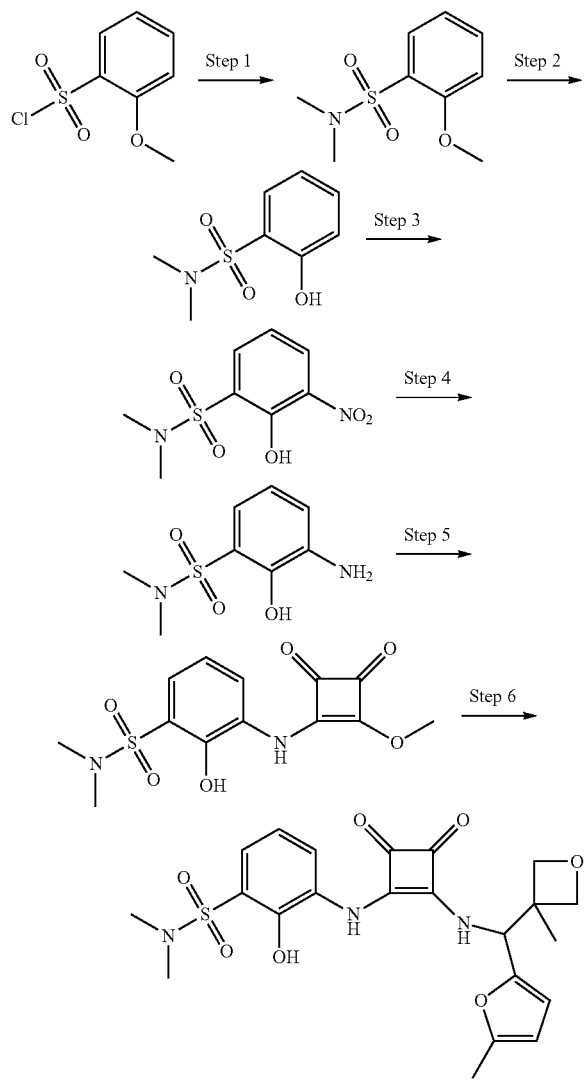

Step 1

2-Methoxy-N,N-dimethylbenzenesulfonamide 72 ml (144 mmol, 3 eq) of a 2 M solution of dimethylamine in tetrahydrofuran were added dropwise to a solution of 9.90 g (47.9 mmol, 1 eq) of 2-methoxybenzenesulfonyl chloride in 300 ml of tetrahydrofuran at 0° C. under nitrogen. After 30 minutes, the reaction medium was hydrolyzed with water, and ethyl acetate was added. The organic phase was again washed with water, and then dried over anhydrous sodium sulfate, filtered and concentrated. 8.78 g of product were obtained in the form of a brown oil. Yield=85%.

Step 2

2-Hydroxy-N,N-dimethylbenzenesulfonamide 200 ml (200 mmol, 4.9 eq) of a 1 M solution of tribromoborane in dichloromethane were added dropwise to a solution of 8.78 g (40.8 mmol, 1 eq) of 2-methoxy-N,N-dimethylbenzenesulfonamide in 250 ml of dichloromethane at −70° C. under nitrogen. The reaction medium was left at −70° C. for one hour and was then left to return to 10° C. for one and a half hours. The reaction medium was then cooled to −70° C. and approximately 100 ml of methanol were added dropwise (approximately one hour of addition). The reaction medium was then left to return to ambient temperature and was concentrated. The residue obtained was filtered off on silica with the eluent 6/4 heptane/ethyl acetate. 7.81 g of product were obtained in the form of a beige solid. Yield=95%.

Step 3

2-Hydroxy-N,N-dimethyl-3-nitrobenzenesulfonamide 2.24 ml (47.4 mmol, 1.3 eq) of fuming nitric acid at 90% were added, over the course of 15 minutes, to a mixture of 7.17 g (35.6 mmol, 1 eq) of 2-hydroxy-N,N-dimethylbenzenesulfonamide in 35.5 ml of acetic acid in a bath at 5° C. The reaction medium was then stirred at ambient temperature. After one and a half hours, the reaction medium was hydrolyzed with water and brine. The reaction medium was then extracted with a 4/1 ethyl acetate/heptane mixture (2×100 ml). The organic phases were combined, dried over anhydrous sodium sulfate, filtered and concentrated. The solid obtained (8.66 g) was combined with GUL1537-178 and was chromatographed on silica gel (prepacked column, eluent heptane/(ethyl acetate+1% methanol), from 20% to 65% of (ethyl acetate+1% methanol)). A fraction enriched in ortho isomer was isolated, that is to say 3.7 g of a yellow solid. This solid was recrystallized from 40 ml of ethanol. 1.93 g of product were obtained in the form of a pale yellow solid. Yield=20%.

Step 4

3-Amino-2-hydroxy-N,N-dimethyl-benzenesulfonamide 104 mg (10% by weight) of palladium on carbon at 10% were added to a solution of 1.01 g (4.10 mmol) of 2-hydroxy-N,N-dimethyl-3-nitrobenzenesulfonamide in 20 ml of methanol and 20 ml of tetrahydrofuran. The reaction medium was stirred under a hydrogen atmosphere for 17 hours. The reaction medium was filtered through celite and was concentrated. 0.94 g of product was obtained in the form of a brown solid. Quantitative yield.

Step 5

2-Hydroxy-3-(2-methoxy-3,4-dioxocyclobut-1-enylamino)-N,N-dimethylbenzenesulfonamide A mixture of 0.94 g (4.10 mmol) of 3-amino-2-hydroxy-N,N-dimethylbenzenesulfonamide and 2.47 g (17.40 mmol) of 3,4-diethoxycyclobut-3-ene-1,2-dione in 20 ml of methanol was stirred at ambient temperature for 4 days. The reaction medium was concentrated. The residue (3.29 g) was chromatographed on silica gel (200 g prepacked column, 100 ml/min, eluent heptane/ethyl acetate, from 50% to 85% of ethyl acetate). 0.86 g of product was obtained in the form of a yellow solid. Yield=64%.

Step 6

2-Hydroxy-N,N-dimethyl-3-(2-{[(5-methylfuran-2-yl)-(3-methyloxetan-3-yl)methyl]amino}-3,4-dioxo-cyclobut-1-enylamino)benzenesulfonamide A mixture of 284 mg (0.87 mmol, 1 eq) of 2-hydroxy-3-(2-methoxy-3,4-dioxocyclobut-1-enylamino)-N,N-dimethylbenzenesulfonamide and 318 mg (1.75 mmol) of C-(5-methylfuran-2-yl)-C-(3-methyloxetan-3-yl)methylamine in 20 ml of methanol was heated at 50° C. for 3 days. The reaction medium was concentrated. The residue was taken up in ethyl acetate and was washed twice with a 1 M aqueous sodium dihydrogen phosphate solution. The organic phase was dried over anhydrous sodium sulfate, filtered and concentrated. 0.29 g of product was obtained in the form of an ochre solid. Yield=70%, HPLC=98.68%, Mp=123° C.

¹H NMR (DMSO-d6, 400 MHz): 1.32 (s, 3H); 2.26 (s, 3H); 2.73 (s, 6H); 4.28-4.30 (m, 2H); 4.58 (d, J=6.2 Hz, 1H); 4.64 (d, J=6.2 Hz, 1H); 5.62 (d, J=9.8 Hz, 1H); 6.06-6.07 (m, 1H); 6.27 (d, J=3.1 Hz, 1H); 7.08 (t, J=8.0 Hz, 1H); 7.32 (dd, J=8.0 Hz, J=1.3 Hz, 1H); 7.91 (d, J=8.0 Hz, 1H); 8.80 (d, J=9.8 Hz, 1H); 9.54 (s, 1H); 9.66 (s, H).

EXAMPLE 22

Preparation of 2-Hydroxy-N,N-dimethyl-3-(2-{[(R)-(5-methylfuran-2-yl)-(3-methyloxetan-3-yl)methyl]amino}-3,4-dioxocyclobut-1-enylamino)benzene-sulfonamide

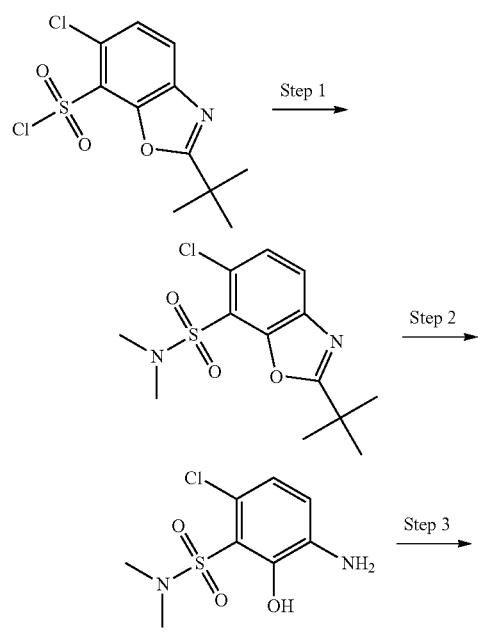

Step 1

2-tert-Butyl-6-chlorobenzooxazole-7-sulfonic acid dimethylamide 4.05 ml of triethylamine (29.20 mmol; 3.0 eq) and 29.2 ml of 2 M dimethylamine (58.41 mmol; 6.0 eq) in tetrahydrofuran were added to a solution of 3.0 g of 2-tert-butyl-6-chlorobenzooxazole-7-sulfonyl chloride (9.73 mmol; 1.0 eq) in 90 ml of tetrahydrofuran under nitrogen at 0° C. After two and a half hours, the reaction medium was hydrolyzed with water and extracted twice with ethyl acetate. The organic phases were combined, dried over anhydrous sodium sulfate, filtered and concentrated.

2.96 g of 2-tert-butyl-6-chlorobenzooxazole-7-sulfonic acid dimethylamide were obtained. Yield=95.98%.

Step 2

3-Amino-6-chloro-2-hydroxy-N,N-dimethylbenzenesulfonamide 3.4 ml of sulfuric acid (63.59 mmol; 1.16 V) and 3.4 ml of water were added to a solution of 2.93 g of 2-tert-butyl-6-chlorobenzooxazole-7-sulfonic acid dimethylamide (9.25 mmol; 1.0 eq) in 13 ml of 1,4-dioxane. The reaction medium was refluxed for four and a half hours. The reaction medium was concentrated. 130 ml of 1 M sodium hydroxide were added to the residue (pH=10), followed by 400 ml of water. The solution was extracted with ethyl acetate (2×250 ml). The organic phases were combined, dried over anhydrous sodium sulfate, filtered and concentrated. The residue was chromatographed on silica gel (250 g prepacked column: eluent heptane/ethyl acetate, from 20% to 40% of ethyl acetate, flow rate 100 ml/min). 1.66 g of 3-amino-6-chloro-2-hydroxy-N,N-dimethylbenzenesulfonamide were obtained. Yield=72%.

Step 3

6-Chloro-2-hydroxy-3-(2-methoxy-3,4-dioxocyclobut-1-enylamino)-N,N-dimethbenzenesulfonamide 3-amino-6-chloro-2-hydroxy-N,N-dimethylbenzenesulfonamide (1.59 g; 6.34 mmol; 1.0 eq) was added to a solution of 3,4-cyclobutane-1,2-dione (1.80 g; 12.68 mmol; 2.0 eq) in 80 ml of methanol. The reaction medium was heated at 50° C. for 5 hours. The precipitate formed was filtered off. The filtrate was concentrated and the residue obtained was chromatographed on silica gel (240 g prepacked column: eluent heptane/ethyl acetate, from 40% to 70% of ethyl acetate, 100 ml/min). 1.04 g of 6-chloro-2-hydroxy-3-(2-methoxy-3,4-dioxocyclobut-1-enylamino)-N,N-dimethylbenzenesulfonamide were obtained. Yield=45%.

Step 4

2-Hydroxy-N,N-dimethyl-3-(2-{[(R)-(5-methylfuran-2-yl)-(3-methyloxetan-3-yl)methyl]amino}-3,4-dioxocyclobut-1-enylamino)benzenesulfonamide A mixture of 6-chloro-2-hydroxy-3-(2-methoxy-3,4-dioxocyclobut-1-enylamino)-N,N-dimethylbenzenesulfonamide (0.25 g; 0.69 mmol; 1.0 eq) and C—[(R)—C-(5-methylfuran-2-yl)-C-(3-methyloxetan-3-yl)]methylamine (0.19 g; 1.04 mmol; 1.5 eq) in 20 ml of methanol was heated at 50° C. for 23 hours. The reaction medium was concentrated while leaving a few milliliters of solvent and was filtered under vacuum. The solid obtained was washed with methanol. 210.00 mg of 6-chloro-2-hydroxy-N,N-dimethyl-3-(2-{[(R)-(1-methylcyclobutyl)-(5-methylfuran-2-yl)methyl]amino}-3,4-dioxocyclobut-1-enylamino)benzenesulfonamide were obtained. Yield=59.43%, Mp=152° C.

$^1$H NMR (DMSO-d6, 400 MHz): 1.32 (s, 3H), 2.26 (s, 3H), 2.88 (s, 6H), 4.28-4.30 (m, 2H), 4.57 (d, J=6.2 Hz, 1H), 4.64 (d, J=6.2 Hz, 1H), 5.63 (d, J=9.8 Hz, 1H), 6.07 (dd, J=3.1 Hz, J=1.0 Hz, 1H), 6.26 (d, J=3.1 Hz, 1H), 7.22 (d, J=8.8 Hz, 1H), 7.99 (d, J=8.8 Hz, 1H), 8.90 (d, J=9.8 Hz, 1H), 9.58 (s, 1H), 10.58 (s, 1H)

EXAMPLE 23

Preparation of 3-(3H-benzotriazol-4-ylamino)-4-{[(5-methylfuran-2-yl)-(3-methyloxetan-3-yl)methyl]amino}cyclobut-3-ene-1,2-dione

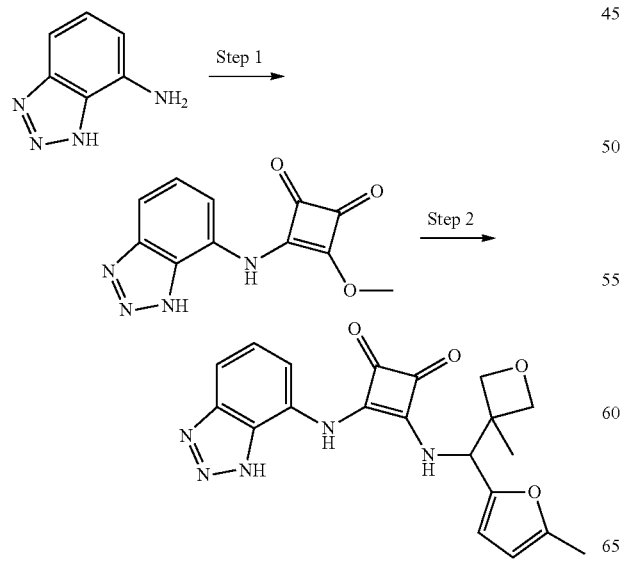

Step 1

3-(3H-Benzotriazol-4-ylamino)-4-methoxycyclobut-3-ene-1,2-dione

A mixture of 2.045 g (15.2 mmol, 1 eq) of 1H-1,2,3-benzotriazol-4-amine and 1.80 g (12.7 mmol, 1 eq) of 3,4-dimethoxy-3-cyclobutene-1,2-dione in 30 ml of methanol was stirred at ambient temperature for 2 days. The reaction medium (set solid) was filtered. 2.04 g of a mixture of 3-(3H-benzotriazol-4-ylamino)-4-methoxycyclobut-3-ene-1,2-dione and 3,4-bis(3H-benzotriazol-4-ylamino)cyclobut-3-ene-1,2-dione were obtained in the form of a yellow solid. Mixture of products (29% correct product). Yield=19%.

Step 2

3-(3H-Benzotriazol-4-ylamino)-4-{[(5-methylfuran-2-yl)-(3-methyloxetan-3-yl)methyl]amino}-cyclobut-3-ene-1,2-dione A mixture of 263 mg (1.45 mmol, 1.2 eq) of C-(5-methylfuran-2-yl)-C-(3-methyloxetan-3-yl)methylamine and 1.02 g (1.21 mmol, 1 eq) of 3-(3H-benzotriazol-4-ylamino)-4-methoxycyclobut-3-ene-1,2-dione at 29% in 25 ml of methanol was heated at 50° C. for 24 hours. The insoluble material (dimer) was filtered off and the filtrate was evaporated. The residue was chromatographed on silica gel (column puriFlash PF-30SIHP/40G, Spot II) eluted with dichloromethane/methanol (gradient). The solid was taken up with ethyl acetate and this organic phase was washed several times with a 1 N sodium dihydrogen phosphate solution, dried over magnesium sulfate, filtered and evaporated. 205 mg of 3-(3H-benzotriazol-4-ylamino)-4-{[(5-methyl furan-2-yl)-(3-methyloxetan-3-yl)methyl]amino}cyclobut-3-ene-1,2-dione were obtained in the form of a yellow solid. (Mp=178-180° C.). Yield=43%, LC/MS: 95.97% [393].

$^1$H NMR (DMSO-d6, 400 MHz): 1.35 (s, 3H); 2.27 (s, 3H); 4.31 (t, J=5.8 Hz, 1H); 4.6 (dd, J=24.4 Hz, 2H); 5.67 (d, J=9.8 Hz, 1H); 6.08 (dd, J=3.1 Hz, 1H); 6.30 (d, J=3.1 Hz, 1H); 7.40 (d, J=8.0 Hz, 1H); 7.45-7.49 (t, J=8.0 Hz, 1H); 7.85 (d, J=7.5 Hz, 1H); 8.93 (d, J=9.2 Hz, 1H); 10.6 (s, 1H); 15.87 (s, 1H).

EXAMPLE 24

3-{[(5-Methylfuran-2-yl)-(3-methyloxetan-3-yl)methyl]amino}-4-(2-oxo-2,3-dihydrobenzooxazol-7-ylamino)cyclobut-3-ene-1,2-dione

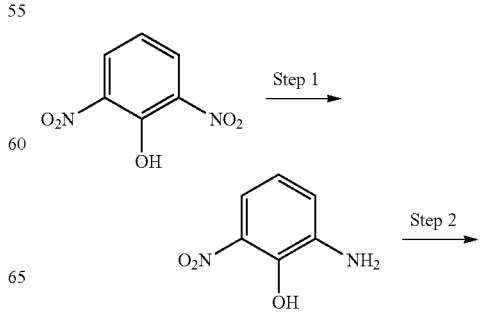

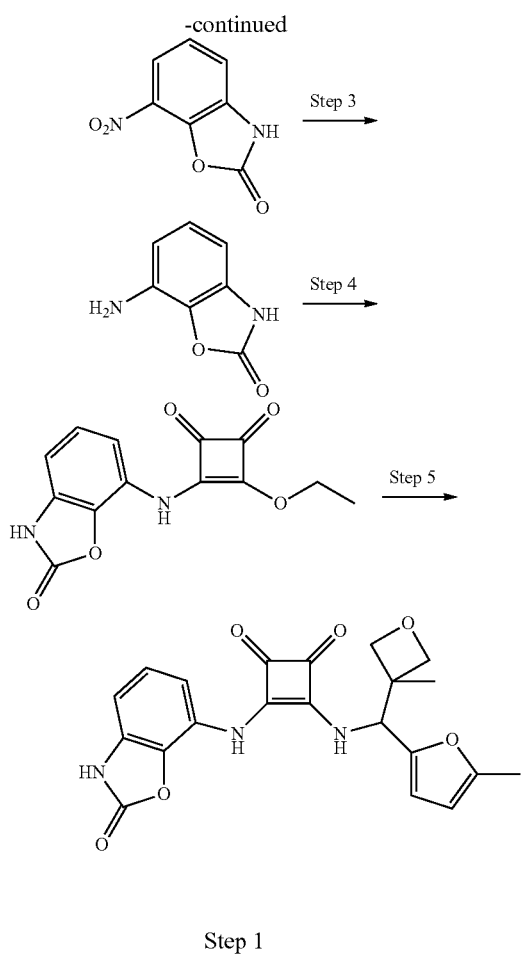

Step 1

2-Amino-6-nitrophenol 8.6 g of 2,6-dinitrophenol (46.71 mmol) were dissolved in 95 ml of ethyl acetate. The solution was degassed and then 0.86 g (10% by weight) of palladium on carbon at 10% was added. The reaction medium was stirred under a hydrogen atmosphere for 6 days at ambient temperature. The reaction medium was filtered through celite and concentrated to dryness. The residue obtained was chromatographed on a cartridge of silica gel eluted with 100% dichloromethane to 80/20 dichloromethane/ethyl acetate. 3.43 g of product were obtained in the form of a dark copper solid. Yield=48%.

Step 2

7-Nitro-3H-benzooxazol-2-one 2.27 g of N,N'-carbonyldiimidazole (14 mmol, 1.4 eq) in a homogeneous suspension in 6 ml of ethyl acetate were added to 1.54 g of 2-amino-6-nitrophenol (10 mmol, 1 eq) in solution in 10 ml of ethyl acetate. The reaction medium was vigorously stirred for 3 hours, and then 10 ml of water were added. The stirring was continued for 15 minutes, before evaporating off approximately ¾ of the ethyl acetate. The reaction medium was brought to 0° C. and then 2 ml of 37% hydrochloric acid were added. The stirring was again continued for 15 minutes. The reaction medium was filtered. The solid obtained was washed with a 1 N hydrochloric acid solution, with water and with a water-ethanol (4:1) mixture, and then oven-dried. 1.3 g of product were obtained in the form of a pale yellow solid. Yield=73%.

Step 3

7-Amino-3H-benzooxazol-2-one

A solution of 0.3 g of 7-nitro-3H-benzooxazol-2-one (1.67 mmol) in 5 ml of ethanol was degassed and then 0.03 g (10% by weight) of palladium on carbon (5%-50% wet) was added thereto. The reaction medium was stirred under a hydrogen atmosphere for 2 hours at ambient temperature. The reaction medium was filtered through celite and concentrated to dryness. 0.25 g of product was obtained in the form of a colorless oil. Yield=99%.

Step 4

3-Ethoxy-4-(2-oxo-2,3-dihydrobenzooxazol-7-ylamino)cyclobut-3-ene-1,2-dione

A mixture of 0.247 g of 7-amino-3H-benzooxazol-2-one (1.6 mmol, 1 eq) and 0.36 ml of 3,4-diethoxycyclobut-3-ene-1,2-dione (2.5 mmol, 1.5 eq) in 9 ml of ethanol was stirred at ambient temperature for 2 days (formation of a precipitate). Ethanol was added in order to promote the fall of the precipitate, which was filtered off, washed with diethyl ether and dried under vacuum at 45° C. 0.35 g of product was obtained in the form of a light khaki solid. Yield=78%.

Step 5

3{[(5-Methylfuran-2-yl)-(3-methyloxetan-3-yl)methyl]amino}-4-(2-oxo-2,3-dihydrobenzooxazol-7-ylamino)cyclobut-3-ene-1,2-dione A mixture of 0.35 g (1.28 mmol, 1 eq) of 3-ethoxy-4-(2-oxo-2,3-dihydrobenzooxazol-7-ylamino)cyclobut-3-ene-1,2-dione and 0.278 g (1.53 mmol, 1.2 eq) of C-(5-methylfuran-2-yl)-C-(3-methyloxetan-3-yl)methylamine in 6 ml of methanol was heated at 65° C. for 5 hours. The methanol was evaporated off and the residue was chromatographed on silica gel, eluted with 95/5 dichloromethane/methanol. The paste obtained was crystallized from ethyl ether, filtered and dried under vacuum at 40° C. 0.24 g of product was obtained in the form of a beige solid. Yield=46%. HPLC 96.4%, ES+ [410].

$^1$H NMR (DMSO-d6, 400 MHz): 1.33 (s, 3H); 2.27 (s, 3H); 4.29-4.31 (m, 2H); 4.58 (d, J=6.3 Hz, 2H); 4.64 (d, J=6.2 Hz, 2H); 5.62 (d, J=9.8 Hz, 1H); 6.07 (m, 1H); 6.28 (m, 1H); 6.78-6.80 (m, 1H); 7.13 (t, J=8.0 Hz, 1H); 7.70 (d, J=8.4 Hz, 1H); 8.62 (d, J=9.8 Hz, 1H); 9.84 (s, 1H); 11.79 (s, 1H).

EXAMPLE 25

Preparation of dimethylamide 3-hydroxy-4-(2-{[(R)-(5-methylfuran-2-yl)-(3-methyloxetan-3-yl)methyl]amino}-3,4-dioxcyclobut-1-enylamino)thiophene-2-carboxylate

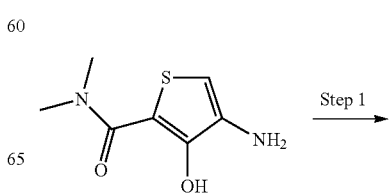

Hz, 2H), 5.60 (d, J=9.8 Hz, 1H), 6.06 (dd, J=1.0-3.0 Hz, 1H), 6.25 (d, J=3.0 Hz, 1H), 7.84 (s, 1H), 8.67 (d, J=9.8 Hz, 1H), 9.66 (s, 1H), 13.01 (s, 1H).

EXAMPLE 26

Preparation of tert-butyl 3-[[2-(3-dimethylcarbamoyl-2-hydroxyphenylamino)-3,4-dioxo-cyclobut-1-enylamino]-(5-methylfuran-2-yl)methyl]-3-methylazetidine-1-carboxylate

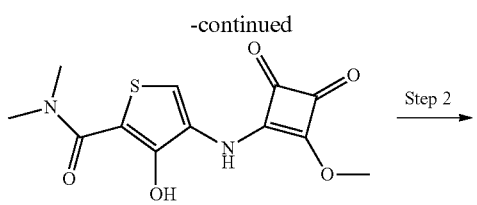

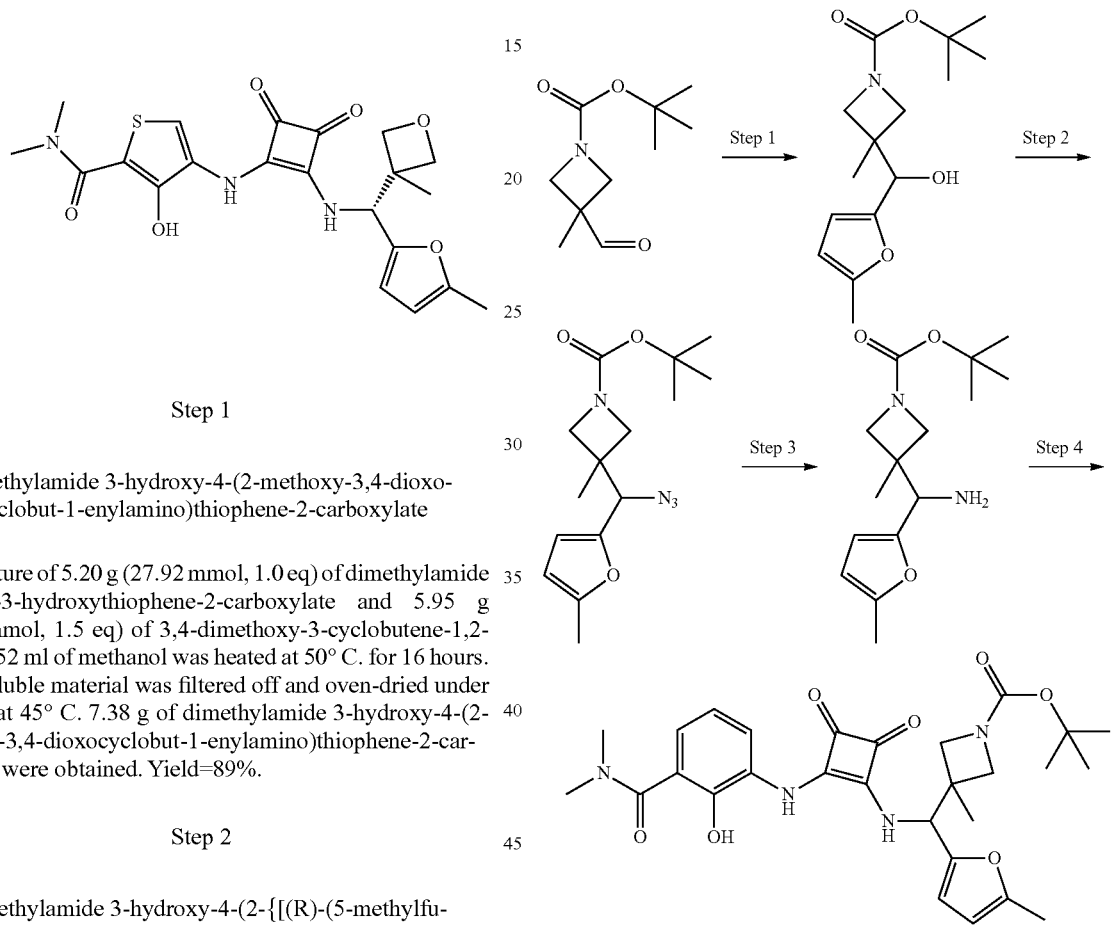

Step 1

Dimethylamide 3-hydroxy-4-(2-methoxy-3,4-dioxocyclobut-1-enylamino)thiophene-2-carboxylate A mixture of 5.20 g (27.92 mmol, 1.0 eq) of dimethylamide 4-amino-3-hydroxythiophene-2-carboxylate and 5.95 g (41.88 mmol, 1.5 eq) of 3,4-dimethoxy-3-cyclobutene-1,2-dione in 52 ml of methanol was heated at 50° C. for 16 hours. The insoluble material was filtered off and oven-dried under vacuum at 45° C. 7.38 g of dimethylamide 3-hydroxy-4-(2-methoxy-3,4-dioxocyclobut-1-enylamino)thiophene-2-carboxylate were obtained. Yield=89%.

Step 2

Dimethylamide 3-hydroxy-4-(2-{[(R)-(5-methylfuran-2-yl)-(3-methyloxetan-3-yl)methyl]amino}-3,4-dioxcyclobut-1-enylamino)thiophene-2-carboxylate A mixture of 300 mg (1.01 mmol, 1.0 eq) of dimethylamide 3-hydroxy-4-(2-methoxy-3,4-dioxocyclobut-1-enylamino) thiophene-2-carboxylate and 220 mg (1.21 mmol, 1.2 eq) of C—[(R)—C-(5-methylfuran-2-yl)-C-(3-methyloxetan-3-yl)]methylamine in 15 ml of methanol was stirred at ambient temperature for two and a half days and was then heated at 50° C. for 21 hours. The reaction medium was evaporated and the residue was chromatographed on silica gel (column puriFlash IR-50SI/40G, Spot II) eluted with dichloromethane/ethyl acetate (75/25). 350 mg of dimethylamide 3-hydroxy-4-(2-{[(R)-(5-methylfuran-2-yl)-(3-methyloxetan-3-yl)methyl]amino}-3,4-dioxcyclobut-1-enylamino)thiophene-2-carboxylate were obtained. Yield=78%.

$^1$H NMR (DMSO-d6, 400 MHz): 1.30 (s, 3H), 2.25 (s, 3H), 3.15 (s, 6H), 4.29 (dd, J=2.9-6.2 Hz, 2H), 4.60 (dd, J=6.2-20.4

Step 1

In a manner analogous to EXAMPLE 1 (step 1), tert-butyl 3-[hydroxy-(5-methylfuran-2-yl)methyl]-3-methylazetidine-1-carboxylate was prepared. Yield=100%.

Step 2

In a manner analogous to EXAMPLE 1 (step 2), tert-butyl 3-[azido-(5-methylfuran-2-yl)methyl]-3-methylazetidine-1-carboxylate was prepared. Yield=48%.

Step 3

In a manner analogous to EXAMPLE 1 (step 3), tert-butyl 3-[amino-(5-methylfuran-2-yl)methyl]-3-methylazetidine-1-carboxylate was prepared. Yield=75%.

Step 4

In a manner analogous to EXAMPLE 1 (step 7), tert-butyl 3-[[2-(3-dimethylcarbamoyl-2-hydroxyphenylamino)-3,4-dioxocyclobut-1-enylamino]-(5-methylfuran-2-yl)methyl]-3-methylazetidine-1-carboxylate was prepared. Yield=88%, Mp=162-165° C., LC/MS: 99.56% [538].

$^1$H NMR (DMSO-d6, 400 MHz): 1.27 (s, 3H); 1.36 (s, 9H); 2.27 (s, 3H); 2.94 (s, 6H); 3.55 (s, 2H); 3.9 (m, 2H); 5.45 (d, 1H); 6.07 (dd, J=3.0 Hz, 1H); 6.29 (d, J=3.1 Hz, 1H); 6.88 (m, 2H); 7.75 (d, J=2.9 Hz, 1H); 8.8 (d, 1H); 9.42 (s, 1H); 10.1 (s, 1H).

EXAMPLE 27

Preparation of 3-(2-{[(4,5-dimethylfuran-2-yl)-(3-methyloxetan-3-yl)methyl]amino}-3,4-dioxocyclobut-1-enylamino)-2-hydroxy-N,N-dimethylbenzamide

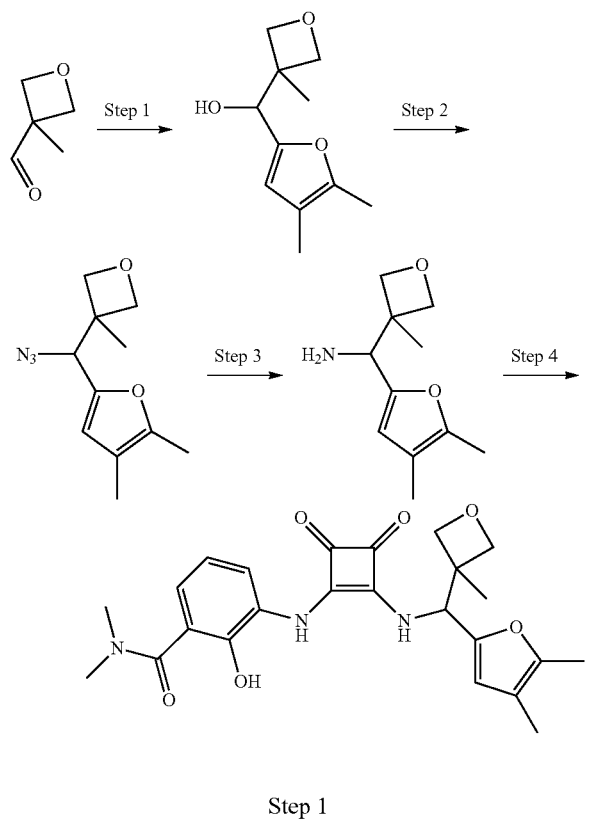

Step 1

In a manner analogous to EXAMPLE 1 (step 1), (4,5-dimethylfuran-2-yl)-(3-methyloxetan-3-yl)methanol was prepared from 2,3-dimethylfuran. Yield=65%.

Step 2

In a manner analogous to EXAMPLE 1 (step 2), 5-[azido(3-methyloxetan-3-yl)methyl]-2,3-dimethylfuran was prepared. Yield=60%.

Step 3

In a manner analogous to EXAMPLE 1 (step 3), C-(4,5-dimethylfuran-2-yl)-C-(3-methyloxetan-3-yl)methylamine ester was prepared. Yield=96%.

Step 4

In a manner analogous to EXAMPLE 1 (step 7), 3-(2-{[(4,5-dimethylfuran-2-yl)-(3-methyloxetan-3-yl)methyl]amino}-3,4-dioxocyclobut-1-enylamino)-2-hydroxy-N,N-dimethylbenzamide was prepared. Yield=75%, Mp=207-209° C., LC/MS: 97.42% [453].

$^1$H NMR (DMSO-d6, 400 MHz): 1.32 (s, 3H); 1.88 (s, 3H); 2.17 (s, 3H); 2.94 (s, 6H); 4.28 (dd, J=6.2 Hz, 2H); 4.6 (dd, J=29.6 Hz, 2H); 5.59 (d, J=9.7 Hz, 1H); 6.15 (s, 1H); 6.88 (m, 2H); 7.76 (dd, J=6.6 Hz, 1H); 8.80 (d, J=9.8 Hz, 1H); 9.45 (s, 1H); 10.0 (s, 1H).

EXAMPLE 28

Preparation of 3-(2-{[(3-methyloxetan-3-yl)-(3-methoxyphenyl)methyl]-amino}-3,4-dioxocyclobut-1-enylamino)-2-hydroxy-N,N-dimethylbenzamide

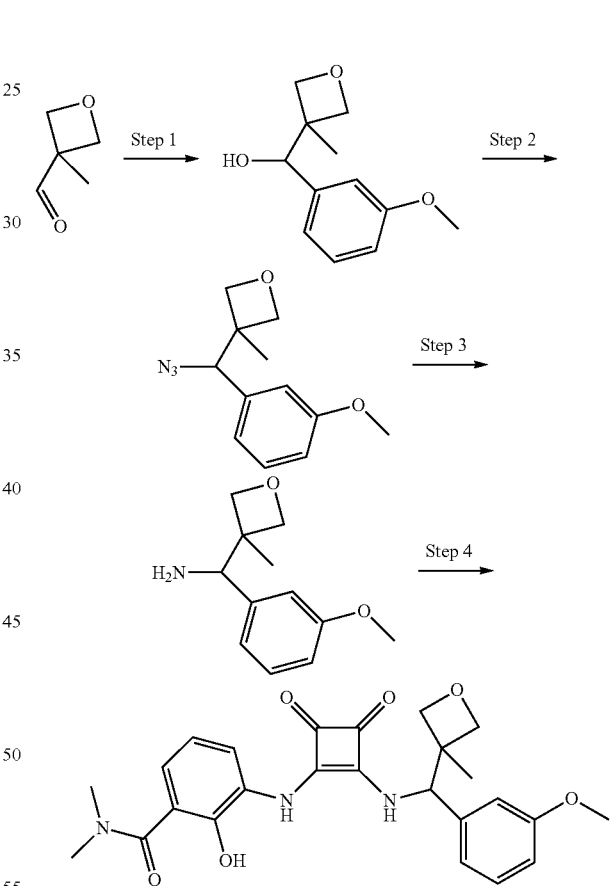

Step 1

(3-Methoxyphenyl)-(3-methyloxetan-3-yl)methanol 1.0 M Magnesium m-methoxybenzene bromide in tetrahydrofuran (25 ml, 25.0 mmol) was added dropwise to a solution of 3-methyloxetane-3-carbaldehyde (0.5 g, 5.0 mmol) in 8 ml of tetrahydrofuran cooled to −70° C. The reaction medium was stirred for 4 hours at −70° C. and then allowed to return to 0° C., hydrolyzed with a saturated sodium chloride solution and extracted with ethyl acetate. The organic phases were combined, washed with a saturated sodium chloride solution and evaporated. The residue obtained was purified by chromatography on a cartridge of silica gel (eluted with heptane/ethyl acetate, gradient from 90/10 to 60/40). 0.45 g of product was obtained in the form of a thick colorless oil. Yield=43%.

Step 2

In a manner analogous to EXAMPLE 1 (step 2), 3-[azido (3-methoxyphenyl)methyl]-3-methyloxetane was prepared. Yield=28%.

Step 3

In a manner analogous to EXAMPLE 1 (step 3), C-(3-methoxyphenyl)-C-(3-methyloxetan-3-yl)methylamine was prepared. Yield=64%.

Step 4

In a manner analogous to EXAMPLE 1 (step 7), 3-(2-{[(3-methyloxetan-3-yl)-(3-methoxyphenyl)methyl]amino}-3,4-dioxocyclobut-1-enylamino)-2-hydroxy-N,N-dimethylbenzamide was prepared. Yield=76%, HPLC 94.3%, ES+ [466].

$^1$H NMR (DMSO-d6, 400 MHz): 1.09 (s, 3H); 2.95 (s, 6H); 3.77 (s, 3H); 4.18 (d, 1H); 4.29 (d, 1H); 4.74 (t, 2H); 5.58 (d, 1H); 6.82-6.93 (m, 5H); 7.34 (t, 1H); 8.74 (d, 1H); 9.40 (s, 1H); 10.05 (s, 1H).

EXAMPLE 29

Preparation of 3-(2-{[(3-methyloxetan-3-yl)-(4-methoxyphenyl)methyl]amino}-3,4-dioxocyclobut-1-enylamino)-2-hydroxy-N,N-dimethylbenzamide

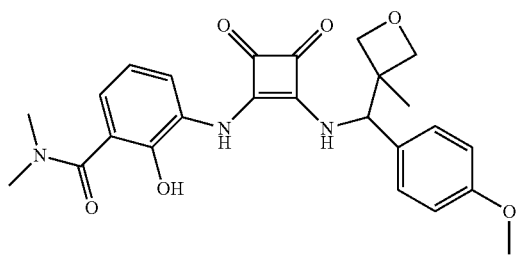

In a manner analogous to EXAMPLE 28 (steps 1 to 4), 3-(2-{[(3-methyloxetan-3-yl)-(4-methoxyphenyl)methyl]amino}-3,4-dioxocyclobut-1-enylamino)-2-hydroxy-N,N-dimethylbenzamide was prepared. HPLC 98.97%, ES+ [465].

$^1$H NMR (DMSO-d6, 400 MHz): 1.28 (s, 3H); 2.95 (s, 6H); 3.75 (s, 3H); 4.18 (d, 1H); 4.29 (d, 1H); 4.67 (d, 1H); 4.72 (d, 1H); 5.56 (d, 1H); 6.88 (d, 2H); 6.97 (d, 2H); 7.21 (d, 2H); 7.72-7.74 (m, 1H); 8.74 (d, 1H); 9.40 (s, 1H)

EXAMPLE 30

Preparation of 3-(2-{[benzo[1,3]dioxol-5-yl-(3-methyloxetan-3-yl)methyl]amino}-3,4-dioxocyclobut-1-enylamino)-2-hydroxy-N,N-dimethylbenzamide

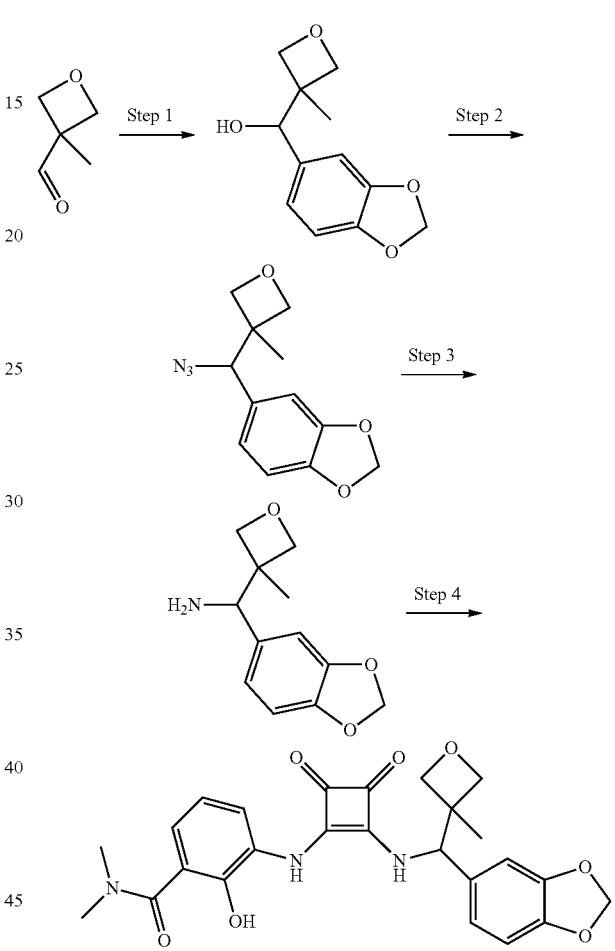

Step 1

In a manner analogous to EXAMPLE 28 (step 1), benzo[1,3]dioxol-5-yl-(3-methyloxetan-3-yl)methanol was prepared. Yield=62%.

Step 2

In a manner analogous to EXAMPLE 1 (step 2), C-benzo[1,3]dioxol-5-yl-C-(3-methyloxetan-3-yl)methylazide was prepared. Yield=33%.

Step 3

In a manner analogous to EXAMPLE 1 (step 3), C-benzo[1,3]dioxol-5-yl-C-(3-methyloxetan-3-yl)methylamine was prepared. Yield=99%.

Step 4

In a manner analogous to EXAMPLE 1 (step 7), 3-(2-{[benzo[1,3]dioxol-5-yl-(3-methyloxetan-3-yl)-methyl]amino}-3,4-dioxocyclobut-1-enylamino)-2-hydroxy-N,N-dimethylbenzamide was prepared. Yield=57%, HPLC 98.0%, ES+ [480].

$^1$H NMR (DMSO-d6, 400 MHz): 1.29 (s, 3H); 2.95 (s, 6H); 4.17 (d, J=6.0 Hz, 2H); 4.28 (d, J=6.1 Hz, 2H); 4.68-473 (m, 2H); 5.51 (d, J=9.8 Hz, 2H); 6.03 (s, 2H); 6.74-6.77 (m, 1H); 6.84-6.95 (m, 4H); 7.71-7.73 (m, 1H); 8.70 (d, 1H) 9.40 (s, 1H); 10.05 (s, 1H).

EXAMPLE 31

Preparation of 3-[3-(3-hydroxypyrrolidine-1-carbonyl)phenylamino]-4-{[(5-methylfuran-2-yl)-(3-methyloxetan-3-yl)methyl]amino}cyclobut-3-ene-1,2-dione

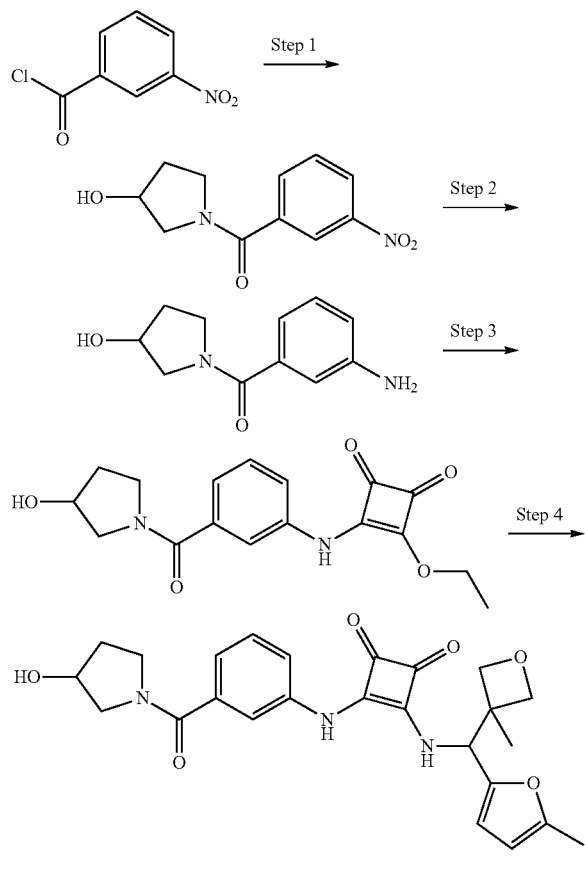

Step 1

(3-Hydroxypyrrolidin-1-yl)-(3-nitrophenyl)methanone 2.22 g of triethylamine (20 mmol), followed by 1.74 g of pyrrolidin-3-ol (20 mmol), were added to a solution of 3.71 g of 3-nitrobenzoyl chloride (20 mmol) in 40 ml of dichloromethane cooled to 0° C. The reaction medium was stirred at ambient temperature for 2 hours and was then diluted with 50 ml of dichloromethane. The organic phase was washed with 50 ml of a 1 N hydrochloric acid solution and then with 50 ml of a saturated sodium hydrogen carbonate solution, dried over magnesium sulfate and evaporated. 3.78 g of (3-hydroxypyrrolidin-1-yl)-(3-nitrophenyl)methanone were obtained and used without purification in the next step. Yield=80%.

Step 2

(3-Aminophenyl)-(3-hydroxypyrrolidin-1-yl)methanone

A mixture of 2.36 g of (3-hydroxypyrrolidin-1-yl)-(3-nitrophenyl)methanone in 40 ml of ethanol and in the presence of 300 mg of palladium on carbon at 10% was stirred under hydrogen atmospheric pressure for 2 days. The reaction medium was filtered through celite and washed with 50 ml of ethanol. The solvent was concentrated to 30 ml. This solution of (3-aminophenyl)-(3-hydroxypyrrolidin-1-yl)methanone was used in the next step. Supposed yield=100%.

Step 3

3-Ethoxy-4-[3-(3-hydroxypyrrolidine-1-carbonyl)phenylamino]cyclobut-3-ene-1,2-dione A mixture of the 30 ml of the solution of (3-aminophenyl)-(3-hydroxypyrrolidin-1-yl)methanone in ethanol and 6.81 g of 3,4-diethoxycyclobut-3-ene-1,2-dione (40.0 mmol, 2.5 eq) was heated at 60° C. overnight. The reaction medium was evaporated and the residue was chromatographed on silica gel eluted with heptane/ethyl acetate at 4/1, 2:1, then dichloromethane/methanol (6%). 3.03 g of 3-ethoxy-4-[3-(3-hydroxypyrrolidine-1-carbonyl)phenylamino]cyclobut-3-ene-1,2-dione were obtained. Yield=63%.

Step 4

3-[3-(3-Hydroxypyrrolidine-1-carbonyl)phenylamino]-4-{[(5-methylfuran-2-yl)-(3-methyloxetan-3-yl)methyl]amino}cyclobut-3-ne-1,2-dione A mixture of 314 mg (1.73 mmol, 1.2 eq) of C-(5-methylfuran-2-yl)-C-(3-methyloxetan-3-yl)methylamine and 500 g (1.44 mmol, 1 eq) of 3-ethoxy-4-[2-hydroxy-3-(3-hydroxypyrrolidine-1-carbonyl)phenylamino]cyclobut-3-ene-1,2-dione in 15 ml of methanol was heated at 50° C. for 6 days. The reaction medium was evaporated and the residue was chromatographed on silica gel HP (column RediSep Rf Gold 40 g, Spot II) eluted with dichloromethane/methanol (gradient).

388 mg of 3-[3-(3-hydroxypyrrolidine-1-carbonyl)phenylamino]-4-{[(5-methylfuran-2-yl)-(3-methyloxetan-3-yl)methyl]amino}cyclobut-3-ene-1,2-dione were obtained in the form of a yellow solid. Yield=58%, Mp=242-245° C., LC/MS: 98.24% [465].

$^1$H NMR (DMSO-d6, 400 MHz): 1.32 (s, 3H); 1.79-1.94 (m, 2H); 2.26 (s, 3H); 3.35-3.43 (m, 2H); 3.50-3.62 (m, 2H); 4.23 & 4.32 (d, J=37.7 Hz, 1H); 4.29 (dd, J=6.2 Hz, 2H); 4.6 (dd, J=24.9 Hz, 2H); 4.95 (d, 1H); 5.59 (d, J=9.6 Hz, 1H);

6.06 (dd, J=3.0 Hz, 1H); 6.28 (d, J=3.1 Hz, 1H); 7.16 (dd, J=7.3 Hz, 1H); 7.40-7.47 (m, 2H); 7.64 (s, 1H); 8.27 (d, J=6.6 Hz, 1H); 9.80 (s, 1H).

EXAMPLE 32

Preparation of methyl 1-[3-(2-{[(5-methylfuran-2-yl)-(3-methyloxetan-3-yl)methyl]amino}-3,4-dioxo-cyclobut-1-enylamino)benzoyl]piperidine-2-carboxylate

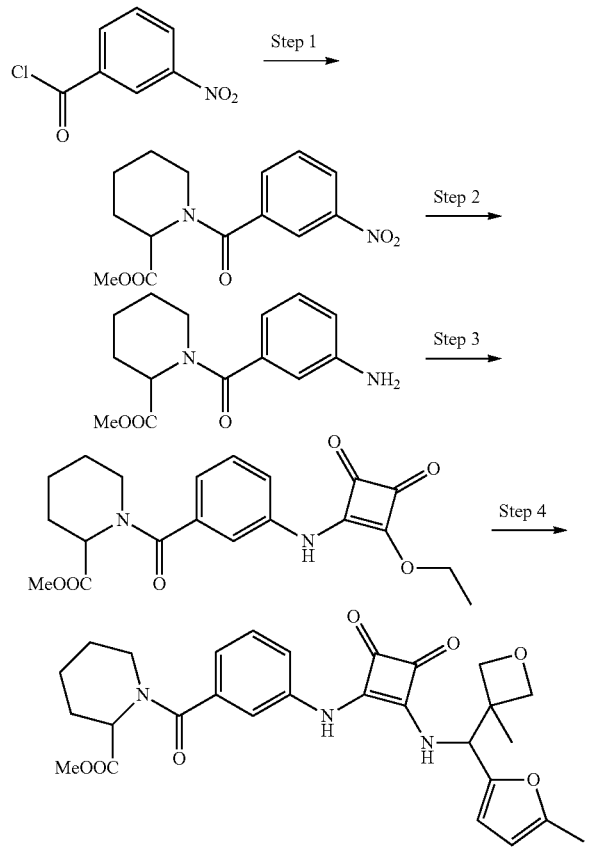

Step 1

In a manner analogous to EXAMPLE 31 (step 1), methyl 1-(3-nitrobenzoyl)piperidine-2-carboxylate was prepared. Yield=84%.

Step 2

In a manner analogous to EXAMPLE 31 (step 2), methyl 1-(3-aminobenzoyl)piperidine-2-carboxylate was prepared. Yield=99%.

Step 3

In a manner analogous to EXAMPLE 31 (step 3), methyl 1-[3-(2-ethoxy-3,4-dioxocyclobut-1-enylamino)benzoyl]piperidine-2-carboxylate was prepared. Yield=81%.

Step 4

In a manner analogous to EXAMPLE 31 (step 4), methyl 1-[3-(2-{[(5-methylfuran-2-yl)-(3-methyloxetan-3-yl)methyl]amino}-3,4-dioxocyclobut-1-enylamino)benzoyl]piperidine-2-carboxylatee was prepared. Yield=52%, Mp=130-132° C., LC/MS: 97.12% [521].

$^1$H NMR (DMSO-d6, 400 MHz): 1.27 (m, 1H); 1.32 (s, 3H); 1.41-1.52 (m, 2H); 1.70 (m, 2H); 2.26 (s, 3H); 3.66-3.73 (d, 3H); 4.30 (dd, J=6.2 Hz, 1H); 4.6 (dd, J=24.6 Hz, 2H); 5.58 (d, J=9.7 Hz, 1H); 6.06 (dd, J=3.0 Hz, 1H); 6.28 (d, J=3.1 Hz, 1H); 7.03 (m, 1H); 7.42-7.51 (m, 3H); 7.64 (s, 1H); 8.27 (d, J=9.8 Hz, 1H); 9.80 (s, 1H).

EXAMPLE 33

Preparation of methyl 1-[3-(2-{[(5-methylfuran-2-yl)-(3-methyloxetan-3-yl)methyl]amino}-3,4-dioxo-cyclobut-1-enylamino)benzoyl]pyrrolidine-2-carboxylate

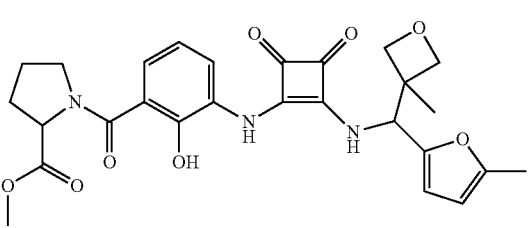 [SMILES: COC(=O)C1CCCN1C(=O)c1cccc(Nc2c(NC(c3ccc(C)o3)C3(C)COC3)c(=O)c2=O)c1O]

In a manner analogous to EXAMPLE 31 (steps 1 to 4), methyl 1-[3-(2-{[(5-methylfuran-2-yl)-(3-methyloxetan-3-yl)methyl]amino}-3,4-dioxocyclobut-1-enylamino)benzoyl]pyrrolidine-2-carboxylate was prepared.

$^1$H NMR (DMSO-d6, 400 MHz): 1.33 (s, 3H); 1.86-1.92 (m, 3H); 2.20-2.30 (m, 1H); 2.26 (s, 3H); 3.54-3.59 (m, 2H); 367 (s, 3H); 4.29-4.30 (dd, 2H); 4.47-4.51 (1H); 4.58 (d, J=6.2 Hz, 1H); 4.64 (d, J=6.3 Hz, 1H); 5.58 (d, J=9.8 Hz, 1H); 6.06 (m, 1H); 6.28 (d, 1H); 7.18 (d, J=7.5 Hz, 1H); 7.42-7.44 (m, 1H); 7.52-7.54 (m, 1H); 7.64 (s, 1H); 7.09-7.11 (d, J=9.8 Hz, 1H); 9.81 (s, 1H).

EXAMPLE 34

Preparation of 2-hydroxy-N,N-dimethyl-3-(2-{[(3-methyloxetan-3-yl)thiophen-2-ylmethyl]amino}-3,4-dioxocyclobut-1-enylamino)benzamide

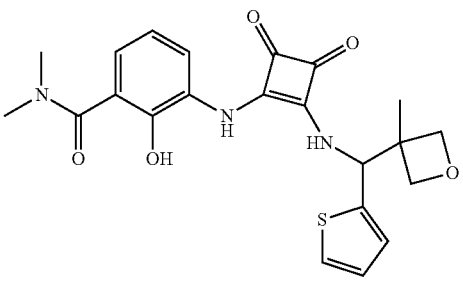 [SMILES: CN(C)C(=O)c1cccc(Nc2c(NC(c3cccs3)C3(C)COC3)c(=O)c2=O)c1O]

In a manner analogous to EXAMPLE 28 (steps 1 to 4), 2-hydroxy-N,N-dimethyl-3-(2-{[(3-methyloxetan-3-yl)thiophen-2-ylmethyl]amino}-3,4-dioxocyclobut-1-enylamino)benzamide was prepared. HPLC 96.6% ES+ [441]

$^1$H NMR (DMSO-d6, 400 MHz): 1.35 (s, 3H); 2.89 (s, 6H); 4.31-4.34 (m, 2H); 4.65-4.69 (m, 2H); 5.95 (d, 1H); 6.88-6.92

(m, 2H); 7.02-7.07 (m, 2H); 7.53-7.55 (d, 1H); 7.74-7.76 (m, 1H); 8.82 (d 1H); 9.45 (s, 1H).

EXAMPLE 35

Preparation of 2-hydroxy-N,N-dimethyl-3-(2-{[(3-methyloxetan-3-yl)-(5-methylthiophen-2-yl)methyl]amino}-3,4-dioxocyclobut-1-enylamino)benzamide

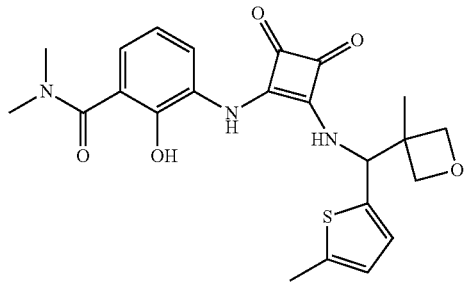 [SMILES: Cc1ccc(C(Nc2c(Nc3cccc(C(=O)N(C)C)c3O)c(=O)c2=O)C2(C)COC2)s1]

In a manner analogous to EXAMPLE 1 (steps 1 to 7), 2-hydroxy-N,N-dimethyl-3-(2-{[(3-methyloxetan-3-yl)-(5-methylthiophen-2-yl)methyl]amino}-3,4-dioxocyclobut-1-enylamino)benzamide was prepared from 2-bromo-5-methylthiophene.

HPLC 98.7%, ES+ [457].

$^1$H NMR (DMSO-d6, 400 MHz): 1.35 (s, 3H); 2.42 (s, 3H); 2.94 (s, 6H); 4.29-4.33 (m, 2H); 4.62-4.67 (m, 2H); 5.84 (d, J=9.7 Hz, 1H); 6.71-6.72 (m, 1H); 6.79 (m, 1H); 6.87-6.90 (d, 2H); 7.73-7.75 (m, 1H); 8.75 (d 1H); 9.43 (s, 1H); 10.00 (s, 1H);

EXAMPLE 36

Preparation of 3-(2-{[furan-2-yl-(3-methyloxetan-3-yl)methyl]amino}-3,4-dioxocyclobut-1-enylamino)-2-hydroxy-N,N-dimethylbenzamide

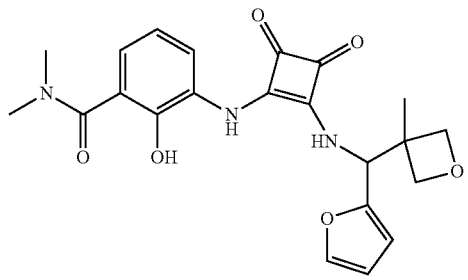 [SMILES: CN(C)C(=O)c1cccc(Nc2c(NC(c3ccco3)C3(C)COC3)c(=O)c2=O)c1O]

In a manner analogous to EXAMPLE 1 (steps 1 to 7), 3-(2-{[furan-2-yl-(3-methyloxetan-3-yl)methyl]amino}-3,4-dioxocyclobut-1-enylamino)-2-hydroxy-N,N-dimethylbenzamide was prepared.

HPLC 96.8%, ES− [424].

$^1$H NMR (DMSO-d6, 400 MHz): 1.30 (s, 3H); 2.94 (s, 6H); 4.31 (d, J=6.2 Hz, 2H); 4.62 (d, J=6.3 Hz, 1H); 4.67 (d, J=6.2 Hz, 1H); 5.71 (d, J=9.7 Hz, 1H); 6.41 (d, J=3.2 Hz, 1H); 6.48 (m, 1H); 6.87-6.92 (m, 2H); 7.71 (m, 1H); 7.75-7.78 (m, 1H); 8.85 (d, J=9.7 Hz, 1H); 9.46 (s, 1H); 10.00 (s, 1H);

EXAMPLE 37a AND 37b

Preparation of (a) 2-hydroxy-N,N-dimethyl-3-(2-{[(4-methylfuran-2-yl)-(3-methyloxetan-3-yl)methyl]amino}-3,4-dioxocyclobut-1-enylamino)benzamide and of (b) 2-Hydroxy-N,N-dimethyl-3-(2-{[(3-methylfuran-2-yl)-(3-methyloxetan-3-yl)methyl]amino}-3,4-dioxocyclobut-1-enylamino)benzamide

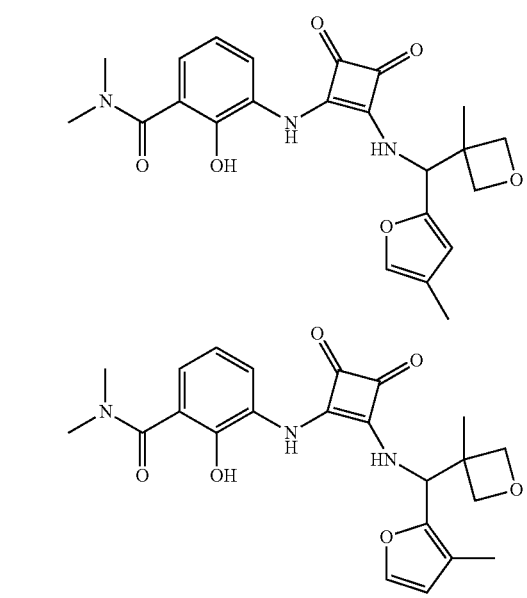

In a manner analogous to EXAMPLE 1 (steps 1 to 7), 2-hydroxy-N,N-dimethyl-3-(2-{[(4-methylfuran-2-yl)-(3-methyloxetan-3-yl)methyl]amino}-3,4-dioxocyclobut-1-enylamino)benzamide and 2-hydroxy-N,N-dimethyl-3-(2-{[(3-methylfuran-2-yl)-(3-methyloxetan-3-yl)methyl]amino}-3,4-dioxocyclobut-1-enylamino)benzamide were prepared from the lithiation of 3-methylfuran which was not regioselective and which takes place at positions 5- and 2-. It should be noted that the separation of the regioisomers was carried out at the azide step by chromatography on silica gel eluted with 95/5 heptane/ethyl acetate.

2-Hydroxy-N,N-dimethyl-3-(2-{[4-methylfuran-2-yl)-(3-methyloxetan-3-yl)methyl]amino}-3,4-dioxocyclobut-1-enylamino)benzamide

HPLC 93.8%, ES+ [440]

$^1$H NMR (DMSO-d6, 400 MHz): 1.30 (s, 3H); 1.97 (s, 3H); 2.95 (s, 6H); 4.30 (d, J=6.1 Hz, 1H); 4.60 (d, J=6.1 Hz, 1H); 4.66 (d, J=6.0 Hz, 1H); 5.65 (d, J=12.2 Hz, 1H); 6.29 (s, 1H); 6.89-6.92 (m, 2H); 7.45 (s, 1H); 7.77 (m, 1H); 8.82 (d, J=9.6 Hz, 1H); 10.05 (s, 1H).

2-Hydroxy-N,N-dimethyl-3-(2-{[(3-methylfuran-2-yl)-(methyloxetan-3-yl)methyl]amino}-3,4-dioxocyclobut-1-enylamino)benzamide

HPLC 88.00%+12%, ES+ [440]

$^1$H NMR (DMSO-d6, 400 MHz): 1.30 (s, 3H); 2.02 (s, 3H); 2.94 (s, 6H); 4.27 (d, J=6.1 Hz, 1H); 4.31 (d, J=6.3 Hz, 1H);

4.48 (d, J=6.1 Hz, 1H); 4.76 (d, J=6.1 Hz, 1H); 5.63 (d, J=9.7 Hz, 1H); 6.36 (s, 1H); 6.87-6.91 (m, 2H); 7.61 (s, 1H); 7.75 (m, 1H); 9.00 (d, J=9.6 Hz, 1H); 9.49 (s, 1H).

EXAMPLE 38

Preparation of 2-hydroxy-N,N-dimethyl-3-(2-{[(4-isopropylfuran-2-yl)-(3-methyloxetan-3-yl)methyl]amino}-3,4-dioxocyclobut-1-enylamino)benzamide

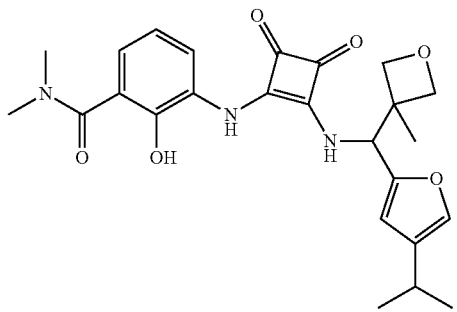 [SMILES: CC(C)c1coc(C(Nc2c(Nc3cccc(C(=O)N(C)C)c3O)c(=O)c2=O)C2(C)COC2)c1]

In a manner analogous to EXAMPLE 1 (steps 1 to 7), 2-hydroxy-3-(2-{[(4-isopropylfuran-2-yl)-(3-methyloxetan-3-yl)-methyl]amino}-3,4-dioxocyclobut-1-enylamino)-N,N-dimethylbenzamide was prepared from 3-isopropylfuran. HPLC 97.2%, ES− [466].

¹H NMR (DMSO-d6, 400 MHz): 1.14 (d, J=6.8 Hz, 3H); 1.30 (s, 3H); 6.68-2.73 (m, 1H); 2.94 (s, 6H); 4.29-4.31 (m, 2H); 4.60 (d, J=6.3 Hz, 1H); 4.65 (d, J=6.2 Hz, 1H); 5.67 (d, J=9.7 Hz, 1H); 6.37 (s, 1H); 6.87-6.90 (m, 2H); 7.44 (s, 1H); 7.76-7.79 (m, 1H); 8.84 (d, J=9.7 Hz, 1H); 9.46 (bs, 1H); 10.00 (s, 1H).

EXAMPLE 39

Preparation of 3-(2-hydroxy-6-methoxypyridin-3-ylamino)-4-{[(5-methylfuran-2-yl)-(3-methyloxetan-3-yl)methyl]amino}cyclobut-3-ene-1,2-dione

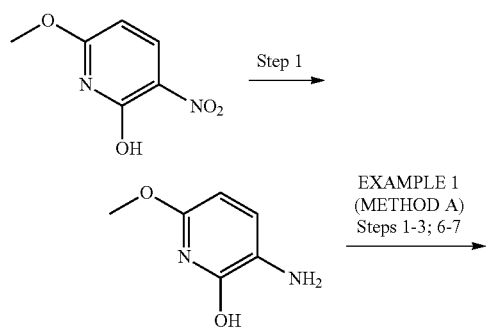

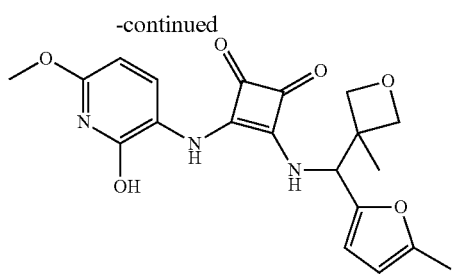

Step 1

3-Amino-6-methoxy-1H-pyridin-2-one 1.0 g of 6-methoxy-3-nitro-1H-pyridin-2-one (5.88 mmol) was dissolved in 16 ml of methanol. The solution was degassed and then palladium on carbon at 10% (0.10 g, 10% by weight) was added thereto. The reaction medium was stirred under a hydrogen atmosphere at 40° C. for 4 hours. The reaction medium was filtered through celite and concentrated to dryness. The residue was chromatographed on silica gel, eluted with 95/5 dichloromethane/methanol. 0.30 g of the compound was isolated. Yield=36%.

In a manner analogous to EXAMPLE 1 (steps 1 to 3, 6 and 7), 3-(2-hydroxy-6-methoxypyridin-3-ylamino)-4-{[(5-methylfuran-2-yl)-(3-methyloxetan-3-yl)methyl]amino}cyclobut-3-ene-1,2-dione was prepared. HPLC 98.8%, ES− [399].

¹H NMR (DMSO-d6, 400 MHz): 1.30 (s, 3H); 2.25 (s, 3H); 3.80 (s, 3H); 4.26-4.29 (m, 2H); 4.56 (d, J=6.2 Hz, 1H); 4.63 (d, J=6.2 Hz, 1H); 5.62 (d, J=9.8 Hz, 1H); 6.05-6.06 (m, 1H); 6.23-6.24 (m, 12H); 8.00 (d, J=8.2 Hz, 1H); 9.40 (s, 1H).

EXAMPLE 40

Preparation of 3-(6-chloro-2-hydroxypyridin-3-ylamino)-4-{[(5-methylfuran-2-yl)-(3-methyloxetan-3-yl)methyl]amino}cyclobut-3-ene-1,2-dione

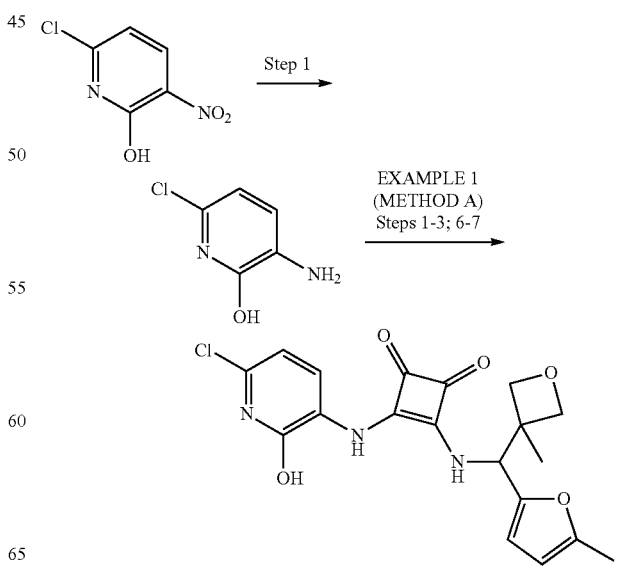

Step 1

3-Amino-6-chloro-1H-pyridin-2-one 9.2 g of tin chloride dihydrate (40.7 mmol, 7 eq) were added portionwise to a solution of 1.0 g of 6-chloro-3-nitro-1H-pyridin-2-one (5.73 mmol) in 15 ml of ethyl acetate. The reaction medium was refluxed for 3 hours, cooled, then diluted with 60 ml of ethyl acetate and neutralized with 14 g of sodium bicarbonate (powder). The reaction medium was filtered. The solid was washed with ethyl acetate (2×15 ml) and the filtrate was concentrated to dryness. The residue was chromatographed on silica gel, eluted with 95/5 dichloromethane/methanol. 0.60 g of product was obtained in the form of a beige solid. Yield=72%.

In a manner analogous to EXAMPLE 1 (steps 1 to 3, 6 and 7), 3-(6-chloro-2-hydroxypyridin-3-ylamino)-4-{[(5-methylfuran-2-yl)-(3-methyloxetan-3-yl)methyl]amino}cyclobut-3-ene-1,2-dione was prepared from 6-chloro-3-nitro-1H-pyridin-2-one. HPLC 94.8%, ES–[402].

$^1$H NMR (DMSO-d6, 400 MHz): 1.37 (s, 3H); 2.32 (s, 3H); 4.33-4.35 (m, 2H); 4.62 (d, J=6.2 Hz, 1H); 4.68 (d, J=62 Hz, 1H); 5.68 (d, J=9.7 Hz, 1H); 6.12 (s, 1H); 6.31 (s, 1H); 8.18 (s, 2H); 9.00 (s, 1H); 9.59 (s, 1H); 12.70-13.00 (s, 1H).

EXAMPLE 41

Preparation of 3-{[(5-methylfuran-2-yl)-(3-methyloxetan-3-yl)methyl]amino}-4-(2-oxo-2,3-dihydro-1H-benzoimidazol-4-ylamino)cyclobut-3-ene-1,2-dione

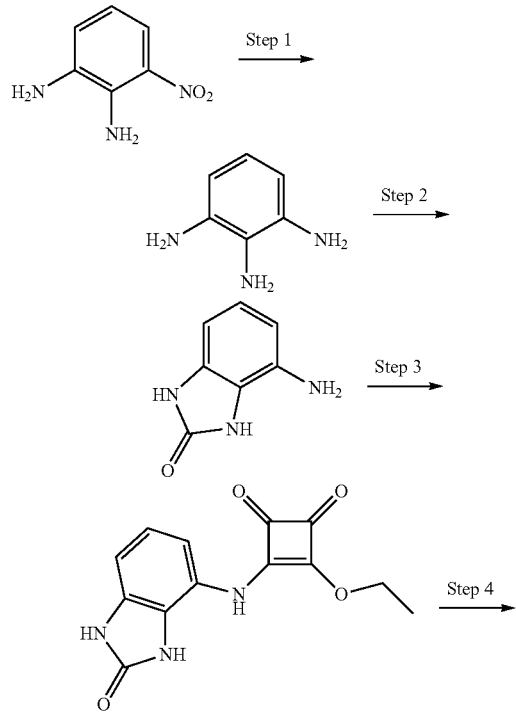

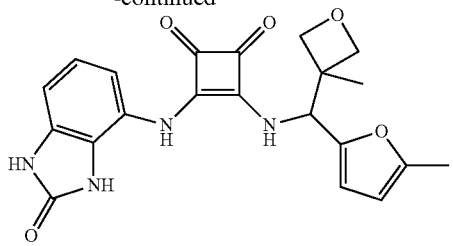

Step 1

Benzene-1,2,3-triamine

A solution of 3-nitrobenzene-1,2-diamine at 0.05 mol/l in methanol was passed through an H-Cube reactor on a cartridge of palladium on carbon with a flow rate of 1 ml/min. After one and a half hours, the product was completely hydrogenated. The solvent was concentrated. 450.7 g of benzene-1,2,3-triamine were obtained in the form of a green oil. Yield>100%.

Step 2

4-Amino-1,3-dihydrobenzoimidazol-2-one 0.53 g (6.5 mmol, 2 eq) of N—N'-carbonyliimidazole were added portionwise to 450.7 mg (3.24 mmol, 1 eq) of benzene-1,2,3-triamine in solution in 30 ml of acetonitrile. The reaction medium was stirred at ambient temperature for 6 hours and then heated at 70° C. overnight. The reaction was stopped by adding 50 ml of water and then extracted with ethyl acetate. The organic phases were combined, and dried over sodium sulfate. The solvents were evaporated off and then the residue was purified by chromatography on silica gel (dichloromethane/methanol/aqueous ammonia: 95/5/2). 229.9 mg of 4-amino-1,3-dihydrobenzoimidazol-2-one were obtained. Yield=42%.

Step 3

3-Ethoxy-4-(2-oxo-2,3-dihydro-1H-benzoimidazol-4-ylamino)cyclobut-3-ene-1,2-dione 0.86 ml of 3,4-diethoxycyclobut-3-ene-1,2-dione (5.9 mmol, 1.5 eq) was added to a solution of 0.59 g of 4-amino-1,3-dihydrobenzoimidazol-2-one (4.0 mmol, 1 eq) in 21 ml of ethanol. The reaction medium was stirred at ambient temperature for 2 days (formation of a precipitate). Ethanol was added in order to promote the fall of the precipitate, which was filtered off, washed with diethyl ether and dried under vacuum at 45° C. The residue was chromatographed on silica gel, eluted with 90/10 dichloromethane/methanol. 0.42 g of product was obtained in the form of a white solid. Yield=38.6%.

Step 4

3-{[(5-Methylfuran-2-yl)-(3-methyloxetan-3-yl)methyl]amino}-4-(2-oxo-2,3-dihydro-1H-benzoimidazol-4-ylamino)cyclobut-3-ene-1,2-dione 0.33 g of C-(5-methylfuran-2-yl)-C-(3-methyloxetan-3-yl)methylamine (1.80 mmol, 1.2 eq) was added to a solution of 0.41 g of 3-ethoxy-4-(2-oxo-2,3-dihydro-1H-benzoimidazol-4-ylamino)cyclobut-3-ene-1,2-dione (1.50 mmol, 1 eq). The reaction medium was heated at 65° C. for 18 hours. The methanol was evaporated off and the residue was chromatographed on silica gel, eluent 95/5 dichloromethane/methanol with 0.1% of triethylamine. The product remains stuck on the silica. The paste obtained was crystallized from diethyl ether, filtered and dried under vacuum at 40° C. 0.11 g of 3-{[(5-methylfuran-2-yl)-(3-methyloxetan-3-yl)methyl]amino}-4-(2-oxo-2,3-dihydro-1H-benzoimidazol-4-ylamino)cyclobut-3-ene-1,2-dione was obtained. Yield=18%. HPLC 94.8%, ES– [407].

$^1$H NMR (DMSO-d6, 400 MHz): 1.32 (s, 3H); 2.26 (s, 3H); 4.28-4.30 (m, 2H); 4.59 (d, J=6.2 Hz, 1H); 4.66 (d, J=6.2 Hz, 1H); 5.59 (d, J=8.0 Hz, 1H); 6.07 (m, 1H); 6.27 (m, 1H); 6.75-6.77 (m, 1H); 6.88-6.94 (m, 2H); 8.16 (s, 1H); 9.28 (s, 1H); 10.72-10.75 (m, 2H).

EXAMPLE 42

Preparation of 2-hydroxy-3-(2-{[(5-methylfuran-2-yl)-(3-methyloxetan-3-yl)methyl]amino}-3,4-dioxocyclobut-1-enylamino)benzonitrile

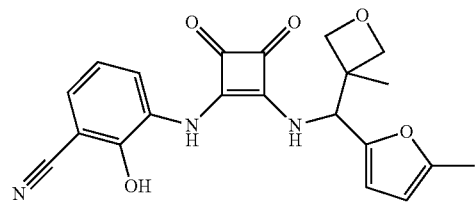 [SMILES: Cc1ccc(C(Nc2c(Nc3cccc(C#N)c3O)c(=O)c2=O)C2(C)COC2)o1]

In a manner analogous to EXAMPLE 1 (steps 1 to 7), 2-hydroxy-3-(2-{[(5-methylfuran-2-yl)-(3-methyloxetan-3-yl)methyl]amino}-3,4-dioxocyclobut-1-enylamino)benzonitrile was prepared from 3-amino-2-hydroxybenzonitrile. HPLC 96.13% ES– [393].

$^1$H NMR (DMSO-d6, 400 MHz): 1.32 (s, 3H); 2.26 (s, 3H); 4.28-4.30 (m, 1H); 4.57 (d, J=6.3 Hz, 1H); 4.64 (d, J=6.2 Hz, 1H); 5.63 (d, J=9.8 Hz, 1H); 6.02 (m, 1H); 6.26 (d, J=3.1 Hz, 1H); 7.00 (s, 1H); 7.30 (s, 1H); 8.03 (d, 1H); 9.85 (d, 1H); 9.50 (s, 1H).

EXAMPLE 43

Preparation of methyl (R)-1-[3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate

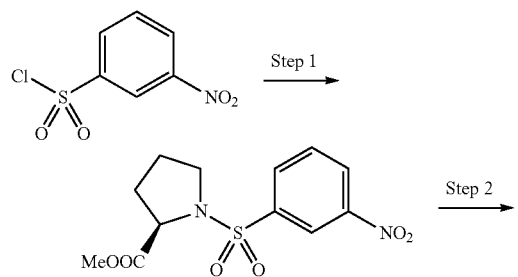

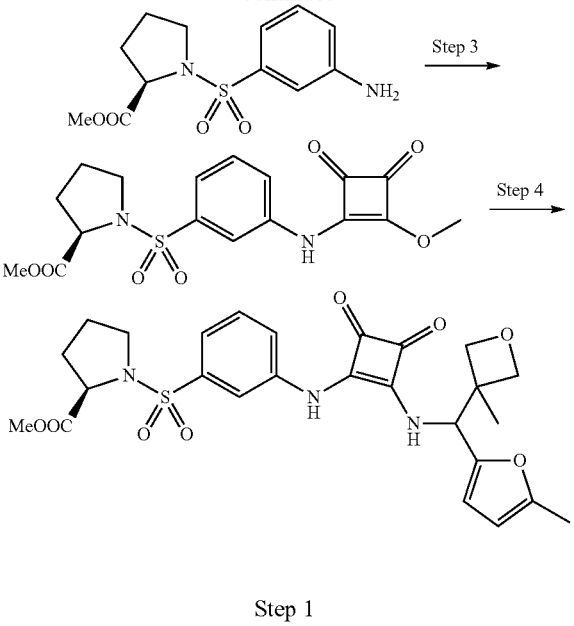

Step 1

Methyl (R)-1-(3-nitrobenzenesulfonyl)pyrrolidine-2-carboxylate 3.38 ml of triethylamine were added dropwise, over the course of 30 minutes, to a solution of 2.56 g of 3-nitrobenzenesulfonyl chloride and 1.91 g of methyl (R)-pyrrolidine-2-carboxylate hydrochloride in 30 ml of dichloromethane (30 ml) cooled to 0° C. The reaction medium was left at ambient temperature and stirred for 1 hour. The reaction medium was diluted with 50 ml of dichloromethane, and washed with a 1 M sodium hydrogen phosphate solution (2×50 ml) and a saturated sodium hydrogen carbonate solution (50 ml). The organic phase was dried over magnesium sulfate and evaporated 3.00 g of methyl (R)-1-(3-nitrobenzenesulfonyl)pyrrolidine-2-carboxylate were obtained and used in the next step without purification.

Step 2

Methyl (R)-1-(3-amino-4-chlorobenzenesulfonyl)pyrrolidine-2-carboxylate

A mixture of 3.0 g of methyl (R)-1-(3-nitrobenzenesulfonyl)pyrrolidine-2-carboxylate in 40 ml of methanol and in the presence of 300 mg of palladium on carbon at 10% (10% by weight) was stirred under hydrogen atmospheric pressure overnight. The reaction medium was filtered through celite and washed with methanol. The solvent was evaporated off. 2.80 g of methyl (R)-1-(3-amino-4-chlorobenzenesulfonyl)pyrrolidine-2-carboxylatee were obtained and used in the next step without purification. Yield=100%.

Step 3

Methyl (R)-1-[3-(2-methoxy-3,4-dioxocyclobut-1-enylamino)benzenesulfonyl]pyrrolidine-2-carboxylate A mixture of 2.54 g of methyl (R)-1-(3-amino-4-chlorobenzenesulfonyl)pyrrolidine-2-carboxylate and 5.68 g of 3,4-dimethoxycyclobut-3-ene-1,2-dione in 50 ml of methanol was heated at 60° C. overnight. The solvent was evaporated off and the residue was chromatographed on silica gel eluted with heptane/ethyl acetate (4:1, 2:1, and pure ethyl acetate). 0.92 g of methyl (R)-1-[3-(2-methoxy-3,4-dioxocyclobut-1-enylamino)benzenesulfonyl]pyrrolidine-2-carboxylate was obtained. Yield=23%.

Step 4

Methyl (R)-1-[3-(2{[(5-methylfuran-2-yl)-(3-methyloxetan-3-yl)methyl]amino}-3,4-dioxocyclobut-1-enylamino)benzenesulfonyl]pyrrolidine-2-carboxylate A mixture of 408.4 mg of methyl (R)-1-[3-(2-methoxy-3,4-dioxocyclobut-1-enylamino)benzenesulfonyl]pyrrolidine-2-carboxylate and 350 mg of C-(5-methylfuran-2-yl)-C-(3-methyloxetan-3-yl)methylamine in 30 ml of ethanol was heated at 60° C. overnight. The solvent was evaporated off and the residue was taken up with 50 ml of ethyl acetate and washed twice with a 1 M sodium hydrogen phosphate solution. The organic phase was dried over magnesium sulfate and evaporated. 432 mg of methyl (R)-1-[3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate were obtained. Yield=79%.

EXAMPLE 44

Preparation of methyl (S)-1-[4-chloro-3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate

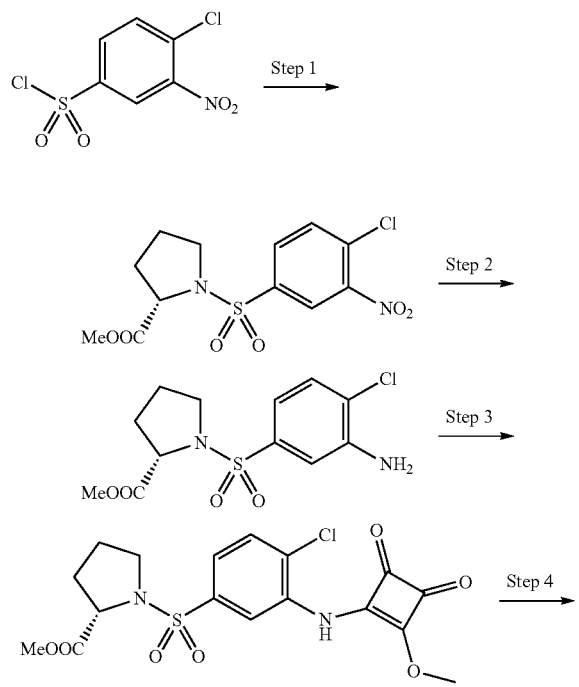

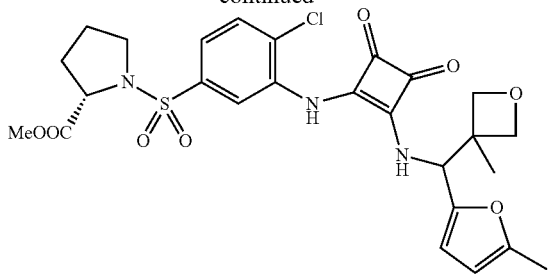

Step 1

Methyl (S)-1-(4-chloro-3-nitrobenzenesulfonyl)pyrrolidine-2-carboxylate

At 0° C., a solution of 0.647 g (3.9 mmol) of methyl (S)-pyrrolidine-2-carboxylate hydrochloride in 6 ml of water was added to 0.83 g of sodium carbonate (7.8 mmol, 2 eq), followed portionwise by 1.0 g (3.9 mmol) of 4-chloro-3-nitrobenzenesulfonyl chloride. The medium was stirred at 0° C. for 4 hours. The reaction medium was diluted with ethyl acetate and brought to pH 5-6 with 2 N HCl. After extraction, the aqueous phase was basified with sodium bicarbonate and extracted twice with ethyl acetate. The organic phases were combined, washed with a saturated sodium chloride solution, dried over magnesium sulfate and evaporated. 1.22 g (90%) of product were obtained. Yield=90%.

Step 2

Methyl (S)-1-(3-amino-4-chlorobenzenesulfonyl)pyrrolidine-2-carboxylate 5.56 g of tin chloride dihydrate (24.63 mmol, 7 eq) were added portionwise to a solution of 1.21 g of 4-chloro-N,N-dimethyl-3-nitro-benzenesulfonamide (3.47 mmol) in 9 ml of ethyl acetate. The reaction medium was refluxed for 3 hours, cooled, then diluted with 12 ml of ethyl acetate and neutralized with 2.50 g of sodium bicarbonate. The reaction medium was filtered. The solid was washed with ethyl acetate (2×15 ml) and the filtrate was concentrated to dryness. The residue was chromatographed on silica gel, eluted with 50/50 dichloromethane/methanol. 0.622 g of product was obtained in the form of a beige solid. Yield=56%.

Step 3

In a manner analogous to EXAMPLE 44 (step 3), methyl (S)-1-[3-(2-methoxy-3,4-dioxocyclobut-1-enylamino)benzenesulfonyl]pyrrolidine-2-carboxylate was prepared. Yield=32%.

Step 4

In a manner analogous to EXAMPLE 44 (step 4), methyl (S)-1-[4-chloro-3-(2-{[(5-methylfuran-2-yl)-(3-methyloxetan-3-yl)methyl]amino}-3,4-dioxocyclobut-1-enylamino)benzenesulfonyl]-pyrrolidine-2-carboxylate was prepared. Yield=87%. HPLC 95.3%, ES– [576].
$^1$H NMR (DMSO-d6, 400 MHz): 1.34 (s, 3H); 1.55-1.70 (m, 1H); 1.75-1.93 (m, 2H); 1.95-2.10 (m, 1H); 2.27 (s, 3H); 3.20-3.33 (m, 1H); 3.35-3.50 (m, 1H); 3.67 (s, 3H); 4.29-4.32 (m, 2H); 4.45-4.55 (m, 1H); 4.59 (d, J=6.0 Hz, 1H); 4.65 (d, J=6.0 Hz, 1H); 5.65 (d, J=9.7 Hz, 1H); 6.09 (s, 1H); 6.30 (d, J=3.0 Hz, 1H); 7.50 (d, 1H); 7.75 (d, J=8.3 Hz, 1H); 8.00 (d, 1H); 8.80 (d, 1H); 9.57 (s, 1H).

EXAMPLE 45

Preparation of methyl (S)-1-[2,6-difluoro-3-(2-{[(5-methylfuran-2-yl)-(3-methyloxetan-3-yl)methyl]amino}-3,4-dioxocyclobut-1-enylamino)benzoyl]pyrrolidine-2-carboxylate

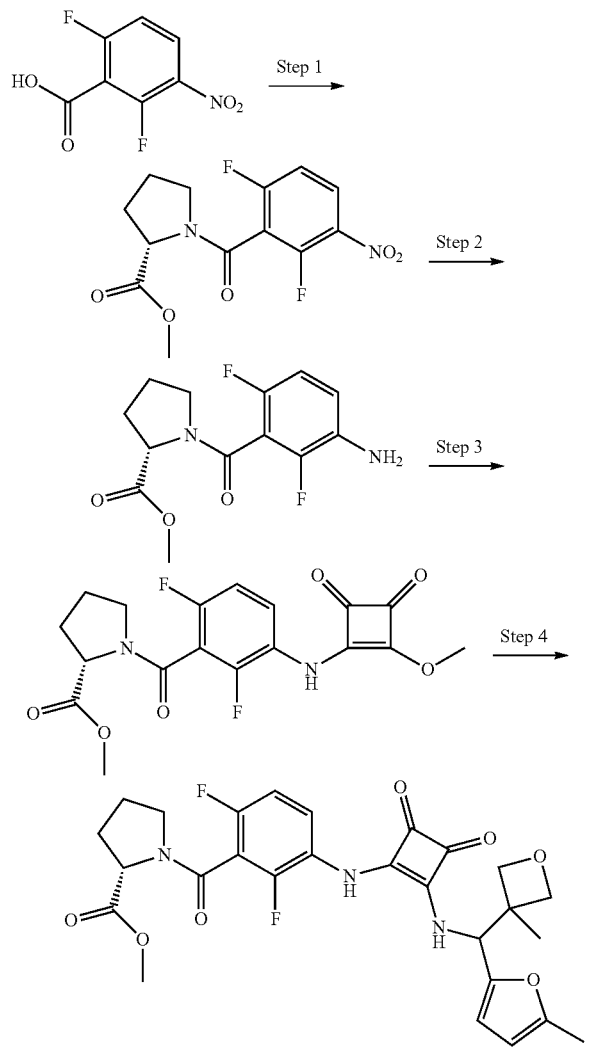

Step 1

Methyl (S)-1-(2,6-difluoro-3-nitrobenzoyl)pyrrolidine-2-carboxylate

A solution of 1.82 g (8.94 mmol) of 2,6-difluoro-3-nitrobenzoic acid in 36 ml of thionyl chloride was refluxed for three and a half hours. The reaction medium was concentrated and was co-evaporated twice with toluene. The residue obtained was dissolved in 50 ml of dichloromethane under nitrogen. 1.48 g (8.94 mmol) of methyl (S)-pyrrolidine-2-carboxylate hydrochloride were added and the reaction medium was cooled to 0° C. 2.75 ml (19.67 mmol, 2.2 eq) of triethylamine were then added dropwise. After 22 hours, a saturated aqueous sodium hydrogen carbonate solution was added. The organic phase was again washed with a saturated aqueous sodium hydrogen carbonate solution and then twice more with a 1 M aqueous hydrochloric acid solution. The organic phase was dried over anhydrous sodium sulfate, filtered and concentrated. 2.52 g were obtained. Yield=83%.

Step 2

Methyl (S)-1-(3-amino-2,6-difluorobenzoyl)pyrrolidine-2-carboxylate 0.71 g (28% by weight) of palladium on carbon at 10% was added to a solution of 2.52 g of methyl (S)-1-(2,6-difluoro-3-nitrobenzoyl)pyrrolidine-2-carboxylate under nitrogen. The reaction medium was stirred under a hydrogen atmosphere for 2 hours. The reaction medium was filtered through celite and concentrated. The residue was used as it is in the next step.

Step 3

Methyl (S)-1-[2,6-difluoro-3-(2-methoxy-3,4-dioxocyclobut-1-enylamino)benzoyl]pyrrolidine-2-carboxylate A mixture of methyl (S)-1-(3-amino-2,6-difluorobenzoyl)pyrrolidine-2-carboxylate (prepared above) and 4.20 g (29.55 mmol) of 3,4-dimethoxycyclobut-3-ene-1,2-dione in solution in 50 ml of methanol was heated at 60° C. for one hour and then stirred at ambient temperature for 4 hours. The reaction medium was concentrated and the residue (6.29 g) was chromatographed on silica gel (300 g prepacked column, eluted with heptane/ethyl acetate, from 70% to 100% of ethyl acetate). 2.30 g of methyl (S)-1-[2,6-difluoro-3-(2-methoxy-3,4-dioxocyclobut-1-enylamino)benzoyl]-pyrrolidine-2-carboxylate were obtained. Yield=79%.

Step 4

Methyl (S)-1-[2,6-difluoro-3-(2-{[(5-methylfuran-2-yl)-(3-methyloxetan-3-yl)methyl]amino}-3,4-dioxocyclobut-1-enylamino)benzoyl]pyrrolidine-2-carboxylate A mixture of 500 mg (1.27 mmol) of methyl (S)-1-[2,6-difluoro-3-(2-methoxy-3,4-dioxocyclobut-1-enylamino)benzoyl]-pyrrolidine-2-carboxylate and 344 mg (1.90 mmol, 1.5 eq) of C-(5-methylfuran-2-yl)-C-(3-methyloxetan-3-yl)methylamine in 25 ml of methanol was heated at 60° C. and was then stirred at ambient temperature overnight. The reaction medium was concentrated. The residue was taken up with ethyl acetate and was washed twice with a 1 M aqueous sodium dihydrogen phosphate solution. The organic phase was dried over anhydrous sodium sulfate, filtered and concentrated. 0.64 g of methyl (S)-1-[2,6-difluoro-3-(2-{[(5-methylfuran-2-yl)-(3-methyloxetan-3-yl)methyl]amino}-3,4-dioxocyclobut-1-enylamino)benzoyl]pyrrolidine-2-carboxylate was obtained. Yield=93%, Mp=122° C.

$^1$H NMR (DMSO-d6, 400 MHz): (presence of two conformers, description of the principal conformer): 1.33 (s, 3H); 1.80-2.10 (m, 3H); 2.15-2.35 (m, 4H); 3.30-3.50 (m, 2H); 3.68 (s, 3H); 4.28-4.31 (m, 2H); 4.53-4.58 (m, 2H); 4.64 (d, J=6.2 Hz, 1H); 5.61 (d, J=9.7 Hz, 1H); 6.07 (d, J=2.0 Hz, 1H);

6.28 (d, J=2.9 Hz, 1H); 7.28 (t, J=8.4 Hz, 1H); 7.95-8.15 (m, 1H); 8.55-8.65 (m, 1H); 9.68 (m, 1H).

EXAMPLE 46

Preparation of methyl (S)-1-[2-chloro-3-(2-{[(5-methylfuran-2-yl)-(3-methyloxetan-3-yl)methyl]amino}-3,4-dioxocyclobut-1-enylamino)benzoyl]pyrrolidine-2-carboxylate

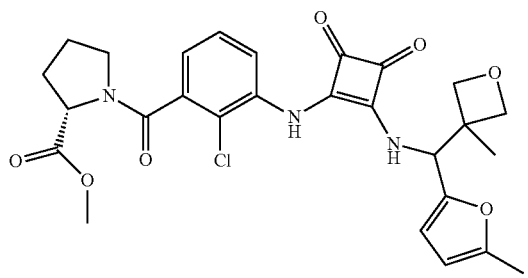 [SMILES: COC(=O)[C@@H]1CCCN1C(=O)c1cccc(Nc2c(NC(c3ccc(C)o3)C3(C)COC3)c(=O)c2=O)c1Cl]

Step 1

In a manner analogous to EXAMPLE 46 (step 1), methyl (S)-1-(2-chloro-3-nitrobenzoyl)pyrrolidine-2-carboxylate was prepared.

Step 2

A solution of 2.64 g of methyl (S)-1-(2-chloro-3-nitrobenzoyl)pyrrolidine-2-carboxylate and 10.0 g of tin chloride in 60 ml of methanol was refluxed for 1 hour. The reaction medium was filtered and the filtrate was concentrated by half its volume and extracted with ethyl acetate (3×50 ml). The organic phases were combined, dried over magnesium sulfate and evaporated. 2.20 g of methyl (S)-1-(3-amino-2-chlorobenzoyl)pyrrolidine-2-carboxylate were obtained. Yield=92%.

Step 3

In a manner analogous to EXAMPLE 46 (step 3), methyl (S)-1-[2-chloro-3-(2-methoxy-3,4-dioxocyclobut-1-enylamino)benzoyl]-pyrrolidine-2-carboxylate was prepared.

Step 4

In a manner analogous to EXAMPLE 46 (step 4), methyl (S)-1-[2-chloro-3-(2-{[(5-methylfuran-2-yl)-(3-methyloxetan-3-yl)methyl]amino}-3,4-dioxocyclobut-1-enylamino)benzoyl]pyrrolidine-2-carboxylate was prepared. Yield=83%. Mp=148-158° C., LC/MS: 99.47% [541].

$^1$H NMR (DMSO-d6, 400 MHz): (presence of two conformers, description of the principal conformer): 1.35 (s, 3H); 1.80-2.05 (m, 3H); 2.15-2.35 (m, 4H); 3.20-3.30 (m, 2H); 3.70 (s, 3H); 4.30 (t, J=6.2 Hz, 2H); 4.49-4.52 (m, 1H); 4.58 (d, J=6.2 Hz, 1H); 4.65 (d, J=6.2 Hz, 1H); 5.65 (d, J=0.7 Hz, 1H); 6.08 (dd, J=3.0-0.9 Hz, 1H); 6.29 (d, J=3.0 Hz, 1H); 7.06 (d, J=7.4 Hz, 1H); 7.43 (t, J=7.9 Hz, 1H); 7.67 (d, J=8.2 Hz, 1H); 8.77 (d, J=9.9 Hz, 1H); 9.46 (s, 1H).

EXAMPLE 47

Preparation of methyl (R)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate

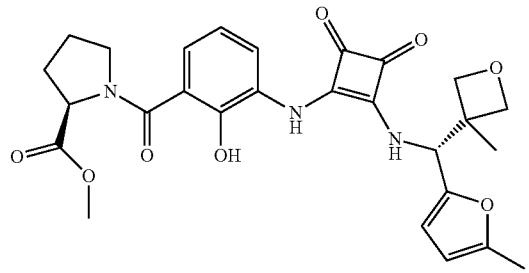 [SMILES: COC(=O)[C@H]1CCCN1C(=O)c1cccc(Nc2c(N[C@@H](c3ccc(C)o3)C3(C)COC3)c(=O)c2=O)c1O]

In a manner analogous to EXAMPLE 7 (steps 1 to 4), methyl (R)-1-[2-hydroxy-3-(2-{[(R)-(5-methylfuran-2-yl)-(3-methyloxetan-3-yl)-methyl]amino}-3,4-dioxocyclobut-1-enylamino)benzoyl]pyrrolidine-2-carboxylate was prepared. Mp=140° C., HPLC: 99.31%, ES+ [524]

$^1$H NMR (DMSO-d6, 400 MHz): presence of two conformers, description of the major conformer at approximately 80%: 1.32 (s, 3H), 1.80-2.00 (m, 3H), 2.15-2.35 (m, 4H), 3.55-3.75 (m, 5H), 4.27-4.30 (m, 2H), 4.50-4.60 (m, 2H), 4.65 (d, J=6.2 Hz, 1H), 5.64 (d, J=9.8 Hz, 1H), 6.06 (dd, J=3.1 Hz, J=1.0 Hz, 1H), 6.26 (d, J=3.1 Hz, 1H), 6.93 (t, J=7.9 Hz, 1H), 7.14 (bd, J=7.52 Hz, 1H), 7.86 (bd, J=7.8 Hz, 1H), 8.84 (bd, J=9.72 Hz, 1H), 9.49 (bs, 1H).

EXAMPLE 48

Preparation of 2-hydroxy-N-methyl-3-(2-{[(R)-(5-methylfuran-2-yl)-(3-methyloxetan-3-yl)methyl]amino}-3,4-dioxocyclobut-1-enylamino)-N-(2,2,2-trifluoroethyl)benzamide

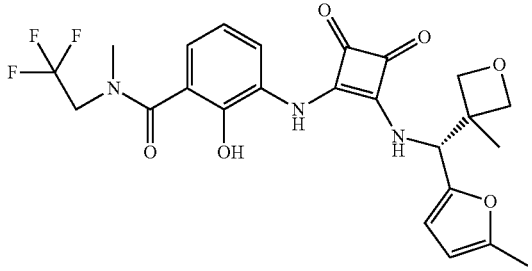 [SMILES: Cc1ccc([C@H](Nc2c(Nc3cccc(C(=O)N(C)CC(F)(F)F)c3O)c(=O)c2=O)C2(C)COC2)o1]

In a manner analogous to EXAMPLE 7 (steps 1 to 4), 2-hydroxy-N-methyl-3-(2-{[(R)-(5-methylfuran-2-yl)-(3-methyloxetan-3-yl)methyl]amino}-3,4-dioxocyclobut-1-enylamino)-N-(2,2,2-trifluoroethyl)benzamide was prepared. Mp=123° C., HPLC: 99.53%, ES+ [508]

$^1$H NMR (DMSO-d6, 400 MHz): 1.32 (s, 3H), 2.26 (s, 3H), 2.85-3.15 (m, 3H), 3.90-4.45 (m, 4H), 4.58 (d, J=6.2 Hz, 1H), 4.65 (d, J=6.2 Hz, 1H), 5.64 (d, J=9.8 Hz, 1H), 6.06 (dd, J=3.0, J=3.0 Hz, 1H), 6.26 (d, J=3.1 Hz, 1H), 6.84 (dd, J=7.6

Hz, J=1.5 Hz, 1H), 6.94 (t, J=7.8 Hz, 1H), 7.76 (dd, J=8.0 Hz, J=1.1 Hz, 1H), 8.79 (d, J=9.8 Hz, 1H), 9.45-9.55 (m, 1H), 9.75-10.00 (m, 1H).

EXAMPLE 49

Preparation of 2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide

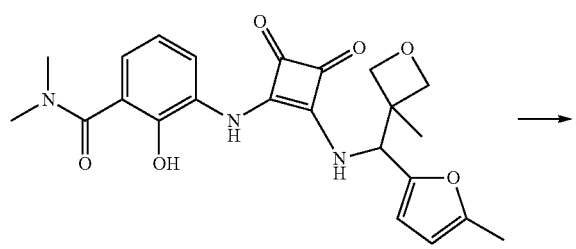

→

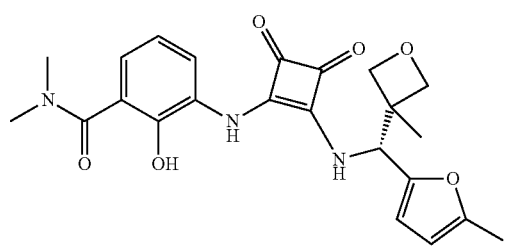

(R)

+

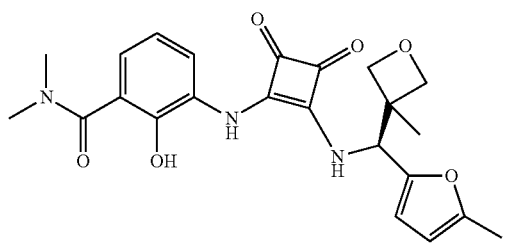

(S)

Using the 2-hydroxy-N,N-dimethyl-3-(2-{[(5-methylfuran-2-yl)-(3-methyloxetan-3-yl)methyl]amino}-3,4-dioxocyclobut-1-enylamino)benzamide obtained in example 1, a chiral separation was carried out on 130 mg dissolved in 4 ml of ethanol.

The separation is carried out on the Chiralpack IA column eluted with heptane/ethanol (90/10) over the course of 80 minutes with a flow rate of 12 ml/min. The injections were of 800 µl (15-20 mg). Two fractions of 23 mg of each enantiomer were obtained:

(R)-enantiomer: 27.1 min, LC/MS: 99.8% [439], (S)-enantiomer: 33.7 min, LC/MS: 99.5% [439].

$^1$H NMR (DMSO-d6, 400 MHz) (R)- or (S)-enantiomer: 1.32 (s, 3H); 2.26 (s, 3H); 2.94 (s, 6H); 4.29 (dd, J=6.2 Hz, 2H); 4.6 (dd, J=28.8 Hz, 2H); 5.6 (d, J=9.7 Hz, 1H); 6.06 (d, J=2.1 Hz, 1H), 6.25 (d, J=3.1 Hz, 1H); 6.88 (m, 2H); 7.76 (q, J=9.5 Hz, 1H); 8.83 (d, J=9.8 Hz, 1H); 9.46 (s, 1H).

EXAMPLE 50

Preparation of 2-hydroxy-N,N-dimethyl-3-(2-{[((R)-5-methylfuran-2-yl)-(3-methyloxetan-3-yl)methyl]amino}-3,4-dioxocyclobut-1-enylamino)benzamide

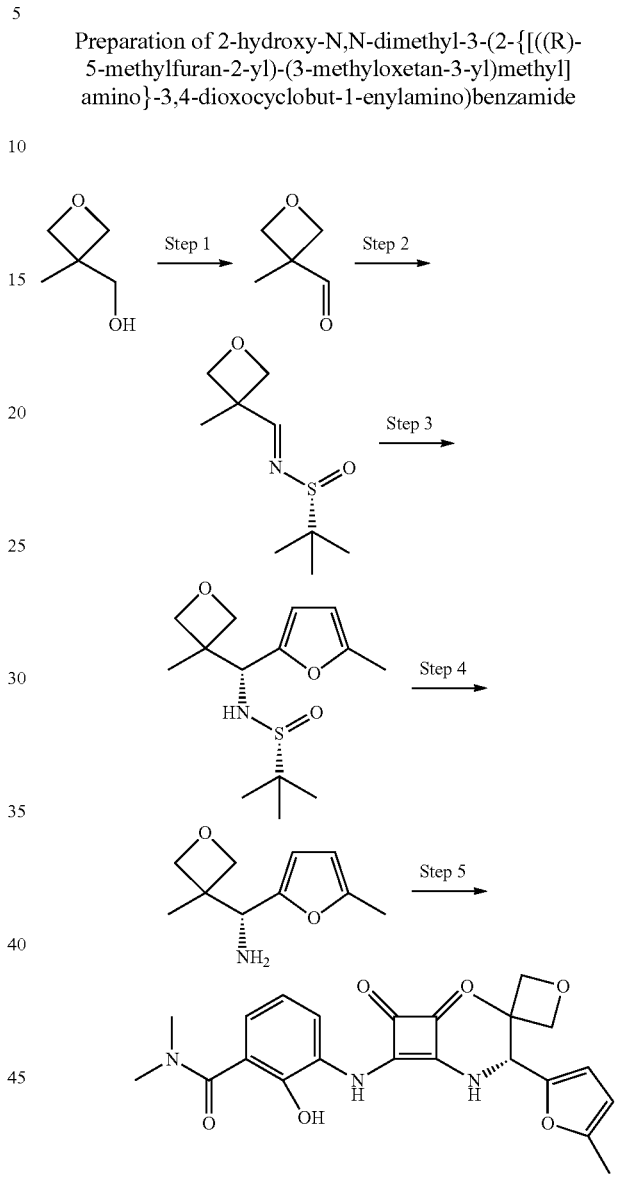

Step 1 (Method a)

3-Methyloxetane-3-carbaldehyde 6.8 ml (80 mmol, 1.6 eq) of oxalyl chloride were added dropwise to a solution of 135 ml of dichloromethane cooled to −78° C. (acetone/dry ice bath), followed by 12 ml of dimethyl sulfoxide (0.17 mmol, 3.3 eq) dropwise (attention, large amount of toxic carbon monoxide gas given off). The reaction medium was stirred 15 minutes at −78° C. A solution of 5.0 ml (50 mmol, 1 eq) of (3-methyloxetan-3-yl)methanol in 110 ml of dichloromethane was added dropwise over the course of 30 minutes at −78° C. (the temperature of the reaction medium reaches −55° C.) and the reaction medium was stirred at −70° C. for one and a half hours. 44 ml of N,N-diisopropylethylamine (0.25 mol, 5.0 eq) were added dropwise (the temperature of the reaction medium reaches −25° C.). The cooling bath was removed and the reaction medium was gently brought back to ambient temperature and stirred for 30 minutes (similar yield when leaving to stir overnight). The reaction was stopped by adding 150 ml of a 10% sodium bisulfate solution with vigorous stirring and taking care to keep the pH of the aqueous phase below 5. The reaction medium was poured into 200 ml of dichloromethane and separated by settling out. 100 ml of a saturated sodium chloride solution were added to the aqueous phase and then the latter was extracted with dichloromethane (3×100 ml). The organic phases were combined, dried over magnesium sulfate, filtered and evaporated (260 mmHg, water bath at 40° C.). 41.5 g of crude product were obtained. It was important not to concentrate too much, because the aldehyde formed was very volatile.

Step 1 (Method b)

3-Methyloxetane-3-carbaldehyde

A solution of (3-methyloxetan-3-yl)methanol (20.4 g, 0.2 mol) in 200 ml of dichloromethane was added dropwise to a mixture of pyridinium chlorochromate (68.9 g, 0.32 mol) and celite (20.4 g) in 700 ml of dichloromethane. The reaction medium was stirred at ambient temperature for 5 hours. The reaction medium was filtered on 250 g of silica and diluted with dichloromethane. The organic phases were combined and evaporated at 30° C. at ~500 mbar then 3 times 30 seconds at 10° C. at ~30 mbar. 12.42 g of 3-methyloxetan-3-carbaldehyde were obtained in the form of a volatile pale green oil. Yield=62%.

Step 2

(R)-2-Methylpropane-2-sulfinic acid 1-(3-methyloxetan-3-yl)meth-(E)-ylideneamide 18 ml of titanium(IV) ethoxide (86 mmol, 2 eq) were added to 46 g of 3-methyloxetane-3-carbaldehyde at 9.7% (45 mmol, 1 eq) cooled to 5° C. The reaction medium was stirred for 10 minutes. 5.73 g of (R)-(+)-2-methyl-2-propanesulfinamide (47.3 mmol, 1.1 eq) were added and the reaction medium was stirred for 16 hours. 5.54 g of sodium sulfate decahydrate (17.2 mmol) were ground to a powder and added to the reaction medium. The reaction medium was stirred vigorously for 20 minutes and 400 ml of ethyl acetate were added and the stirring was maintained for 30 minutes. 100 ml of celite and 20 g of sodium sulfate were added and the reaction medium was stirred for 10 minutes. The suspension was filtered through 100 ml of celite and the cake was washed with ethyl acetate (2×100 ml). The filtrate was evaporated under reduced pressure to give 19.2 g of a brown oil which was purified on a silica column eluted with heptane/ethyl acetate. 8.38 g of (R)-2-methylpropane-2-sulfinic acid 1-(3-methyloxetan-3-yl)meth-(E)-ylideneamide were obtained in the form of a pale yellow solid. Yield=90%, 81% over 2 steps).

Step 3

(R)-2-Methylpropane-2-sulfinic acid [(R)-(5-methylfuran-2-yl)-(3-methyloxetan-3-yl)methyl]amide 23 ml of butyllithium at 2.7 M in hexane (62 mmol, 1.4 eq) were added dropwise over the course of 5 minutes to a solution of 6.8 ml of 2-methylfuran (75 mmol, 1.7 eq) dans 38 ml of diethyl ether cooled to 5° C. The ice bath was removed and the orange solution was stirred for one and a half hours at ambient temperature. The reaction medium was cooled to 5° C. and 16.0 g of solid magnesium bromide ethyl etherate (62.1 mmol, 1.4 eq) were added. The ice bath was removed and the suspension obtained was stirred at ambient temperature for 45 minutes and separated into 2 phases once the stirring stopped (pale yellow upper phase and brown lower phase with a few insoluble white crystals). 9.0 g of sulfinylimine (44.3 mmol, 1 eq) and 240 ml of toluene were placed in a 1 liter three-necked flask equipped with a mechanical stirring system. The mixture was cooled to −70° C. (acetone-dry ice bath) and the Grignard reagent was transferred onto the sulfinylimine via a pipe over the course of 30 minutes.

The reaction medium was allowed to return to ambient temperature slowly and stirred for 16 hours. The reaction medium was cooled to 5° C. and 100 ml of a saturated ammonium chloride solution were added in order to hydrolyze the Grignard reagent. The reaction medium was allowed to return to ambient temperature and 10 ml of water were added in order to dissolve the salts present. The reaction medium was separated by settling out and the aqueous phase was extracted with t-butyl methyl ether (100 ml). The organic phases were combined, dried over sodium sulfate, filtered and evaporated. 13.5 g were obtained in the form of an orange oil. Analysis of the crude product by $^1$H NMR shows that there is less than 5% of unwanted diastereoisomer. Purification on a silica column eluted with heptane/ethyl acetate makes it possible to obtain 11.5 g of (R)-2-methylpropane-2-sulfinic acid [(R)-(5-methylfuran-2-yl)-(3-methyloxetan-3-yl)methyl]amide in the form of an orange oil which later crystallizes. Yield=91%.

Step 4

C—[(R)—C-(5-Methylfuran-2-yl)-C-(3-methyloxetan-3-yl)]methylamine 14.5 g of protected amine (51.0 mmol, 1 eq) and 255 ml of cyclopentyl methyl ether (CPME) were placed in a 1 liter three-necked flask equipped with a mechanical stirring system. The mixture was cooled to −40° C. (acetone-dry ice bath) and 78 ml of a 1.2 M solution of hydrogen chloride in CPME (94 mmol, 1.85 eq) were added dropwise via a pipe over the course of 30 minutes.

The reaction medium was stirred for one and a half hours (temperature increased to 10° C.). A TLC control (2/1 ethyl acetate/heptane) showed that starting material remained. The reaction medium was filtered through celite (300 ml) and the cake was washed with CPME (4×50 ml). The receptacle was changed and the cake was washed with methanol (5×100 ml). The filtrate was evaporated to give 15 g of a light brown paste. Analysis of the crude product by $^1$H NMR (CD$_3$OD) shows that there is 10-15% of by-product originating from the opening of the oxetane (2 diastereoisomers). 200 ml of isopropanol were added, the solid was broken into small pieces and the suspension was partially concentrated to remove 75 ml of solvent. The suspension was then stirred at ambient temperature for 3 hours and filtered. The cake was washed with isopropanol (2×20 ml). 8.9 g of wet white solid were obtained in hydrochloride salt form, determined by $^1$H NMR (CD$_3$OD) analysis. The free amine was obtained by stirring the hydrochloride salt in a solution of 2 M sodium hydroxide (80 ml) and of t-butyl methyl ether (100 ml) for 30 minutes. The heterogeneous medium was separated by settling out and the aqueous phase was extracted with t-butyl methyl ether (3×100 ml). The organic phases were combined, dried over sodium sulfate, filtered and evaporated. The residue was dried under vacuum (ca. 1 mm Hg) for 1 hour. 5.22 g of product were obtained in the form of a yellow oil. Yield=56%. $[\alpha]_D$–12.8 (c=1.9, CHCl$_3$).

Step 5

2-Hydroxy-N,N-dimethyl-3-(2-{[(R)-(5-methylfuran-2-yl)-(3-methyloxetan-3-yl)methyl]amino}-3,4-dioxocyclobut-1-enylamino)benzamide 471 mg (2.6 mmol, 1.3 eq) of C—(R)-(5-methylfuran-2-yl)-C-(3-methyloxetan-3-yl)methylamine were added to 609 mg (2.0 mmol, 1 eq) of 3-(2-ethoxy-3,4-dioxocyclobut-1-enylamino)-2-hydroxy-N,N-dimethylbenzamide dissolved under hot conditions in 40 ml of methanol. The reaction medium was heated at 50° C. for 17 hours. The methanol was evaporated off and the residue (green oil) was chromatographed on silica gel (column puriFlash IR-50SI-80G, Spot II) eluted with dichloromethane/methanol (97/3). The amorphous solid was taken up with diethyl ether to give a yellow powder which was recrystallized from n-propanol. 519 mg of 2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide were obtained. Yield=70%.

EXAMPLE 51

Preparation of methyl {[2-hydroxy-3-(2-{[(R)-(5-methylfuran-2-yl)-(3-methyloxetan-3-yl)methyl]amino}-3,4-dioxocyclobut-1-enylamino)benzoyl]methylamino}acetate

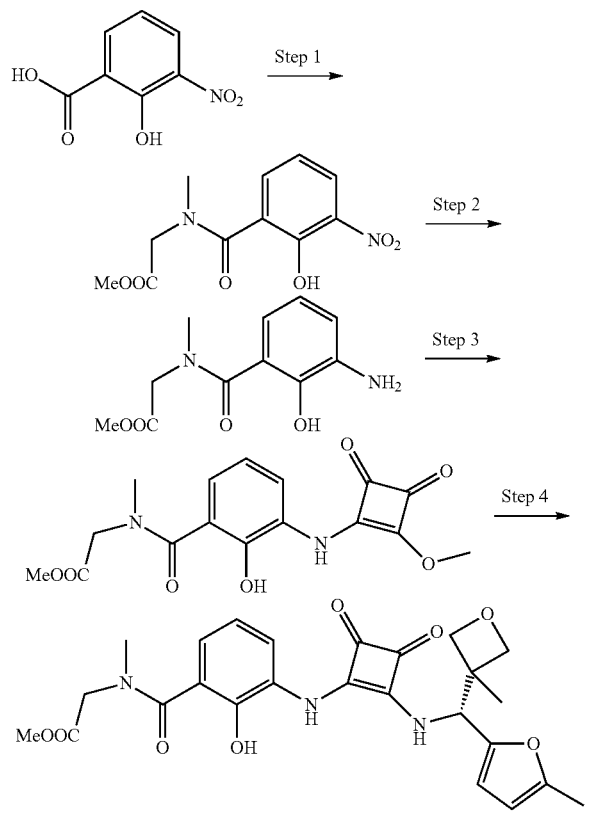

Step 1

Methyl[(2-hydroxy-3-nitrobenzoyl)methylamino]acetate 18.8 ml (109.2 mmol, 4 eq) of N,N-diisopropylamine and then 7.62 g (54.6 mmol, 2 eq) of methyl methylaminoacetate hydrochloride were added to a mixture of 25.46 g (54.6 mmol, 2 eq) of bromotrispyrrolidinophosphonium hexafluorophosphate and 5.0 g (27.30 mmol, 1 eq) of 3-nitrosalicylic acid in 75.00 ml of dichloromethane under nitrogen. The reaction medium was stirred at ambient temperature for 22 hours. The reaction medium was washed three times with a 1 M aqueous hydrochloric acid solution. The organic phase was dried over anhydrous sodium sulfate, filtered and concentrated. The residue (30 g) was chromatographed on silica gel (800 g prepacked column, eluent heptane/ethyl acetate from 40% to 100% of ethyl acetate, 200 ml/min).

5.85 g of methyl[(2-hydroxy-3-nitrobenzoyl)methylamino]acetate were obtained in the form of a yellow oil. Yield=79.88%.

Step 2

Methyl[(3-amino-2-hydroxybenzoyl)methylamino]acetate

A solution of 5.78 g (21.5 mmol, 1 eq) of methyl[(2-hydroxy-3-nitrobenzoyl)methylamino]acetate in 75 ml of methanol in the presence of 0.52 g (10% by weight) of Pd/C 10% was stirred at hydrogen atmospheric pressure for two and a half hours. The reaction medium was filtered through celite and the filtrate was evaporated. The residue (4.78 g) was chromatographed on silica gel (300 g prepacked column, eluent heptane/ethyl acetate from 40% to 90% of ethyl acetate, 120 ml/min). 3.92 g of methyl[(3-amino-2-hydroxybenzoyl)methylamino]acetate were obtained in the form of a yellow oil. Yield=76%.

Step 3

Methyl {[2-hydroxy-3-(2-methoxy-3,4-dioxocyclobut-1-enylamino)benzoyl]methylamino}acetate A mixture of 3.92 g (16.4 mmol, 1 eq) of methyl[(3-amino-2-hydroxybenzoyl)methylamino]acetate and 4.68 g (32.9 mmol, 1 eq) of 3,4-dimethoxy-3-cyclobutene-1,2-dione was stirred at ambient temperature for 24 hours. The solvent was evaporated off and the residue was chromatographed on silica gel (200 g prepacked column, eluent 20/80 then 0/100 heptane/ethyl acetate). 3.49 g of methyl {[2-hydroxy-3-(2-methoxy-3,4-dioxocyclobut-1-enylamino)benzoyl]methylamino}acetate were obtained in the form of a white solid. Yield=61%.

Step 4

Methyl {[2-hydroxy-3-(2-{[(R)-(5-methylfuran-2-yl)-(3-methyloxetan-3-yl)methyl]amino}-3,4-dioxocyclobut-1-enylamino)benzoyl]methylamino}acetate A mixture of 371 mg (2.07 mmol, 1.2 eq) of C—(R)-(5-methylfuran-2-yl)-C-(3-methyloxetan-3-yl)methylamine (prepared in EXAMPLE 50, steps 1 to 4) and 600 mg (1.7 mmol, 1 eq) of methyl {[2-hydroxy-3-(2-methoxy-3,4-dioxocyclobut-1-enylamino)benzoyl]methylamino}acetate in 24 ml of methanol was heated at 60° C. for 16 hours. The methanol was evaporated off and the residue was chromatographed on silica gel, eluent dichloromethane/ethyl acetate (75/25). The paste obtained was crystallized from diethyl ether and heptane and dried under vacuum at 40° C. 660 mg of methyl {[2-hydroxy-3-(2-{[(R)-(5-methylfuran-2-yl)-(3-methyloxetan-3-yl)methyl]amino}-3,4-dioxocyclobut-1-enylamino)benzoyl]methylamino}acetate were obtained in the form of a pale yellow solid. Yield=76%.

$^1$H NMR (DMSO-d6, 400 MHz): 1.33 (s, 3H); 2.26 (s, 3H); 2.96 (bs, 3H); 3.67 (s, 3H); 4.80 (bs, 1H); 4.28 (d, j=6.2 Hz, 2H); 4.29 (d, j=6.2 Hz, 1H); 4.88 (d, j=6.2 Hz, 1H); 4.65 (d, j=6.2 Hz, 1H); 5.65 (d, j=9.8 Hz, 1H); 6.06 (m, 1H); 6.26 (m, 1H); 6.85 (bs, 1H); 6.88-6.93 (m, 1H); 7.78 (d, j=7.7 Hz, 1H); 8.83 (d, j=9.8 Hz, 1H); 9.46 (s, 1H); 9.87 (bs, 1H).

EXAMPLE 52

Preparation of 6-chloro-2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide

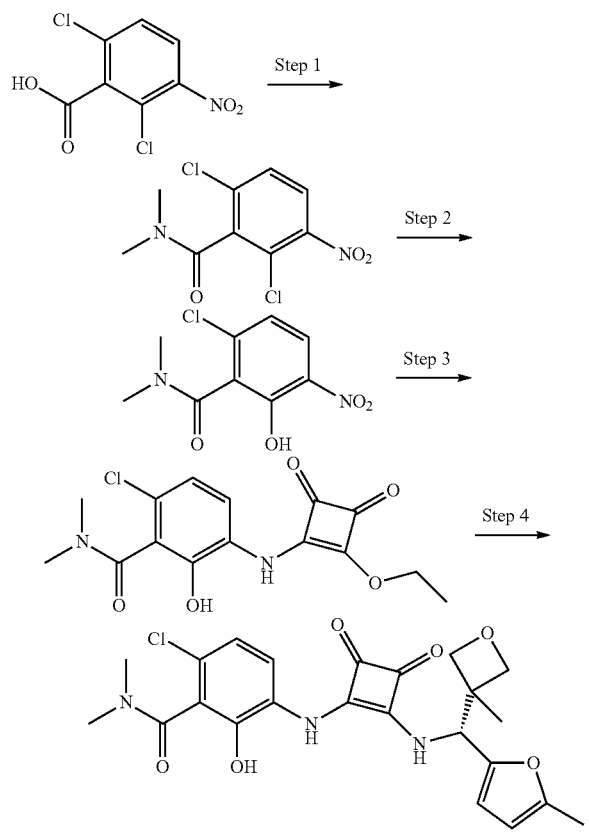

Step 1

2,6-Dichloro-N,N-dimethyl-3-nitrobenzamide

A solution of 10.0 g (42.4 mmol, 1 eq) of 2,6-dichloro-3-nitrobenzoic acid in 50 ml of thionyl chloride was refluxed for 2 hours. The reaction medium was concentrated and co-evaporated with toluene. The residue was taken up in 35 ml of tetrahydrofuran and then 48 ml of a solution of dimethylamine in tetrahydrofuran was added dropwise. After 20 minutes of stirring at ambient temperature, water was added, as was ethyl acetate. The organic phase was again washed with water, dried over anhydrous sodium sulfate, filtered and concentrated. 11.36 g of 2,6-dichloro-N,N-dimethyl-3-nitrobenzamide were obtained in the form of a yellow oil. Quantitative yield.

Step 2

6-Chloro-2-hydroxy-N,N-dimethyl-3-nitrobenzamide 3.2 ml (177.6 mmol, 4.2 eq) of water and 11.04 g (41.96 mmol; 1.0 eq) of 2,6-dichloro-N,N-dimethyl-3-nitrobenzamide (41.96 mmol; 1.00 eq.) in solution in 130.00 ml of tetrahydrofuran were added to a suspension of 7.16 g (179.01 mmol; 4.3 eq) sodium hydride in 250 ml of tetrahydrofuran cooled to 0° C. After 10 min, the reaction medium was stirred at ambient temperature for 19 hours. The reaction medium was hydrolyzed with a 1 N aqueous hydrochloric acid solution and extracted with ethyl acetate. The organic phase was washed with a 1 N aqueous hydrochloric acid solution, dried over anhydrous sodium sulfate, filtered and concentrated. The residue (11.82 g) was chromatographed on silica gel (300 g prepacked column, eluent heptane/ethyl acetate from 40% to 80% of ethyl acetate, 150 ml/min). 6.10 g of 6-chloro-2-hydroxy-N,N-dimethyl-3-nitrobenzamide were obtained in the form of a yellow solid. Yield=59%.

Step 3

6-Chloro-3-(2-ethoxy-3,4-dioxocyclobut-1-enylamino)-2-hydroxy-N,N-dimethylbenzamide A solution of 5.96 g (24.4 mmol, 1 eq) of 6-chloro-2-hydroxy-N,N-dimethyl-3-nitrobenzamide in 100 ml of methanol in the presence of 0.58 g of platinum oxide hydrate was stirred at hydrogen atmospheric pressure for 3 hours. The reaction medium was filtered through celite and the filtrate was concentrated. The solution obtained was added dropwise to 8.0 g (48.8 mmol, 2 eq) of 3,4-diethoxy-3-cyclobutene-1,2-dione in solution in 50 ml of methanol. The reaction medium was stirred at ambient temperature for 18 hours. The solvent was evaporated off and the residue was chromatographed on silica gel (300 g prepacked column, eluent heptane/acetone, from 50 to 100% of acetone). 4.42 g of 6-chloro-3-(2-ethoxy-3,4-dioxocyclobut-1-enylamino)-2-hydroxy-N,N-dimethylbenzamide were obtained in the form of a beige solid. Yield=54%.

Step 4

6-Chloro-2-hydroxy-N,N-dimethyl-3-(2-{[(R)-(5-methylfuran-2-yl)-(3-methyloxetan-3-yl) methyl]amino}-3,4-dioxocyclobut-1-enylamino)benzamide A mixture of 412 mg (2.27 mmol, 1.1 eq) of C—(R)-(5-methylfuran-2-yl)-C-(3-methyloxetan-3-yl)methylamine (prepared in EXAMPLE 50, steps 1 to 4) and 700 mg (2.07 mmol, 1 eq) of 6-chloro-3-(2-ethoxy-3,4-dioxocyclobut-1-enylamino)-2-hydroxy-N,N-dimethylbenzamide in 45 ml of methanol was stirred at ambient temperature for 3 days. The methanol was evaporated off and the residue was taken up with ethyl acetate and washed with a 1 M aqueous sodium dihydrogen phosphate solution. The organic phase was dried over anhydrous sodium sulfate, filtered and concentrated. The residue (0.90 g) was chromatographed on silica gel (80 g prepacked column, eluent dichloromethane/methanol, from 0 to 10% of methanol). 520 mg of 6-chloro-2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide were obtained in the form of an ochre solid. Yield=53%. Mp=165-167° C.

$^1$H NMR (DMSO-d6, 400 MHz): 1.31 (s, 3H), 2.21 (s, 3H), 2.79 (s, 3H), 3.00 (s, 3H), 4.28 (d, J=6.1 Hz, 2H), 4.55-4.58 (m, 1H), 4.64 (d, J=6.2 Hz, 1H), 5.64 (d, J=9.6 Hz, 1H), 6.05 (m, 1H), 6.24 (m, 1H), 6.85-7.05 (m, 1H), 7.69-7.74 (m, 1H), 8.75-8.90 (m, 1H), 9.35-9.60 (m, 1H), 9.90-10.30 (m, 1H)

EXAMPLE 53

Preparation of 3-[4-chloro-2-hydroxy-3-(4-methylpiperazine-1-sulfonyl)phenylamino]-4-{[(R)-(5-methylfuran-2-yl)-(3-methyloxetan-3-yl)methyl]amino}cyclobut-3-ene-1,2-dione

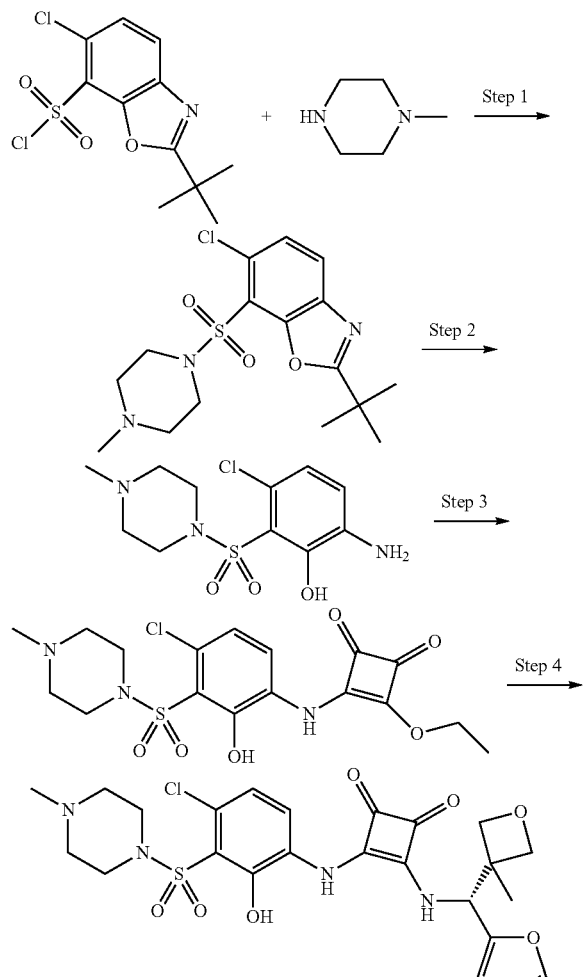

Step 1

2-tert-Butyl-6-chloro-7-(4-methylpiperazine-1-sulfonyl)benzooxazole 1.62 ml (11.68 mmol; 1.2 eq) of triethylamine followed by 1.20 ml (10.71 mmol; 1.1 eq) of 1-methylpiperazine were added to a solution of 3.0 g (9.73 mmol; 1.0 eq) of 2-tert-butyl-6-chlorobenzooxazole-7-sulfonyl chloride in 45 ml of tetrahydrofuran. The reaction medium was stirred at ambient temperature for 2 hours. Water was added and the reaction medium was extracted with ethyl acetate. The organic phases were combined, dried over magnesium sulfate, filtered and evaporated. 3.57 g of 2-tert-butyl-6-chloro-7-(4-methylpiperazine-1-sulfonyl)benzooxazole were obtained in the form of a tacky brown foam. Yield=98%.

Step 2

6-Amino-3-chloro-2-(4-methylpiperazine-1-sulfonyl)phenol 4.27 ml (0.08 mol; 1.20 V) of sulfuric acid diluted in 4.3 ml of water were added dropwise to 3.56 g of 2-tert-butyl-6-chloro-7-(4-methylpiperazine-1-sulfonyl)benzooxazole (0.01 mol; 1.0 eq) in solution in 15 ml of 1,4-dioxane. The reaction medium was refluxed for six and a half hours. The reaction medium was concentrated and 1 N sodium hydroxide was added (to pH 7). The solution was extracted with dichloromethane. The organic phases were combined, dried over magnesium sulfate, filtered and evaporated. The residue obtained was chromatographed on silica gel, eluent 95/5 ethyl acetate/dichloromethane. 2.0 g of 6-amino-3-chloro-2-(4-methylpiperazine-1-sulfonyl)phenol were obtained in the form of a thick brown oil. Yield=68%.

Step 3

3-[4-Chloro-2-hydroxy-3-(4-methylpiperazine-1-sulfonyl)phenylamino]-4-ethoxycyclobut-3-ene-1,2-dione A mixture of 1.98 g (6.5 mmol, 1 eq) of 6-amino-3-chloro-2-(4-methylpiperazine-1-sulfonyl)phenol and 2.20 g (48.8 mmol, 2 eq) of 3.4-diethoxy-3-cyclobutene-1,2-dione in solution in 20 ml of ethanol. The reaction medium was heated at 50° C. for 16 hours. The insoluble material was filtered off, washed with ethanol and dried under vacuum at 45° C. 2.05 g of 3-[4-chloro-2-hydroxy-3-(4-methylpiperazine-1-sulfonyl)phenylamino]-4-ethoxycyclobut-3-ene-1,2-dione were obtained in the form of a yellow solid. Yield=74%.

Step 4

3-[4-Chloro-2-hydroxy-3-(4-methylpiperazine-1-sulfonyl)phenylamino]-4-{[(R)-(5-methylfuran-2-yl)-(3-methyloxetan-3-yl)methyl]amino}cyclobut-3-ene-1,2-dione A mixture of 250 mg (1.4 mmol, 1.2 eq) of C—(R)-(5-methylfuran-2-yl)-C-(3-methyloxetan-3-yl)methylamine (prepared in EXAMPLE 50, steps 1 to 4) and 500 mg (1.16 mmol, 1 eq) of 3-[4-chloro-2-hydroxy-3-(4-methylpiperazine-1-sulfonyl)phenylamino]-4-ethoxycyclobut-3-ene-1,2-dione in 20 ml of methanol was heated at 50° C. for 16 hours. The methanol was evaporated off and the residue was chromatographed on silica gel eluted with dichloromethane/methanol (98/2). The residue was washed with a 1 M aqueous sodium dihydrogen phosphate solution. The organic phase was dried over anhydrous sodium sulfate, filtered and evaporated. 450 mg of 3-[4-chloro-2-hydroxy-3-(4-methylpiperazine-1-sulfonyl)phenylamino]-4-{[(R)-(5-methylfuran-2- yl)-(3-methyloxetan-3-yl)methyl]amino}cyclobut-3-ene-1,2-dione were obtained in the form of a dark yellow solid. Yield=68%.

$^1$H NMR (DMSO-d6, 400 MHz): 1.31 (s, 3H); 2.26 (s, 3H); 2.42 (bs, 3H); 2.70 (bs, 4H); 3.37 (bs, 4H); 4.28 (d, j=6.1 Hz, 1H); 4.29 (d, j=6.1 Hz, 1H); 4.57 (d, j=6.2 Hz, 1H); 4.65 (d, j=6.2 Hz, 1H); 5.62 (d, j=9.7 Hz, 1H); 6.06 (m, 1H); 6.24 (m, 1H); 6.70 (bs, 1H); 7.85 (d, j=8.5 Hz, 1H); 8.97 (d, j=9.8 Hz, 1H); 9.60 (s, 1H); 10.00 (bs, 1H).

BIOLOGICAL TESTS

EXAMPLE 54

In Vitro Affinity

The in vitro affinity of the compounds of the present invention for the CXCR1 and CXCR2 receptors was determined on a functional test of the β-arrestin recruitment type after receptor activation.

It was demonstrated that the activation by CXCL8 of the CXCR2 receptor in cells of the PathHunter HEK293-CXCR2 line or of the CXCR1 receptor in cells of the U2OS h CXCR1 β-arrestin line results in the recruitment of β-arrestin (Richardson et al. 2003 Role of the cytoplasmic tails of CXCR1 and CXCR2 in mediating leukocyte migration, activation, and regulation. J. Immunol. 170: 2904-2911.)

In order to evaluate the direct interaction of the CXCR2 or CXCR1 receptor with β-arrestin 2, a β-arrestin 2 recruitment test for CXCR2 or CXCR1 based on of β-galactosidase enzyme complementation (Olson K R, Eglen R M. Beta galactosidase complementation: a cell-based luminescent assay platform for drug discovery. Assay Drug Dev Technol. 2007 February; 5(1); 137-44), as established by DiscoveRx Corporation was used. The stimulation of these two cell lines with CXCL8 (10 nM) induces β-arrestin 2 recruitment, as indicated by a significant increase in the induction factor. All the CXCR2 antagonists were tested in a dose-dependent manner and the concentration corresponding to 50% inhibition of the response was determined ($IC_{50}$=half inhibition concentration).

β-Arrestin Recruitment Assay:

"PathHunter HEK293-CXCR2" or "U2OS hCXCR1 β-arrestin" cells (DiscoveRx Corporation) were seeded overnight at 10 000 cells/well (384-well format) in 20 µl of Opti MEM I medium. A preincubation with the antagonist or the vehicle for 30 min at 37° C. and 5% $CO_2$ was followed by 60 minutes of stimulation with CXCL8 at 37° C. and 5% $CO_2$. The cells were then placed at ambient temperature for 30 minutes. The PathHunter detection reagent (DiscoveRx Corporation) was added. After incubation for 60 min at ambient temperature, the β-galactosidase induced by the luminescence during the β-arrestin-CXCR2 interaction was measured for 0.3 s in an Envision 2102 Multilabel Reader (PerkinElmer Life and Analytical Sciences). The data were analyzed by means of a non-linear curve procedure using the XLFit4 exploitation software (IDBS) and the IC50 values were determined.

| Compound (Example No.) | CXCR1 (nM) | CXCR2 (nM) |
|---|---|---|
| 38 | 322 | 25 |
| 48 | 566 | 26 |
| 22 | 117 | 31 |
| 37a | 827 | 32 |
| 8 | 604 | 37 |
| 9 | 666 | 60 |
| 50 | 312 | 72 |
| 25 | 3899 | 96 |
| 7 | 2412 | 100 |
| 12 | 9999 | 100 |
| 34 | 1611 | 106 |
| 3 | 1150 | 106 |
| 35 | 3031 | 146 |
| 36 | 1706 | 198 |
| 37b | 7685 | 207 |
| 27 | 1541 | 244 |
| 21 | 1442 | 257 |
| 14 | 1300 | 262 |
| 2 | 1595 | 272 |
| 42 | 9999 | 311 |
| 20 | 6621 | 335 |
| 5 | 2620 | 341 |
| 30 | 2245 | 349 |
| 19 | 4957 | 394 |
| 29 | 9999 | 433 |
| 28 | 5541 | 475 |
| 40 | 5225 | 502 |
| 11 | 6510 | 549 |
| 15 | 3171 | 626 |
| 31 | 3533 | 716 |
| 49 (S enantiomer) | 7386 | 733 |
| 33 | 9999 | 962 |
| 39 | 9999 | 1035 |
| 6 | 2841 | 1088 |
| 51 | 650 | 72 |
| 52 | 897 | 373 |
| 53 | 115 | 30 |

EXAMPLE 55

Polypharmacology: "Receptor Profiling"

Measurement of Calcium Flux on Cells:

The experiments were carried out on the FLIPR TETRA® platform from Molecular Devices. After the basal level had been read, the compounds were added to the cells expressing the chemokine receptor of interest and the agonist activity was read at 10 seconds. After a further incubation for 10 minutes, the cells were activated, with a concentration equivalent to the AC80, using a reference agonist in order to detect whether this compound exhibits antagonist activity.

Each cell line expressing a chemokine receptor was established on the basis of the Chem-1 cell stably expressing the recombinant form of the chemokine receptor and also an associated G protein, with the aim of coupling the receptor to the calcium signalling pathway. 21 receptors belonging to the chemokine receptor family (CCRs and CXCRs) were analyzed. All the CXCR2 antagonists were tested in a dose-dependent manner and the concentration corresponding to 50% inhibition of the response was determined ($IC_{50}$).

| | IC50 (nM) | | |
|---|---|---|---|
| Antagonist | CCR4 | CCR6 | CXCR3 |
| Example 50 | IA | 1.4 | 700 |
| Example 22 | 1500 | 3.4 | 3300 |
| Example 53 | 450 | 1.9 | 920 |
| Example 8 | IA | 5.8 | 240 |

IA: Inactive

EXAMPLE 56

Dissociation Constant

The determination of the half-dissociation constants of the CXCR2 antagonists was based on the in vitro β-arrestin recruitment model previously described: "PathHunter HEK293-CXCR2" cells (DiscoveRx Corporation) were seeded overnight at 20 000 cells/well (in a 96-well format) in 100 μl/well of OptiMEM culture medium-1% FCS. A preincubation with the antagonist or the vehicle was carried out for 1 hour at 37° C.-5% $CO_2$. The cells were then washed 3 times with 100 μl/well of OptiMEM culture medium-1% FCS and then a variable incubation (0 h-0.5 h-6 h-12 h-24 h) of the cells at 37° C.-5% $CO_2$ was carried out. The cells were then stimulated with 4 nM of CXCL8 at 37° C.-5% $CO_2$ for 1 h 30 min. The PathHunter detection reagent (DiscoveRx Corporation) was added in a proportion of 50 μl/well. After incubation for 60 minutes at ambient temperature, the luminescence emitted, via the hydrolysis of the substrate by the β-galactosidase complemented during the β-arrestin-CXCR2 interaction, was measured for 0.3 seconds/well with an Envision Multilabel Reader (PerkinElmer Life and Analytical Sciences). The data were analyzed by means of a non-linear curve procedure using the XLFit4 exploitation software (IDBS) and the IC50 values were determined. The half-dissociation time was determined on a regression of type $y=(A*(1-\exp(((-1)*B)*x)))$ (where x=time and y=standardized luminescence) at saturating concentration of antagonist.

Results:

The molecules described in the present invention were compared to the SCH-527123 molecule (described as having a pseudo-irreversible dissociation) (Pharmacological Characterization of SCH-527123, a Potent Allosteric CXCR1/CXCR2 Antagonist. JPET 322:477-485, 2007).

| Antagonist | Half-dissociation time (hours) |
|---|---|
| DMSO (vehicle) | nd |
| SCH-527123 | >96 |
| Example 50 | 11 |

EXAMPLE 57

A/ Metabolic Stabilities in Hepatic Microsomes

Hepatic microsomes (Becton Dickinson) were incubated at a protein concentration of 0.5 mg/ml in the reaction medium.

The reaction medium of the microsomes was composed of phosphate buffer, pH: 7.4 at 100 mM, of $MgCl_2$ at 100 mM (50/50), of an ATP-generating system composed of a mixture of nicotinamide adenine dihosphate (NADP) and of glucose-6-phosphate (G6P) at 1 mg/ml and of glucose-6-phosphate dehydroganase (G6PDH) at 4 U/ml. The compounds were tested at 1 μM (0.1% DMSO).

The samples of incubation medium after addition of the microsomes were taken at times 5, 10, 15, 30 and 60 minutes. At each time, the metabolic reaction was stopped by adding methanol (1 volume incubation medium/3 volumes of methanol). The disappearance of the parent product was measured by LC/MS/MS analysis. The time for which 50% of parent Product disappeared (T½) was calculated from the kinetics of disappearance of the parent product as a function of time.

| Antagonist | Half-life time (min) |
|---|---|
| SCH-527123 | Stable (>60 min) |
| Example 21 | 7.7 |
| Example 22 | 57 |
| Example 53 | 47 |

B/ Metabolic Stabilities in Hepatocytes

The human hepatocytes were supplied by Biopredic in 24-well plates. After 48 h of adaptation in culture, the hepatocytes were placed in a treatment medium containing 0.1% bovine serum albumin, and the compounds were tested at 1 μM (0.1% DMSO).

The samples of incubation medium after addition of the test compound were taken at times t=0, 1, 2, 4, 6 and 24 hours.

At each time, the metabolic reaction was stopped by adding methanol (1 volume incubation medium/3 volumes of methanol). The disappearance of the parent product was measured by LC/MS/MS analysis. The time for which 50% (T½) of parent product disappeared was calculated from the kinetics of disappearance of the parent product as a function of time.

| Antagonist | Half-life time (min) |
|---|---|
| SCH-527123 | 900 |
| Example 22 | 445 |
| Example 53 | 186 |

The invention claimed is:

1. A disubstituted 3,4-diamino-3-cyclobutene-1,2-dione compound corresponding to general formula (I) below, or one of the pharmaceutically acceptable salts or solvates thereof:

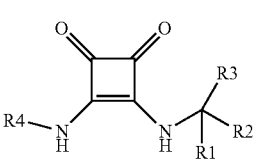

(I)

in which,

R1 represents a hydrogen atom or a methyl,

R2 represents a ring comprising four atoms, chosen from structures (1) and (2) below:

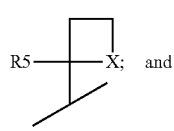

(1)

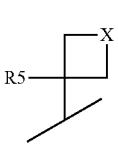

(2)

in which R5 and X have the meaning given hereinafter,

R3 represents an aromatic or heteroaromatic ring selected from the group consisting of the rings corresponding to formulae (a) to (o) below:

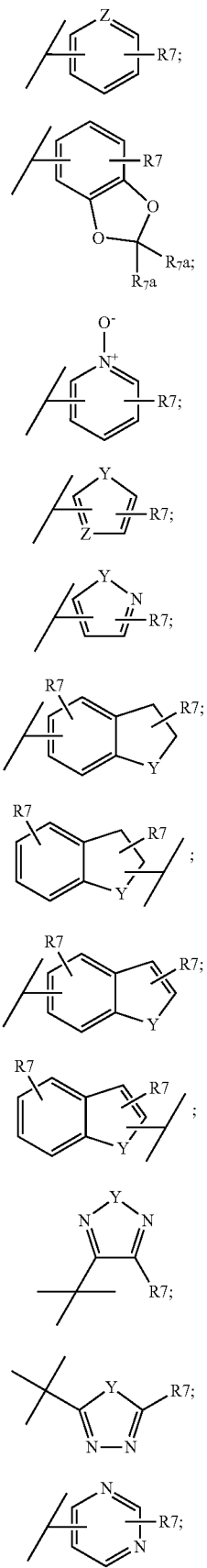

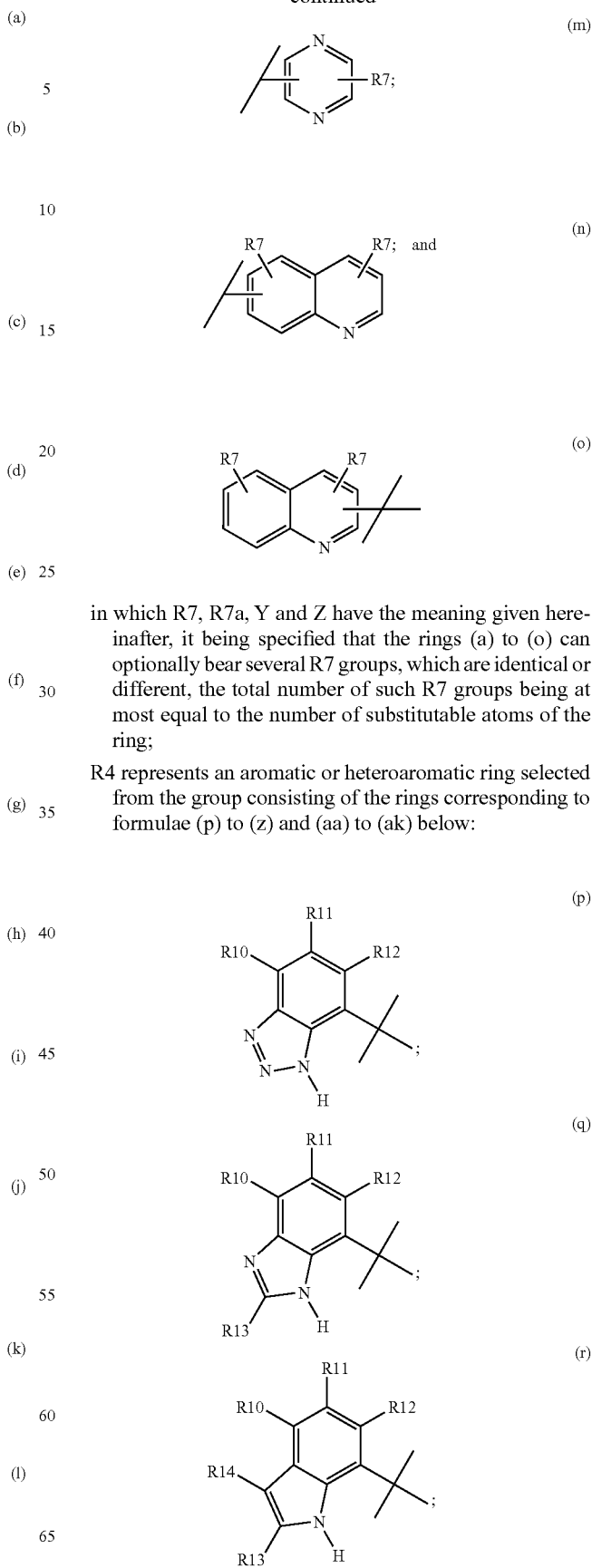

in which R7, R7a, Y and Z have the meaning given hereinafter, it being specified that the rings (a) to (o) can optionally bear several R7 groups, which are identical or different, the total number of such R7 groups being at most equal to the number of substitutable atoms of the ring;

R4 represents an aromatic or heteroaromatic ring selected from the group consisting of the rings corresponding to formulae (p) to (z) and (aa) to (ak) below:

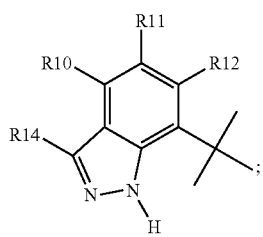 (s)
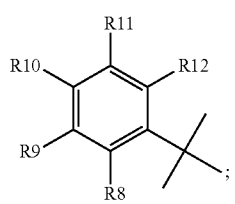 (t)
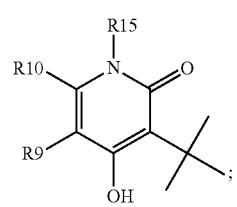 (u)
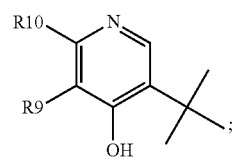 (v)
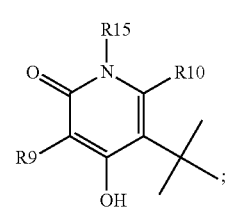 (w)
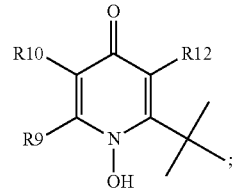 (x)
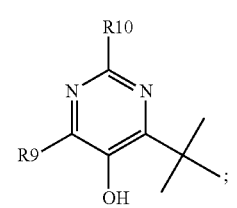 (y)
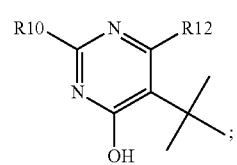 (z)
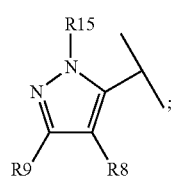 (aa)
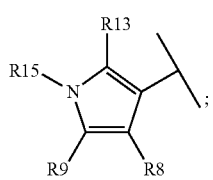 (ab)
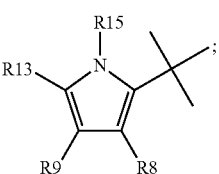 (ac)
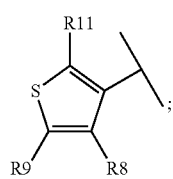 (ad)
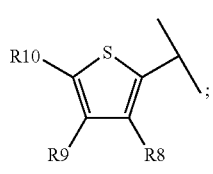 (ae)
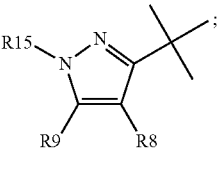 (af)
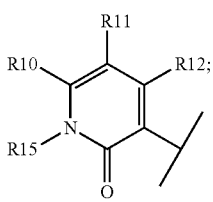 (ag)
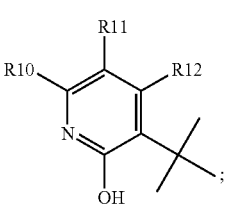 (ah)

99

-continued

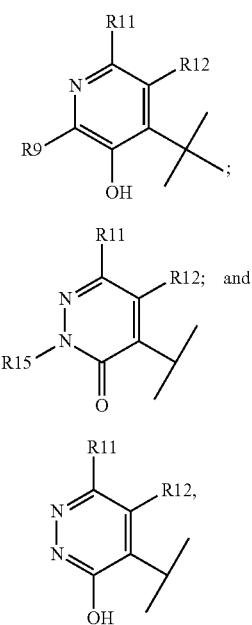

(ai)

(aj)

(ak)

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a radical R16, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R7a represents a hydrogen atom or else an alkyl radical having from 1 to 5 carbon atoms, R8 represents a hydrogen atom, a halogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on an aromatic or heteroaromatic ring selected from the group consisting of the rings corresponding to formulae (p) to (z) and (aa) to (ak) above, then they can together form, with the bond which links them together, an aryl, heteroaryl, cycloalkyl or heterocycloalkyl ring, R13 and R14 are identical or different and are independently selected from the group consisting of a hydrogen atom, a halogen atom, an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 and —CO$_2$R16,

100

R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms selected from the group consisting of oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

2. The compound as claimed in claim 1, wherein in the abovementioned formula (I):

R1 represents a hydrogen atom,

R2 represents a four-membered ring corresponding to structure (2) below:

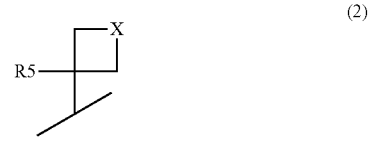

(2)

in which R5 and X have the meaning given hereinafter,

R3 represents an aromatic or heteroaromatic ring selected from the group consisting of the rings corresponding to formulae (a), (b) and (d) below:

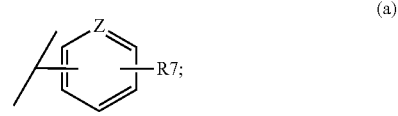

(a)

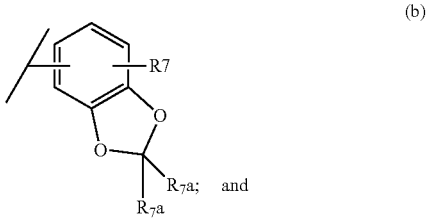

(b)

(d)

in which R7, R7a, Y and Z have the meaning given hereinafter, it being specified that the rings (a), (b) and (d) can optionally bear several R7 groups, which are identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

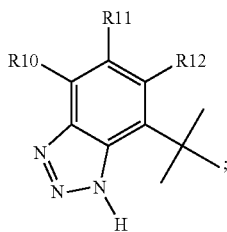  (p)

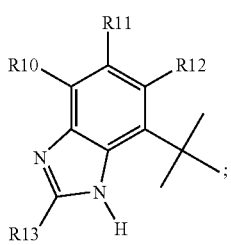  (q)

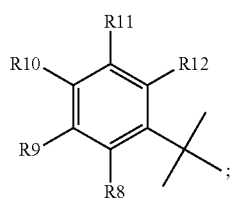  (t)

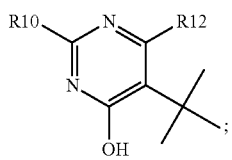  (z)

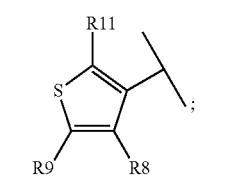  (ad)

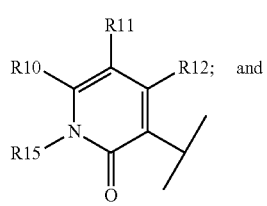  (ag)

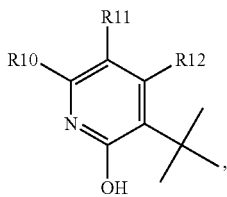  (ah)

in which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R7a represents a hydrogen atom or else an alkyl radical having from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, then they can together form, with the bond which links them together, an aryl, heteroaryl, cycloalkyl or heterocycloalkyl ring, R13 is selected from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 and —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms selected from the group consisting of oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

3. The compound as claimed in claim 1, wherein in the abovementioned formula (I):

R1 represents a hydrogen atom,

R2 represents a ring comprising four atoms, corresponding to structure (2) below:

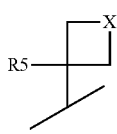

(2)

in which R5 and X have the meaning given hereinafter,

R3 represents a heteroaromatic ring corresponding to formula (d) below:

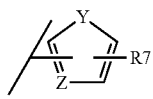

(d)

in which R7, Y and Z have the meaning given hereinafter, it being specified that the ring (d) can optionally bear several R7 groups, which are identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

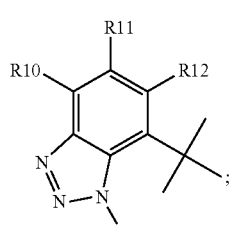

(p)

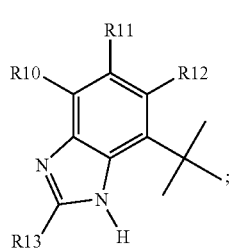

(q)

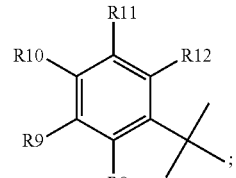

(t)

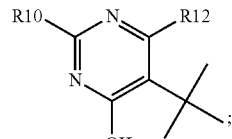

(z)

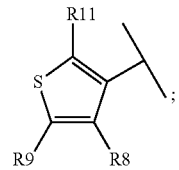

(ad)

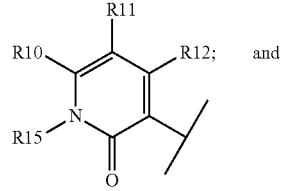

(ag)

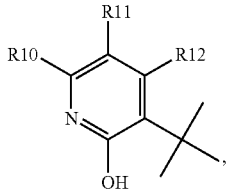

(ah)

in which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen atom, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, they can together form, with the bond which links them together, an aryl, heteroaryl, cycloalkyl or heterocycloalkyl ring, R13 is selected from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 and —CO$_2$R16 radical, R15 represents a hydrogen atom, or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms selected from the group consisting of oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

4. The compound as claimed in claim 1, wherein in the abovementioned formula (I):

R1 represents a hydrogen atom,

R2 represents a ring comprising four atoms, corresponding to structure (2) below:

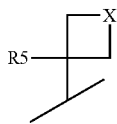

(2)

in which R5 and X have the meaning given hereinafter,

R3 represents a heteroaromatic ring corresponding to formula (d) below:

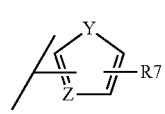

(d)

in which R7, Y and Z have the meaning given hereinafter, it being specified that the ring (d) can optionally bear several R7 groups, which are identical or different, the total number of such R7 groups being at most equal to the number of substitutable atoms of the ring;

R4 represents an aromatic ring corresponding to formula (t) below:

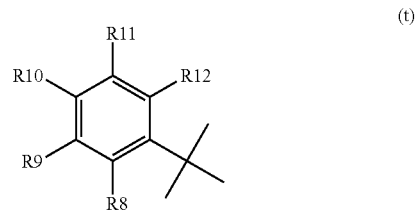

(t)

in which R8, R9, R10, R11 and R12 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a radical R16, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on the aromatic ring (t), they can together form, with the bond which links them together, an aryl, heteroaryl, cycloalkyl or heterocycloalkyl ring, R16 and R17 are identical or different and are independently selected from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms selected from the group consisting of oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

5. A pharmaceutical composition comprising an effective amount of the compound, or pharmaceutically acceptable salt of the compound, as claimed in claim 1, in combination with a pharmaceutically acceptable solvent or support.

6. A medicament comprising the compound as claimed in claim 1 or a pharmaceutical composition comprising the compound.

7. A method of treating a disease, the method comprising administering an effective amount of the compound of claim 1 or the pharmaceutical composition as claimed in claim 5, to an individual subject in need thereof, wherein the disease is selected from the group consisting of neutrophilic dermatosis, psoriasis, atopic dermatitis, acne, rosacea, asthma, chronic obstructive pulmonary diseases, arthritis, inflammatory bowel diseases, Crohn's disease, transplant rejection, and cystic fibrosis.

8. A method of treating a skin disease, the method comprising administering an effective amount of the compound of claim 1 or the pharmaceutical composition as claimed in claim 5, to an individual subject in need thereof, wherein the skin disease is selected from the group consisting of neutrophilic dermatosis, psoriasis, atopic dermatitis, acne and rosacea.

9. A disubstituted 3,4-diamino-3-cyclobutene-1,2-dione compound selected from the group consisting of:

1/ 2-hydroxy-N,N-dimethyl-3-(2-{[(5-methylfuran-2-yl)-(3-methyloxetan-3-yl)methyl]amino}-3,4-dioxocyclobut-1-enylamino)benzamide;

2/ 3-(2-{[(3-fluoromethyloxetan-3-yl)-(5-methyl-furan-2-yl)methyl]amino}-3,4-dioxocyclobut-1-enylamino)-2-hydroxy-N,N-dimethylbenzamide;

3/ 3-(2-{[(3-ethyloxetan-3-yl)-(5-methylfuran-2-yl)methyl]amino}-3,4-dioxocyclobut-1-enylamino)-2-hydroxy-N,N-dimethylbenzamide;

4/ 2-hydroxy-3-(2-{[(5-methylfuran-2-yl)-(3-methyloxetan-3-yl)methyl]amino}-3,4-dioxocyclobut-1-enylamino)benzoic acid;

5/ 3-[2-hydroxy-3-((R)-3-hydroxypyrrolidine-1-carbonyl)phenylamino]-4-{[(5-methylfuran-2-yl)-(3-methyloxetan-3-yl)methyl]amino}cyclobut-3-ene-1,2-dione;

6/ 3-[2-hydroxy-3-((S)-3-hydroxypyrrolidine-1-carbonyl)phenylamino]-4-{[(5-methylfuran-2-yl)-(3-methyloxetan-3-yl)methyl]amino}cyclobut-3-ene-1,2-dione;

7/ (R)-1-[2-hydroxy-3-(2-{[(5-methylfuran-2-yl)-(3-methyloxetan-3-yl)methyl]amino}-3,4-dioxocyclobut-1-enylamino)benzoyl]pyrrolidine-2-carboxylic acid tert-butyl ester;

8/ methyl (R)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate;

9/ methyl (S)-1-[2-hydroxy-3-(2-{[(R)-(5-methylfuran-2-yl)-(3-methyloxetan-3-yl)methyl]amino}-3,4-dioxocyclobut-1-enylamino)benzoyl]pyrrolidine-2-carboxylate;

10/ (R)-1-[2-hydroxy-3-(2-{[(5-methylfuran-2-yl)-(3-methyloxetan-3-yl)methyl]amino}-3,4-dioxocyclobut1-enylamino)benzoyl]pyrrolidine-2-carboxylic acid;

11/ 3-[2-hydroxy-3-(1-hydroxyethyl)phenylamino]-4-{[(5-methylfuran-2-yl)-(3-methyloxetan-3-yl)methyl]amino}cyclobut-3-ene-1,2-dione;

12/ 3-(2-hydroxy-3-isobutyrylphenylamino)-4-{[(5-methylfuran-2-yl)-(3-methyloxetan-3-yl)methyl]amino}cyclobut-3-ene-1,2-dione;

13/ 3-(4-hydroxy-2-methyl-3-oxo-2,3-dihydro-1H-isoindol-5-ylamino)-4-{[(5-methylfuran-2-yl)-(3-methyloxetan-3-yl)methyl]amino}cyclobut-3-ene-1,2-dione;

14/ 3-[2-hydroxy-3-(pyrrolidine-1-carbonyl)phenylamino]-4-{[(5-methylfuran-2-yl)-(3-methyloxetan-3-yl)methyl]amino}cyclobut-3-ene-1,2-dione;

15/ 3-[2-hydroxy-3-(morpholine-4-carbonyl)phenylamino]-4-{[(5-methylfuran-2-yl)-(3-methyloxetan-3-yl)methyl]amino}cyclobut-3-ene-1,2-dione;

16/ 3-(4-hydroxypyrimidin-5-ylamino)-4-{[(5-methylfuran-2-yl)-(3-methyl-oxetan-3-yl)methyl]amino}cyclobut-3-ene-1,2-dione;

17/ 3-{[(5-methylfuran-2-yl)-(3-methyloxetan-3-yl)methyl]amino}-4-(1-methyl-2-oxo-1,2-dihydroquinolin-3-ylamino)cyclobut-3-ene-1,2-dione;

18/ 3-{[(5-methylfuran-2-yl)-(3-methyloxetan-3-yl)methyl]amino}-4-(6-methyl-2-oxo-2H-pyran-3-ylamino)cyclobut-3-ene-1,2-dione;

19/ 3-{[(5-methylfuran-2-yl)-(3-methyloxetan-3-yl)methyl]amino}-4-(1-methyl-2-oxo-1,2-dihydropyridin-3-ylamino)cyclobut-3-ene-1,2-dione;

20/ 3-(2-hydroxypyridin-3-ylamino)-4-{[(5-methylfuran-2-yl)-(3-methyloxetan-3-yl)methyl]amino}cyclobut-3-ene-1,2-dione;

21/ 2-hydroxy-N,N-dimethyl-3-(2-{[(5-methylfuran-2-yl)-(3-methyloxetan-3-yl)methyl]amino}-3,4-dioxocyclobut-1-enylamino)benzenesulfonamide;

22/ 2-hydroxy-N,N-dimethyl-3-(2-{[(R)-(5-methylfuran-2-yl)-(3-methyloxetan-3-yl)methyl]amino}-3,4-dioxocyclobut-1-enylamino)benzenesulfonamide;

23/ 3-(3H-benzothazol-4-ylamino)-4-{[(5-methylfuran-2-yl)-(3-methyloxetan-3-yl)methyl]amino}cyclobut-3-ene-1,2-dione;

24/ 3-{[(5-methyl-furan-2-yl)-(3-methyloxetan-3-yl)methyl]amino}-4-(2-oxo-2,3-dihydrobenzooxazol-7-ylamino)cyclobut-3-ene-1,2-dione;

25/ dimethylamide 3-hydroxy-4-(2-{[(R)-(5-methylfuran-2-yl)-(3-methyloxetan-3-yl)methyl]amino}-3,4-dioxcyclobut-1-enylamino)thiophene-2-carboxylate;

26/ tert-butyl 3-[[2-(3-dimethylcarbamoyl-2-hydroxyphenylamino)-3,4-dioxo-cyclobut-1-enylamino]-(5-methylfuran-2-yl)methyl]-3-methylazetidine-1-carboxylate;

27/ 3-(2-{[(4,5-dimethylfuran-2-yl)-(3-methyloxetan-3-yl)methyl]amino}-3,4-dioxocyclobut-1-enylamino)-2-hydroxy-N,N-dimethylbenzamide;

28/ 3-(2-{[(3-methyloxetan-3-yl)-(3-methoxyphenyl)methyl]amino}-3,4-dioxocyclobut-1-enylamino)-2-hydroxy-N,N-dimethylbenzamide;

29/ 3-(2-{[(3-methyloxetan-3-yl)-(4-methoxyphenyl)methyl]amino}-3,4-dioxocyclobut-1-enylamino)-2-hydroxy-N,N-dimethylbenzamide;

30/ 3-(2-{[benzo[1,3]dioxol-5-yl-(3-methyloxetan-3-yl)methyl]amino}-3,4-dioxocyclobut-1-enylamino)-2-hydroxy-N,N-dimethylbenzamide;

31/ 3-[3-(3-hydroxypyrrolidine-1-carbonyl)phenylamino]-4-{[(5-methylfuran-2-yl)-(3-methyloxetan-3-yl)methyl]amino}cyclobut-3-ene-1,2-dione;

32/ methyl 1-[3-(2-{[(5-methylfuran-2-yl)-(3-methyloxetan-3-yl)methyl]amino}-3,4-dioxocyclobut-1-enylamino)benzoyl]piperidine-2-carboxylate;

33/ methyl 1-[3-(2-{[(5-methylfuran-2-yl)-(3-methyloxetan-3-yl)methyl]amino}-3,4-dioxocyclobut-1-enylamino)benzoyl]pyrrolidine-2-carboxylate;

34/ 2-hydroxy-N,N-dimethyl-3-(2-{[(3-methyloxetan-3-yl)thiophen-2-ylmethyl]amino}-3,4-dioxocyclobut-1-enylamino)benzamide;

35/ 2-hydroxy-N,N-dimethyl-3-(2-{[(3-methyloxetan-3-yl)-(5-methylthiophen-2-yl)methyl]amino}-3,4-dioxocyclobut-1-enylamino)benzamide;

36/ 3-(2-{[furan-2-yl-(3-methyloxetan-3-yl)methyl]amino}-3,4-dioxocyclobut-1-enylamino)-2-hydroxy-N,N-dimethylbenzamide;

37a/ 2-hydroxy-N,N-dimethyl-3-(2-{[(4-methylfuran-2-yl)-(3-methyloxetan-3-yl)methyl]amino}-3,4-dioxocyclobut-1-enylamino)benzamide;

37b/ 2-hydroxy-N,N-dimethyl-3-(2-{[(3-methylfuran-2-yl)-(3-methyloxetan-3-yl)methyl]amino}-3,4-dioxocyclobut-1-enylamino)benzamide;

38/ 2-hydroxy-N,N-dimethyl-3-(2-{[(4-isopropylfuran-2-yl)-(3-methyloxetan-3-yl)methyl]amino}-3,4-dioxocyclobut-1-enylamino)benzamide;

39/ 3-(2-hydroxy-6-methoxypyridin-3-ylamino)-4-{[(5-methylfuran-2-yl)-(3-methyloxetan-3-yl)methyl]amino}cyclobut-3-ene-1,2-dione;

40/ 3-(6-chloro-2-hydroxypyridin-3-ylamino)-4-{[(5-methylfuran-2-yl)-(3-methyloxetan-3-yl)methyl]amino}cyclobut-3-ene-1,2-dione;

41/ 3-{[(5-methylfuran-2-yl)-(3-methyloxetan-3-yl)methyl]amino}-4-(2-oxo-2,3-dihydro-1H-benzoimidazol-4-ylamino)cyclobut-3-ene-1,2-dione;

42/ 2-hydroxy-3-(2-{[(5-methylfuran-2-yl)-(3-methyloxetan-3-yl)methyl]amino}-3,4-dioxocyclobut-1-enylamino)benzonitrile;

43/ methyl (R)-1-[3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate;

44/ methyl (S)-1-[4-chloro-3-(2-{[(5-methylfuran-2-yl)-(3-methyloxetan-3-yl)methyl]amino}-3,4-dioxocyclobut-1-enylamino)benzenesulfonyl]pyrrolidine-2-carboxylate;

45/ methyl (S)-1-[2,6-difluoro-3-(2-{[(5-methylfuran-2-yl)-(3-methyloxetan-3-yl)methyl]amino}-3,4-dioxocyclobut-1-enylamino)benzoyl]pyrrolidine-2-carboxylate;

46/ methyl (S)-1-[2-chloro-3-(2-{[(5-methylfuran-2-yl)-(3-methyloxetan-3-yl)methyl]amino}-3,4-dioxocyclobut-1-enylamino)benzoyl]pyrrolidine-2-carboxylate;

47/ methyl (R)-1-[2-hydroxy-3-(2-{[(R)-(5-methylfuran-2-yl)-(3-methyloxetan-3-yl)-methyl]amino}-3,4-dioxocyclobut-1-enylamino)benzoyl]pyrrolidine-2-carboxylate;

48/ 2-hydroxy-N-methyl-3-(2-{[(R)-(5-methylfuran-2-yl)-(3-methyloxetan-3-yl)methyl]amino}-3,4-dioxocyclobut-1-enylamino)-N-(2,2,2-trifluoroethyl)benzamide; 49/ 2-hydroxy-N,N-dimethyl-3-(2-{[((R)-5-methylfuran-2-yl)-(3-methyloxetan-3-yl)methyl]amino}-3,4-dioxocyclobut-1-enylamino)benzamide;

51/ methyl {[2-hydroxy-3-(2-{[(R)-(5-methylfuran-2-yl)-(3-methyloxetan-3-yl)methyl]amino}-3,4-dioxocyclobut-1-enylamino)benzoyl]methylamino}acetate;

52/ 6-chloro-2-hydroxy-N,N-dimethyl-3-(2-{[(R)-(5-methylfuran-2-yl)-(3-methyloxetan-3-yl)methyl]amino}-3,4-dioxocyclobut-1-enylamino)benzamide; and 53/ 3-[4-chloro-2-hydroxy-3-(4-methylpiperazine-1-sulfonyl)phenylamino]-4-{[(R)-(5-methylfuran-2-yl)-(3-methyloxetan-3-yl)methyl]amino}cyclobut-3-ene-1,2-dione.

\* \* \* \* \*

UNITED STATES PATENT AND TRADEMARK OFFICE
CERTIFICATE OF CORRECTION

| | | |
|---|---|---|
| PATENT NO. | : 9,090,596 B2 | Page 1 of 1 |
| APPLICATION NO. | : 14/354500 | |
| DATED | : July 28, 2015 | |
| INVENTOR(S) | : Branislav Musicki et al. | |

It is certified that error appears in the above-identified patent and that said Letters Patent is hereby corrected as shown below:

Title page Item (73) Inventors:
please delete "Jean-Guy Boiteaux, Valbonne (FR)" and insert --Jean-Guy Boiteau, Valbonne (FR)--

Signed and Sealed this
First Day of December, 2015

Michelle K. Lee
*Director of the United States Patent and Trademark Office*